United States Patent
Mansfield

(10) Patent No.: US 11,136,332 B2
(45) Date of Patent: Oct. 5, 2021

(54) MORPHIC FORMS OF MARIZOMIB AND USES THEREOF

(71) Applicant: Celgene International II Sàrl, Couvet (CH)

(72) Inventor: Robert Mansfield, San Marcos, CA (US)

(73) Assignee: Celgene International II Sàrl, Couvet (CH)

( * ) Notice: Subject to any disclaimer, the term of this patent is extended or adjusted under 35 U.S.C. 154(b) by 0 days.

(21) Appl. No.: 16/886,301

(22) Filed: May 28, 2020

(65) Prior Publication Data

US 2021/0017185 A1 Jan. 21, 2021

Related U.S. Application Data

(63) Continuation of application No. 16/325,837, filed as application No. PCT/EP2017/070950 on Aug. 18, 2017, now Pat. No. 10,703,760.

(60) Provisional application No. 62/377,156, filed on Aug. 19, 2016.

(51) Int. Cl.
| | |
|---|---|
| *A61K 31/407* | (2006.01) |
| *A61P 35/00* | (2006.01) |
| *C07D 491/02* | (2006.01) |
| *C07D 491/048* | (2006.01) |

(52) U.S. Cl.
CPC .......... *C07D 491/048* (2013.01); *A61P 35/00* (2018.01); *C07D 491/02* (2013.01); *C07B 2200/13* (2013.01)

(58) Field of Classification Search
CPC ...... A61K 31/407; A61P 35/00; C07D 491/02
See application file for complete search history.

(56) References Cited

U.S. PATENT DOCUMENTS

| | | | |
|---|---|---|---|
| 7,144,723 B2 | 12/2006 | Fenical et al. | |
| 7,179,834 B2 | 2/2007 | Fenical et al. | |
| 7,276,530 B2 | 10/2007 | Palladino et al. | |
| 7,572,606 B1 | 8/2009 | Lam et al. | |
| 7,824,698 B2 | 11/2010 | Potts et al. | |
| 8,003,802 B2 | 8/2011 | Ling et al. | |
| 8,067,616 B2 | 11/2011 | Ling et al. | |
| 8,168,803 B2 | 5/2012 | Palladino et al. | |
| 8,227,503 B2 | 7/2012 | Macherla et al. | |
| 8,394,816 B2 | 3/2013 | Ghobrial | |
| 8,722,724 B2 | 5/2014 | Anderson et al. | |
| 8,986,971 B2 | 3/2015 | Lam et al. | |
| 10,703,760 B2 | 7/2020 | Mansfield | |
| 2005/0288352 A1 | 12/2005 | Potts et al. | |
| 2008/0280968 A1 | 11/2008 | Palladino et al. | |
| 2009/0148445 A1 | 6/2009 | Bonavida et al. | |
| 2017/0348284 A1 | 12/2017 | Trikha et al. | |

FOREIGN PATENT DOCUMENTS

| | | |
|---|---|---|
| WO | WO 2006/124902 A2 | 11/2006 |
| WO | WO 2007/120801 A2 | 10/2007 |
| WO | WO 2007/130404 A1 | 11/2007 |
| WO | WO 2008/124699 A1 | 10/2008 |
| WO | WO 2018/033631 A1 | 2/2018 |
| WO | WO 2018/169740 A1 | 9/2018 |

OTHER PUBLICATIONS

Feling, R. H. et al., "Salinosporamide A: A Highly Cytotoxic Proteasome Inhibitor from a Novel Microbial Source, a Marine Bacterium of the New Genus *Salinospora*," Angew. Chem. Int. Ed., 42(3):355-357 (2003); doi:10.1002/anie.200390115.

Fenical, W. et al., "Discovery and development of the anticancer agent salinosporamide A (NPI-0052)," Bioorganic & Medicinal Chemistry, 17:2175-2180 (2009).

Ling, T. et al., "Concise Formal Synthesis of (−)-Salinosporamide A (Marizomib) Using a Regio- and Stereoselective Epoxidation and Reductive Oxirane Ring-Opening Strategy," J. Org. Chem., 75(11):3882-3885 (2010); doi: 10.1021/jo100432g.

Millward, M. et al., "Phase 1 clinical trial of the novel proteasome inhibitor marizomib with the histone deacetylase inhibitor vorinostat in patients with melanoma, pancreatic and lung cancer based on in vitro assessments of the combination," Invest New Drugs, 30:2303-2317 (2012); doi: 10.1007/s10637-011-9766-6.

*Primary Examiner* — Brenda L Coleman

(74) *Attorney, Agent, or Firm* — Cooley LLP; J. Dean Farmer; Christine C. Pemberton

(57) ABSTRACT

The present invention relates to polymorphic forms of marizomib (e.g., Morphic Form I). The morphic forms can be used alone and in pharmaceutical compositions for the treatment of disease.

20 Claims, 46 Drawing Sheets

MORPHIC FORMS OF MARIZOMIB AND USES THEREOF

RELATED APPLICATIONS

This application is a continuation application of U.S. application No. 16/325,837, filed Feb. 15, 2019, now allowed, which is a U.S. National Phase application, filed under 35 U.S.C. § 371, of International application No. PCT/EP2017/070950, filed on Aug. 18, 2017, which claims priority to, and benefit of, U.S. Provisional Patent Application No. 62/377,156, filed Aug. 19, 2016, the contents of each of which are incorporated by reference in their entirety.

FIELD OF THE INVENTION

The present invention relates to polymorphic forms of marizomib (e.g., Morphic Form 1). The morphic forms can be used alone and in pharmaceutical compositions for the treatment of disease.

BACKGROUND OF THE INVENTION

Marizomib is a proteasome inhibitor capable of inhibiting all three domains of the proteasome (i.e., the chymotrypsin-like (CT-L); caspase-like (C-L) and trypsin-like (T-L) domains). Accordingly, marizomib can be useful for treating diseases such as cancer. Thus, there is a need for pure, stable morphic forms of marizomib that can be used for administration to subjects in need thereof. The present disclosure teaches stable and pure morphic forms of marizomib.

SUMMARY OF THE INVENTION

In one aspect, the present disclosure provides morphic Form I of marizomib, characterized by an X-ray powder diffraction pattern including peaks at about 7.2, 14.5, and 36.7°2θ using Cu Kα radiation.

In another aspect, the present disclosure provides a pharmaceutical composition comprising a morphic Form of marizomib (e.g., Form I) and a pharmaceutically acceptable carrier.

In another aspect, the present disclosure provides a method of treating a disease comprising administering to a subject in need thereof an effective amount of a morphic Form of marizomib (e.g., morphic Form I).

In another aspect, the present disclosure provides a morphic Form of marizomib (e.g., morphic Form I) for use in the treatment of a disease.

In another aspect, the present disclosure provides a morphic Form of marizomib (e.g., morphic Form I) for inhibiting a proteases.

In another aspect, the present disclosure provides the use of a morphic form of marizomib (e.g., morphic Form I) in the manufacture of a medicament for the treatment of a disease.

In another aspect, the present disclosure provides a method of preparing a morphic form of marizomib (e.g., morphic Form I) comprising recrystallizing marizomib from a solvent.

BRIEF DESCRIPTION OF THE FIGURES

FIG. 20 shows a differential scanning calorimetry plot of Sample 3 of Morphic Form I of marizomib at 50° C. per minute.

DETAILED DESCRIPTION OF THE INVENTION

Figure 1:
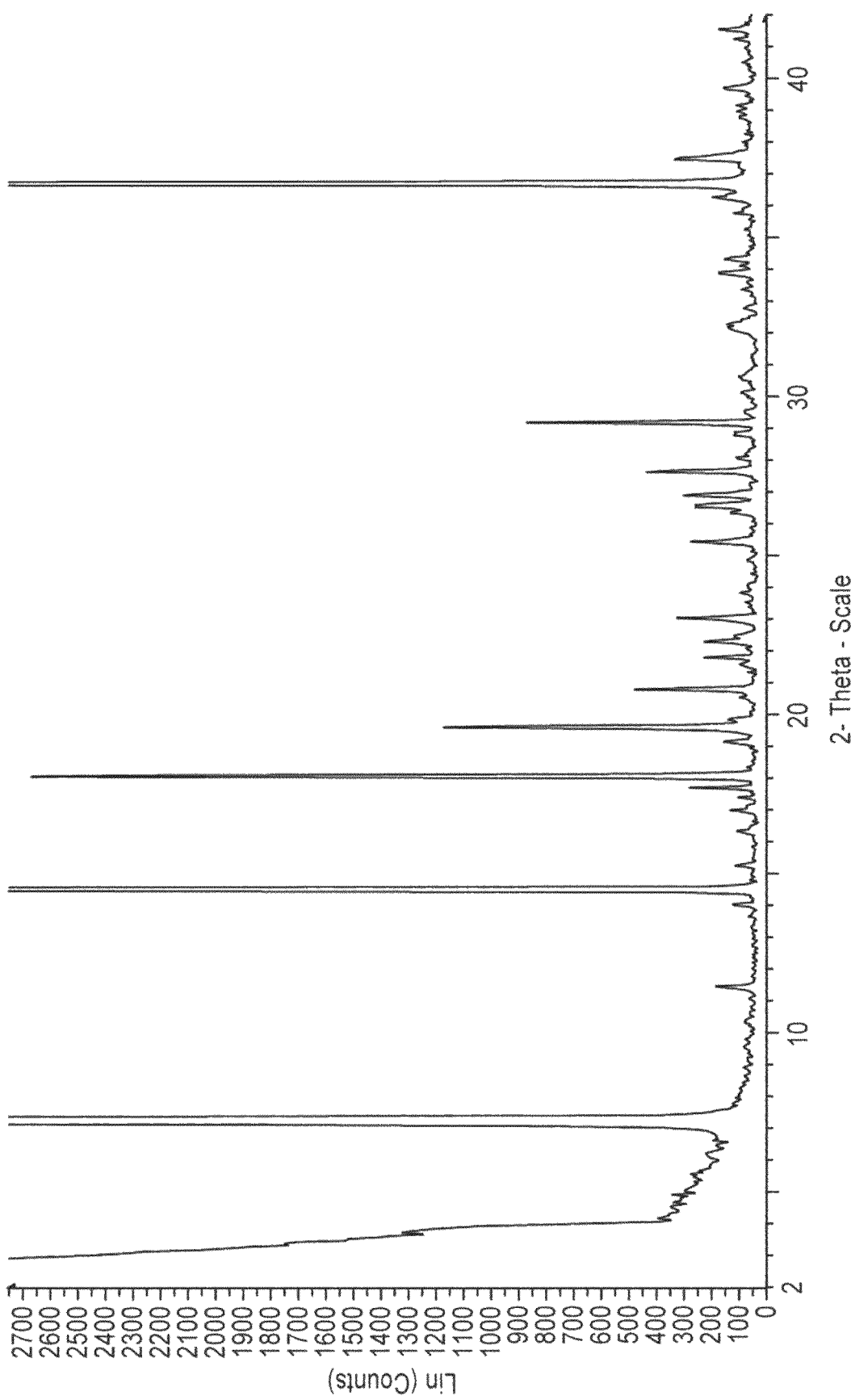
FIG. 1 shows an XRPD spectrum of a Sample 1 of Morphic Form I of marizomib.

The present disclosure relates to morphic Forms (e.g., Form I) of marizomib. The morphic Forms can be solvates or hydrates.

As defined herein "pure" is understood to mean that a compound is uniform in chemical makeup. It is understood that a pure compound does not contain molecules of another chemical makeup in an appreciable amount, e.g., less than 5%, less than 4%, less than 3%, less than 2%, or less than 1%. In some instances, the purity is measured excluding any solvent (e.g., organic solvent such as ethyl acetate, and inorganic solvent such as water). Purity can be measured by a number of techniques known in the art, for example HPLC.

In some embodiments, the morphic forms of marizomib are substantially pure. For example, the morphic forms described herein (e.g., morphic Form I) can be greater than about 90% pure, greater than about 91% pure, greater than about 92% pure, greater than about 93% pure, greater than about 94% pure, greater than about 95% pure, greater than about 96% pure, greater than about 97% pure, greater than about 98% pure, greater than about 99% pure, or greater than about 99.9% pure.

As defined herein, "stable" or "stability" relates to the ability of a compound to remain pure for a period of time. A stable compound can be one that maintains its purity (e.g., does not have molecules of an undesired chemical formula) despite extended storage (e.g., greater than one month, greater than six months, or greater than a year). A stable compound can also be a compound that remains pure despite conditions such as high temperature or humidity.

In some embodiments, the morphic forms of marizomib described herein retain their purity for extended periods of time (i.e., are stable). In some embodiments, the morphic Forms described herein (e.g., morphic Form I) can retain at least 99% purity for one month, for two months, for three months, for four months, for five months, for six months, for 12 months, for 24 months, for 36 months, for 48 months, or for 60 months or more.

Without wishing to be bound by theory, chemical compounds are known to exist in multiple different polymorphic forms. Accordingly, one of skill in the art would expect that marizomib can potentially exist in multiple different morphic forms, in addition to the amorphous form. Surprisingly, the present disclosure teaches that marizomib exists primarily in one morphic form (i.e., morphic Form I). The present disclosure teaches that morphic Form I is particularly stable.

Morphic Form I of Marizomib

Marizomib is a proteasome inhibitor with the structure:

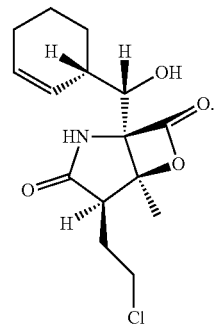

In some embodiments, morphic Form I of marizomib is characterized by an X-ray diffraction pattern including peaks at about 7.2, 14.5, and 36.7°2θ using Cu Kα radiation. In some embodiments, morphic Form I is further characterized by X-ray powder diffraction peaks at about 18.1, 19.6, and 20.8°2θ using Cu Kα radiation. In some embodiments, morphic Form I of marizomib is further characterized by X-ray powder diffraction peaks at about 16.3, 19.8, and 20.5°2θ using Cu Kα radiation. In some embodiments, morphic Form I of marizomib is further characterized by X-ray powder diffraction peaks at about 15.2, 21.5, and 22.3°2θ using Cu Kα radiation. In some embodiments, morphic Form I of marizomib is further characterized by X-ray powder diffraction peaks at about 14.7, 29.2, and 30.0°2θ using Cu Kα radiation. In some embodiments, morphic Form I of marizomib is further characterized by X-ray powder diffraction peaks at about 8.2, 14.8, and 27.7°2θ using Cu Kα radiation. In some embodiments, morphic Form I of marizomib is free of solvent (e.g., water or organic solvent).

In some embodiments, morphic Form I of marizomib is further characterized by an X-ray powder diffraction pattern substantially similar to that set forth in FIG. 1. In some embodiments, morphic Form I of marizomib is further characterized by an X-ray powder diffraction pattern substantially similar to that set forth in FIG. 2. In some embodiments, morphic Form I of marizomib is further characterized by an X-ray powder diffraction pattern substantially similar to that set forth in FIG. 3. In some embodiments, morphic Form I of marizomib is further characterized by a degradation event at about 175° C. measured by thermogravimetric analysis.

In some embodiments, morphic Form I of marizomib is further characterized by two exotherms at about 150-180° C. as measured by differential scanning calorimetry at a rate of about 2° C. per minute. For example, morphic Form I can be characterized by two exotherms at about 155-175° C.

In some embodiments, morphic Form I of marizomib is characterized by an endotherm at about 168.5° C. and an exotherm at about 173-183° C., as measured by differential scanning calorimetry at a rate of about 5° C. per minute.

In some embodiments, morphic Form I of marizomib is characterized by two endotherms at about 175.5° C. and 180.6° C. and an exotherm at about 183-193° C.; or characterized by two endotherms at about 171.2° C. and 178.6° C. and an exotherm at about 183-193° C., as measured by differential scanning calorimetry at a rate of about 10° C. per minute.

In some embodiments, morphic Form I of marizomib is characterized by two endotherms at about 186.5° C. and 192.6° C. and an exotherm at about 193-205° C.; or characterized by two endotherms at about 180.9° C. and 191.6° C. and an exotherm at about 193-205° C. as measured by differential scanning calorimetry at a rate of about 50° C. per minute.

In some embodiments, morphic Form I of marizomib is characterized by melting and/or degradation at about 160-175° C. as measured by hot stage microscopy.

In some embodiments, morphic Form I of marizomib is at least about 98% pure as measured by HPLC. For example, the morphic Form can be at least about 99.1% pure as measured by HPLC.

As set forth in the present disclosure, three unique samples of morphic Form 1 of marizomib were characterized, Sample 1, Sample 2, and Sample 3. Samples 1 and 2 are not micronized, whereas Sample 3 was micronized. X-ray powder diffraction spectra measurements for Samples 1, 2 and 3 are given in Tables 1, 2 and 3, respectively. As set forth herein, both the micronized and the non-micronized samples are the same morphic form (i.e., morphic Form I).

TABLE 1

XRPD: Form I Sample 1

| Pos. [° 2θ] | Rel. Int [%] |
| --- | --- |
| 7.2 | 100.0 |
| 11.4 | 0.1 |
| 14.0 | 0.1 |
| 14.5 | 6.4 |
| 17.7 | 0.2 |
| 18.0 | 2.0 |
| 19.1 | 0.1 |
| 19.6 | 0.9 |
| 20.8 | 0.4 |
| 21.8 | 0.2 |
| 22.3 | 0.2 |
| 23.0 | 0.3 |
| 25.4 | 0.2 |
| 26.6 | 0.2 |
| 26.9 | 0.2 |
| 27.6 | 0.3 |
| 29.2 | 0.7 |
| 36.7 | 4.3 |
| 37.5 | 0.3 |

TABLE 2

XRPD: Form I Sample 2

| Pos. [°2θ] | Rel. Int. [%] |
| --- | --- |
| 7.2 | 100.0 |
| 11.5 | 0.3 |
| 14.0 | 0.2 |
| 14.5 | 5.2 |
| 17.7 | 0.2 |
| 18.1 | 2.6 |
| 19.1 | 0.3 |
| 19.6 | 2.2 |
| 20.8 | 0.7 |
| 22.3 | 0.4 |
| 23.1 | 0.4 |
| 25.5 | 0.4 |
| 26.6 | 0.5 |
| 26.9 | 0.4 |
| 27.7 | 0.5 |
| 29.2 | 0.6 |
| 36.7 | 4.9 |
| 37.5 | 0.5 |

TABLE 3

XRPD: Form I Sample 3

| Pos. [°2θ] | Rel. Int. [%] |
| --- | --- |
| 7.2 | 100.0 |
| 8.2 | 4.2 |
| 10.2 | 2.4 |
| 11.4 | 2.2 |
| 13.7 | 2.0 |
| 14.5 | 7.7 |
| 14.7 | 5.6 |
| 14.8 | 3.6 |
| 15.2 | 6.0 |
| 16.3 | 9.3 |
| 18.1 | 18.0 |
| 19.1 | 3.2 |
| 19.6 | 16.3 |
| 19.8 | 11.9 |
| 20.5 | 6.6 |
| 20.8 | 5.6 |
| 21.5 | 6.2 |
| 22.1 | 2.8 |
| 22.3 | 6.3 |
| 23.0 | 2.6 |
| 23.9 | 3.4 |
| 25.4 | 2.7 |
| 26.5 | 3.4 |
| 26.9 | 2.5 |
| 27.7 | 4.3 |
| 28.8 | 3.3 |
| 29.2 | 4.6 |
| 29.5 | 3.4 |
| 30.0 | 4.5 |
| 32.3 | 3.3 |
| 36.7 | 4.6 |

Figure 2:
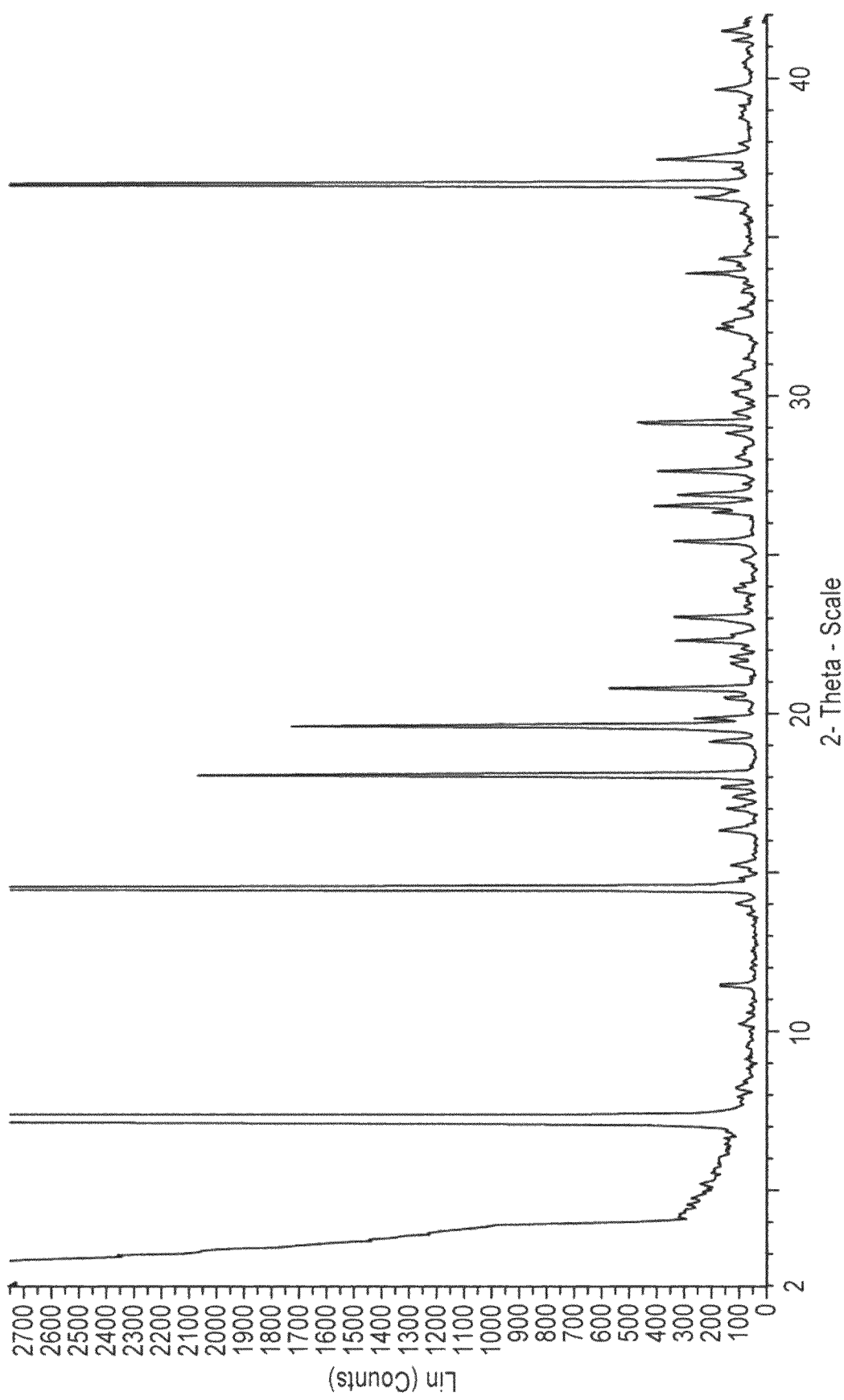
FIG. 2 shows an XRPD spectrum of a Sample 2 of Morphic Form I of marizomib.
Figure 3:
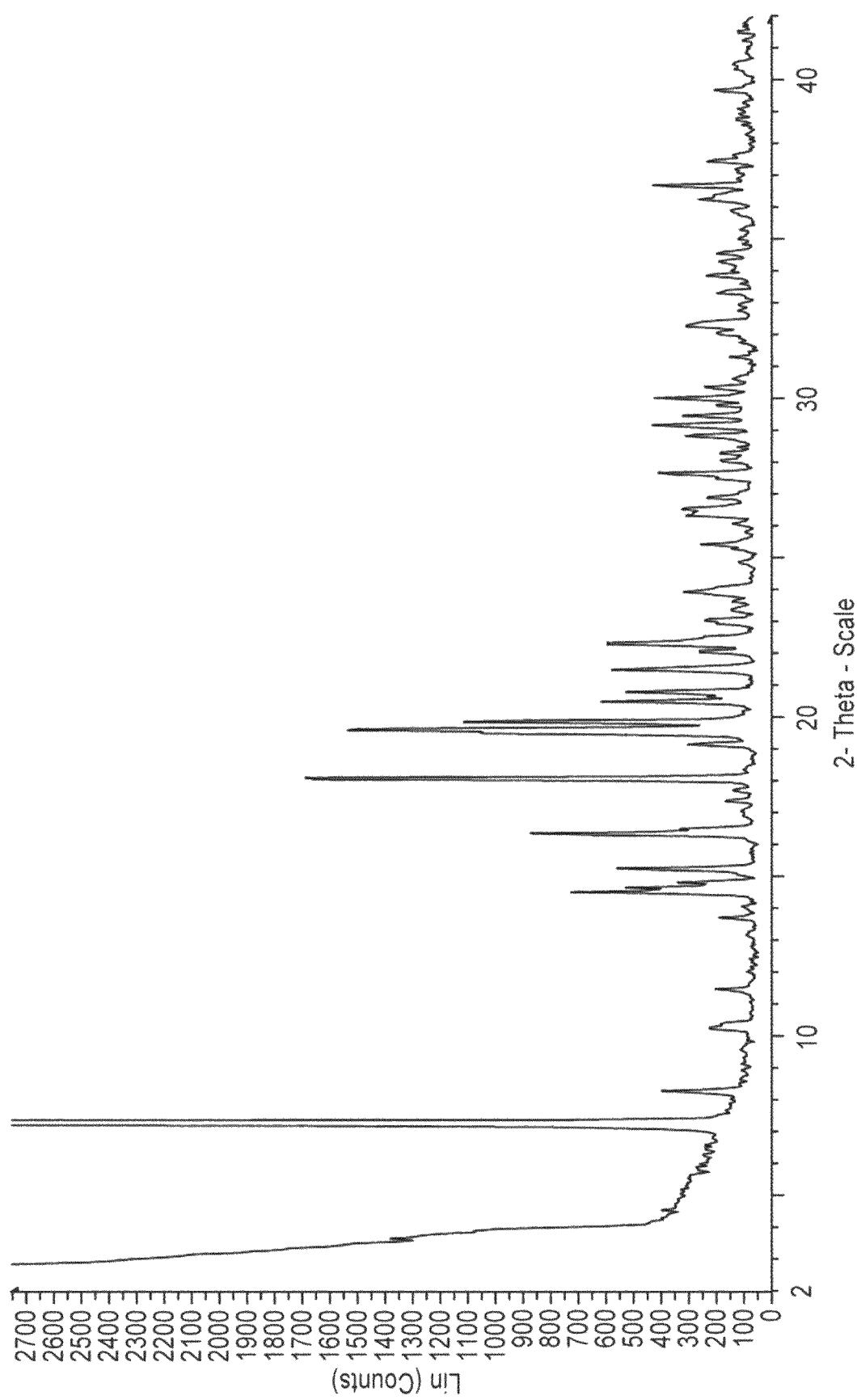
FIG. 3 shows an XRPD spectrum of a Sample 3 of Morphic Form I of marizomib.

FIG. 1 shows an XRPD spectrum of Sample 1 of morphic Form I of marizomib. As set forth in FIG. 1, the XRPD spectrum includes peaks at about 7.2, 14.5, and 36.70°2θ. FIG. 2 shows an XRPD spectrum of Sample 2 of morphic Form I of marizomib. As set forth in FIG. 2, the XRPD spectrum includes peaks at about 7.2, 14.5, and 36.7°2θ. FIG. 3 shows an XRPD spectrum of Sample 3 of morphic Form I of marizomib. As set forth in FIG. 3, the XRPD spectrum includes peaks at about 7.2, 14.5, and 36.7°2θ.

Figure 4:
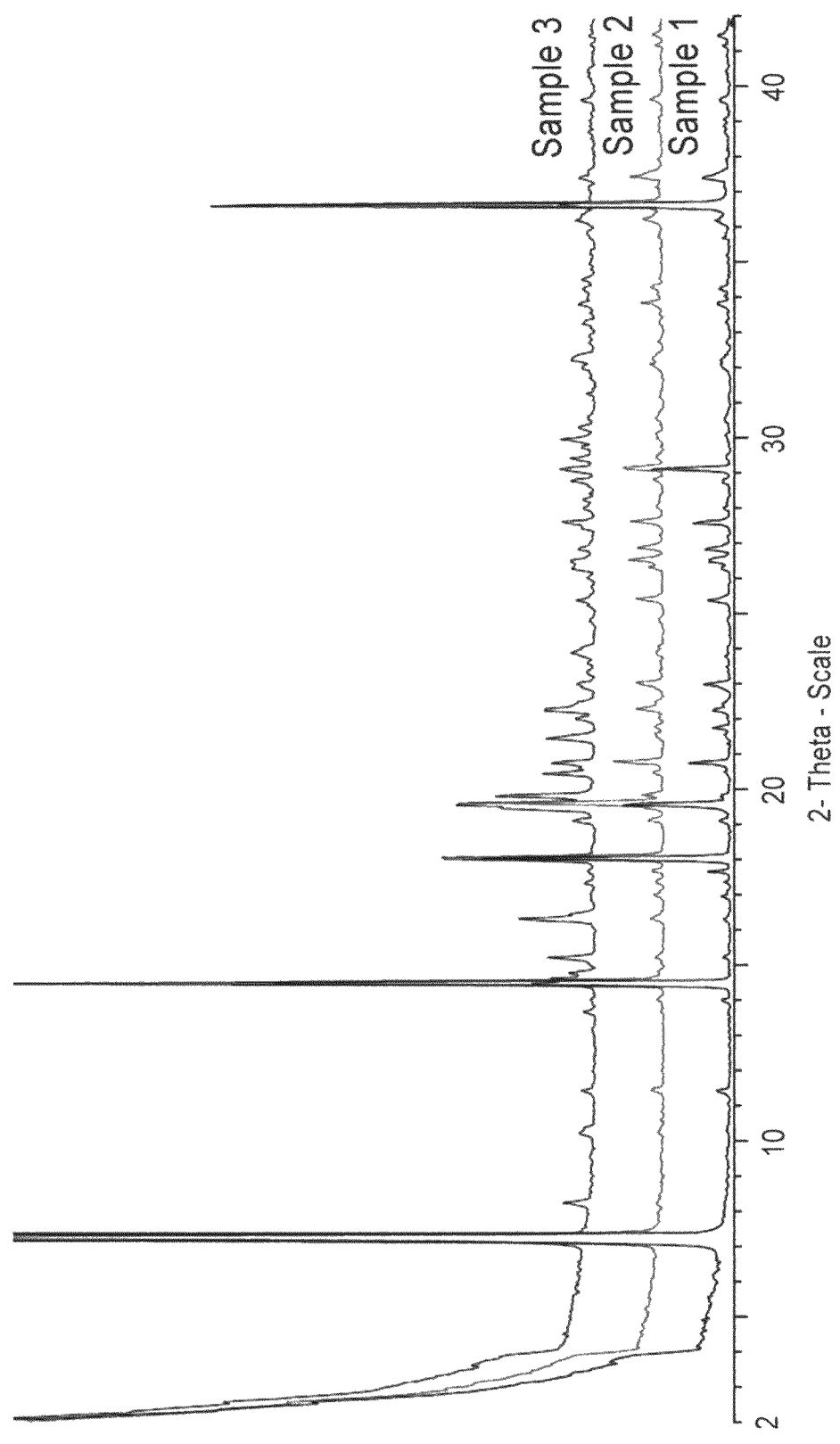
FIG. 4 shows an overlay of all three XRPD spectra of Samples 1, 2 and 3 of Form I of marizomib.

FIG. 4 shows an overlay of the three XRPD spectra of FIGS. 1, 2 and 3 (i.e., Samples 1, 2 and 3). As shown in FIG. 4, there can be slight differences between the XRPD spectra of even the same morphic form (i.e., morphic Form I) of marizomib. For example, certain peaks may be more or less pronounced (e.g., smaller or larger) in one spectrum compared with another.

As shown in the tables and figures of the present application, not all values for peaks (pos. °2θ) are identical for different lots of the polymorphs of the present application. An artisan of ordinary skill will understand that even different lots of the same polymorphic forms can produce slightly different characterization data, while not being appreciably different. For instance, slight variations in the calibration of the instruments used to perform a given measurement, or minor fluctuations in relative humidity between measurements can give rise to data that displays slight differences between samples. One of ordinary skill in the art will thus be able to, for instance, calibrate his or her instruments and take repeated measurements in order to minimize any discrepancies between signals to properly characterize the polymorphs of the present application. However, despite some minor variation in the batch-to-batch differences, polymorphs of the present application are identified and characterized by their characteristic peaks, such as those described above (e.g., about 7.2, 14.5, and 36.7°2θ, ±0.2°2θ).

In some embodiments, differences in XRPD spectra (e.g., resolution) can be attributed to preferred orientation. Without wishing to be bound by theory, in XRPD it can be desirable to have a sample in which particles are oriented randomly (e.g., a powder). However, it can be difficult or in some cases impossible to achieve truly random particle orientations in practice. As particle size increases, the randomness of particle orientation can decrease, leading to increased challenges with achieving a preferred orientation.

Without wishing to be bound by theory, larger particles that do not exhibit random orientations can result in XRPD spectra in which some peaks are either diminished in intensity or in some embodiments missing altogether. Accordingly, in some embodiments micronized samples (e.g., Sample 3) can facilitate more random orientation of particles and thus a more accurate XRPD spectrum. In some embodiments a micronized sample with more randomness in particle orientation results in an XRPD spectrum with more peaks. In contrast, samples with larger particles (e.g., Sample 1, Sample 2) can lead to XRPD spectra with less pronounced peaks and in some embodiments fewer peaks.

Figure 5:
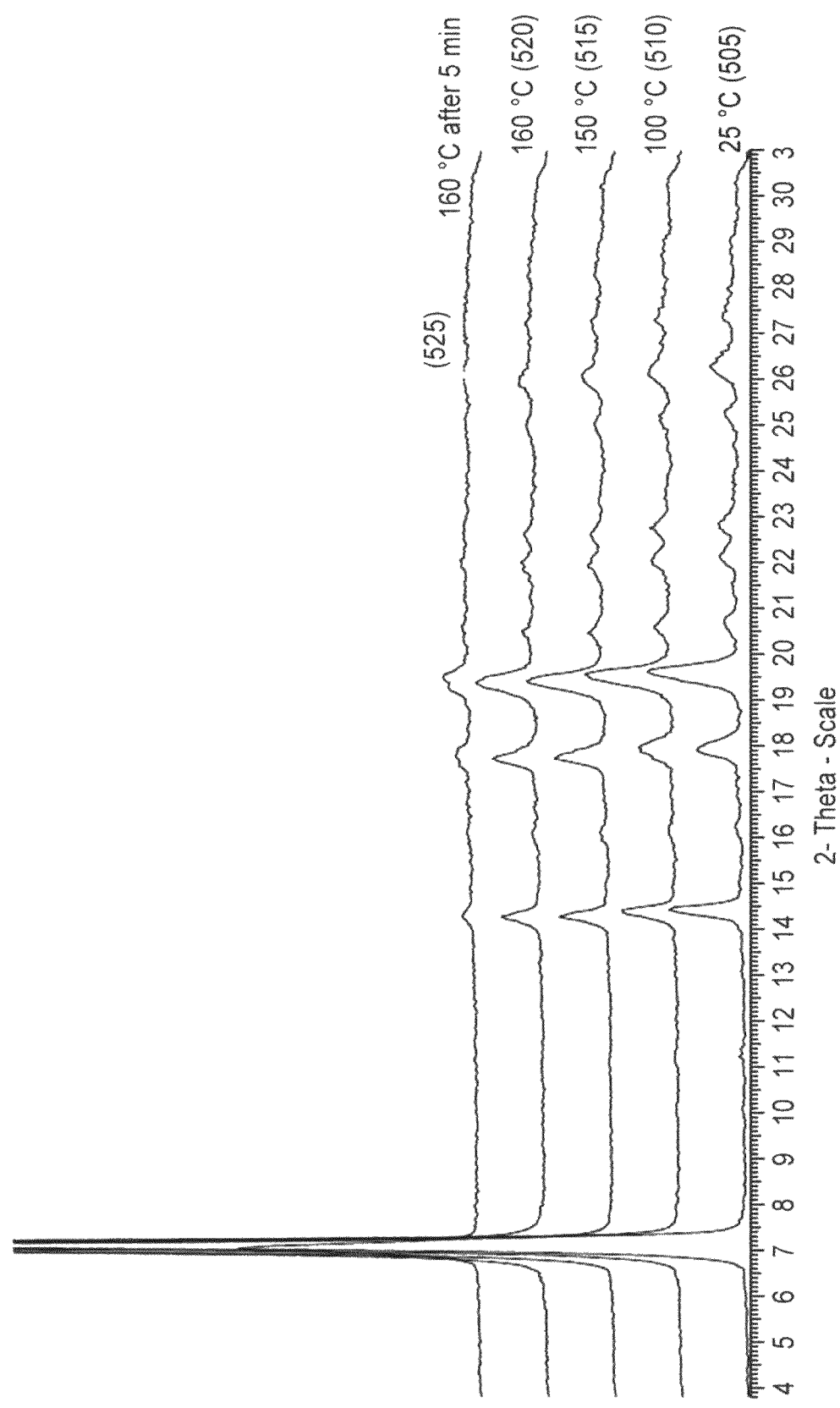
FIG. 5 shows a plot of variable temperature XRPD spectra of Sample 1 of Morphic Form I of marizomib.

As set forth in FIG. 5, morphic Form I of marizomib is stable even at elevated temperatures. FIG. 5 shows five unique XRPD spectra of sample 1 of morphic Form I of marizomib. The lowest trace (505) shows an XRPD spectrum at 25° C. Above that trace is the same sample at 100° C. (510). Shown above is another trace at 150° C., (515) then at 160° C. (520), and finally the highest trace shows an XRPD spectrum of the sample after five minutes at 160° C. (525).

Figure 6:
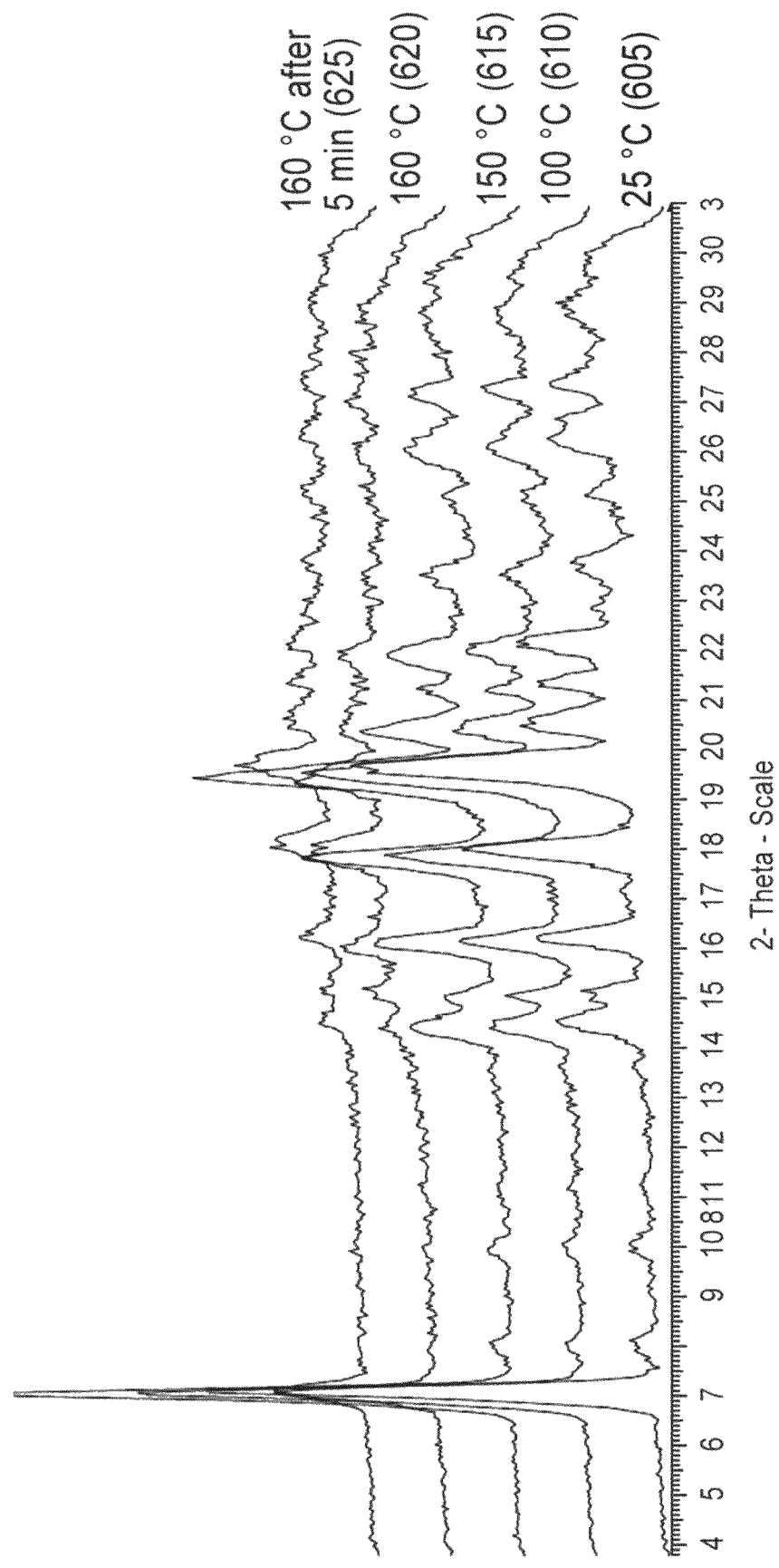
FIG. 6 shows a plot of variable temperature XRPD spectra of Sample 3 of Morphic Form I of marizomib.

Additionally, FIG. 6 shows five unique XRPD spectra of sample 3 of morphic Form I of marizomib at different temperatures. The lowest (605) is an XRPD spectrum of Sample 3 at 25° C., and also shown are traces at 100° C. (610), 150° C. (615), 160° C. (620), and 160° C. after five minutes (625). As set forth in FIGS. 5 and 6, only one morphic form (i.e., Form I) of marizomib was observed even as the temperature increased. Without wishing to be bound by theory, this suggests that Form I is the major morphic Form of marizomib. Without wishing to be bound by theory, this also suggests that Form I is the most stable morphic form of marizomib.

Figure 7:
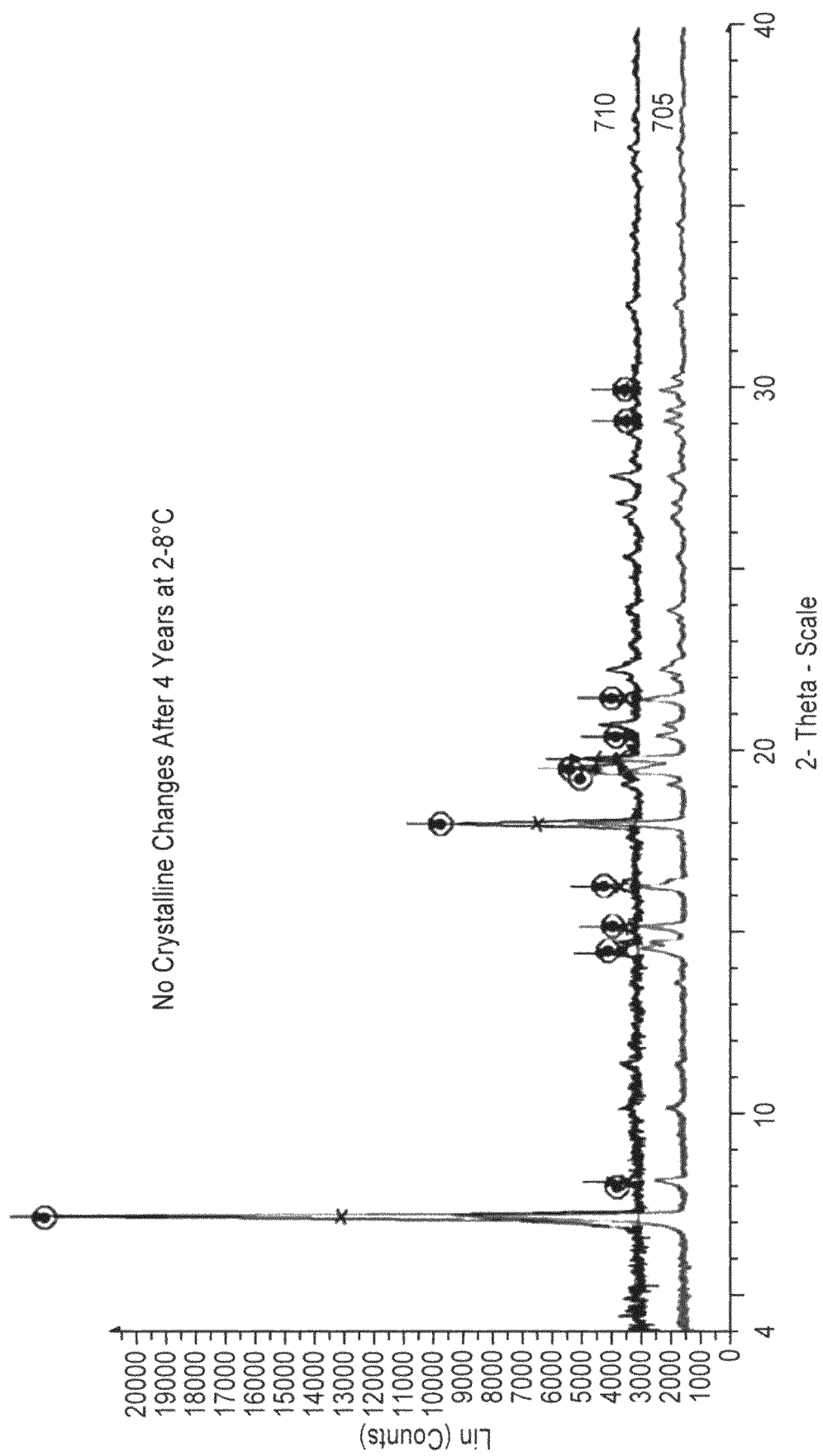
FIG. 7 shows an overlay of two XRPD spectra of marizomib after four years of storage at 2-8° C.

Without wishing to be bound by theory, the results of FIGS. 5 and 6 are further supported by FIG. 7. FIG. 7 shows an overlay of the same sample of morphic Form I of marizomib initially (705) and after storage for four years at 2-8° C. (710). The XRPD spectra are substantially identical, demonstrating that morphic Form I is stable at low temperatures for extended periods of time.

Figure 8:
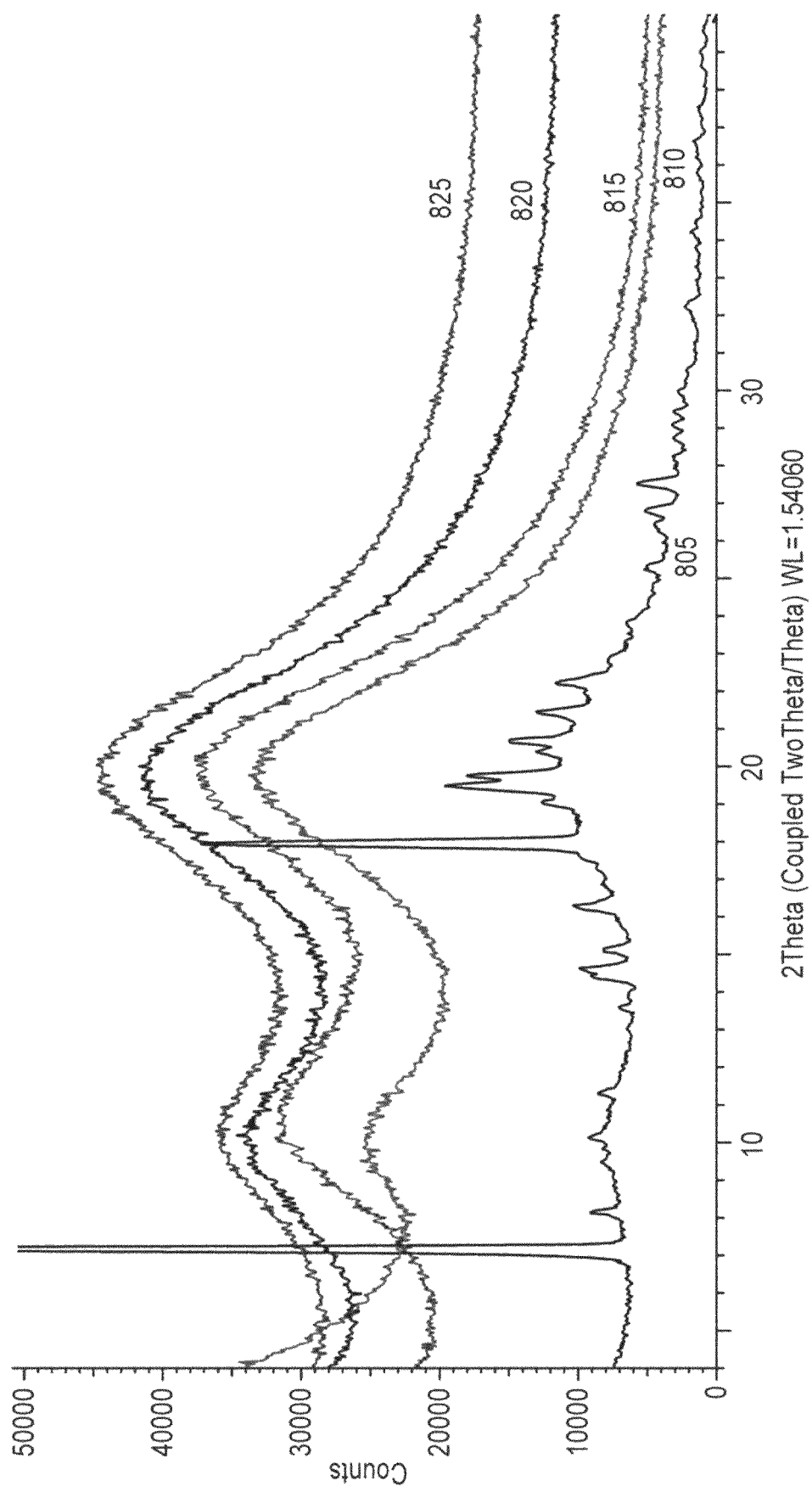
FIG. 8 shows an overlay of five XRPD spectra contrasting the XRPD spectra of Form I of marizomib with amorphous forms of marizomib.

FIG. 8 shows an overlay of five XRPD spectra of marizomib. Form I of marizomib is shown in trace 805, whereas marizomib that has been co-spray dried with polymers are shown in traces 810, 815, 820, and 825. Trace 810 shows an XRPD spectrum of marizomib that has been co-spray dried with hydroxypropyl methylcellulose. Trace 815 shows an XRPD spectrum of marizomib that has been co-spray dried with polyvinylpyrrolidone. Trace 820 shows an XRPD spectrum of marizomib that has been co-spray dried with hydroxypropyl methylcellulose acetate succinate-M. Trace 825 shows an XRPD spectrum of marizomib that has been co-spray dried with hydroxypropyl methylcellulose acetate succinate-L.

Pawley fitting is a process in which observed peaks in a powder pattern can be fitted without a structural model but at 2θ values constrained by the size and symmetry of the unit cell. In some embodiments, it can be a useful precursor to Rietveld fitting and can give an indication of the "best fit possible" from an eventual structural refinement. This fitting method was applied to XRPD diffractograms of the micronized and non-micronized supplied materials, Sample 3 and Sample 1, respectively.

Marizomib crystallizes in the monoclinic space group, P21, with these unit cell parameters:

$$a=10.57 \text{ Å}, b=24.49 \text{ Å } c=12.63 \text{ Å and } \beta=108.34°$$

Without wishing to be bound by theory, fitting the two samples showed good correlation between calculated and observed profiles, with only very slight differences in peak shape and intensity. Sample 1 exhibited strong preferred orientation (crystals were of lath morphology) as opposed to the micronized Sample 3. As such, without wishing to be bound by theory, the micronized sample (Sample 3) appeared to display numerous peaks that were not visible in the non-micronized sample (Sample 1).

Without wishing to be bound by theory, the average particle size of particles of Sample 1 (i.e., non-micronized) was about 150 μm to about 300 μm, compared with an average sample size of about 1 μm to about 20 μm for the micronized Sample 3. Without wishing to be bound by theory, the smaller particle size in Sample 3 reduce technical challenges associated with preferred orientation and allows for more accurate representation of peaks. For example, Sample 1, Sample 2, and Sample 3 all show an XRPD peak at about 36.7°2θ, at intensities of 4.3, 4.9, and 4.6, respectively. However, the peak appears larger in Samples 1 and 2 because of the preferred orientation of the sample.

Figure 9:
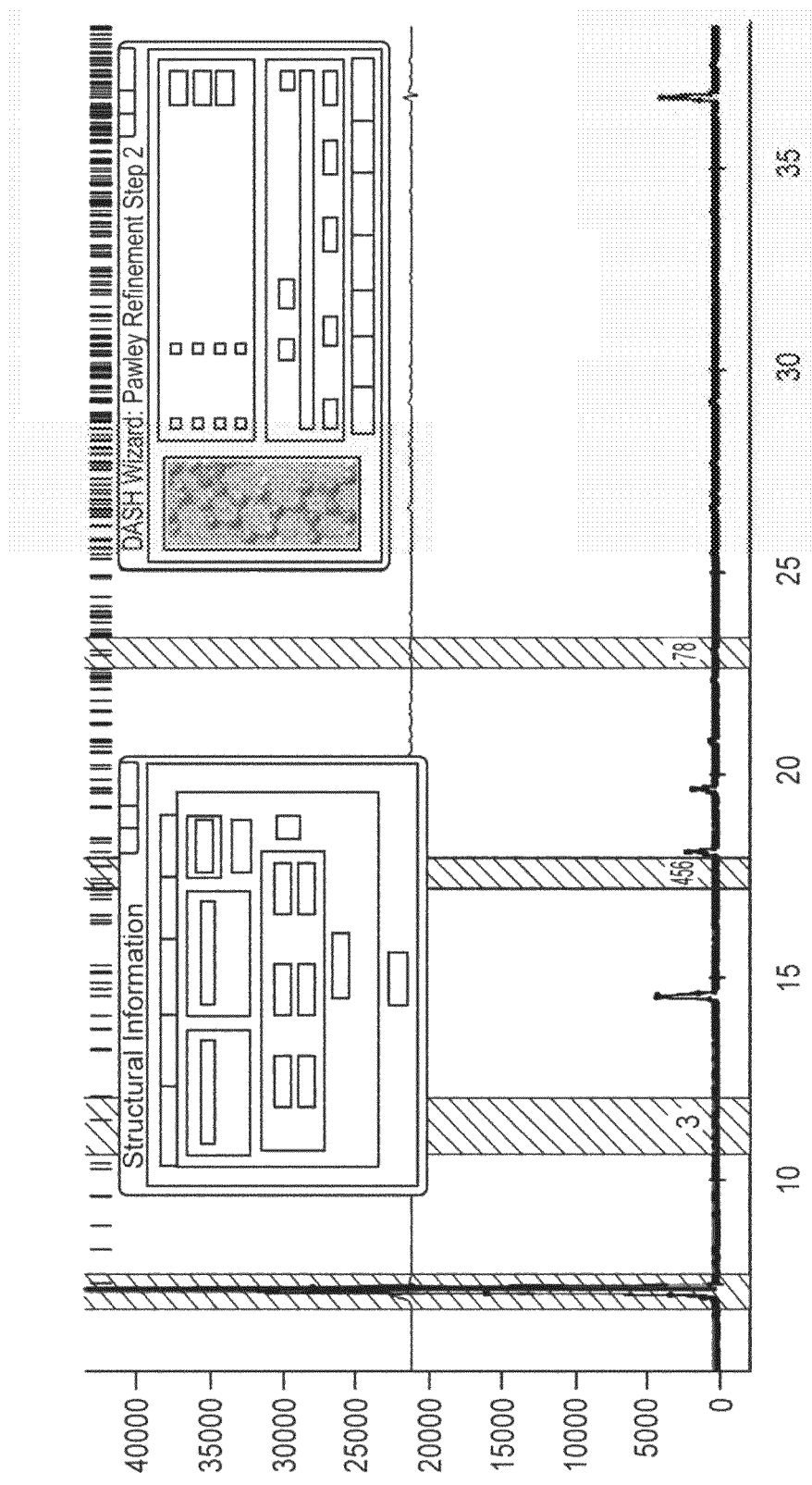
FIG. 9 shows an XRPD spectrum of a Pawley fitting procedure for Sample 1 of Morphic Form I of marizomib.
Figure 10:
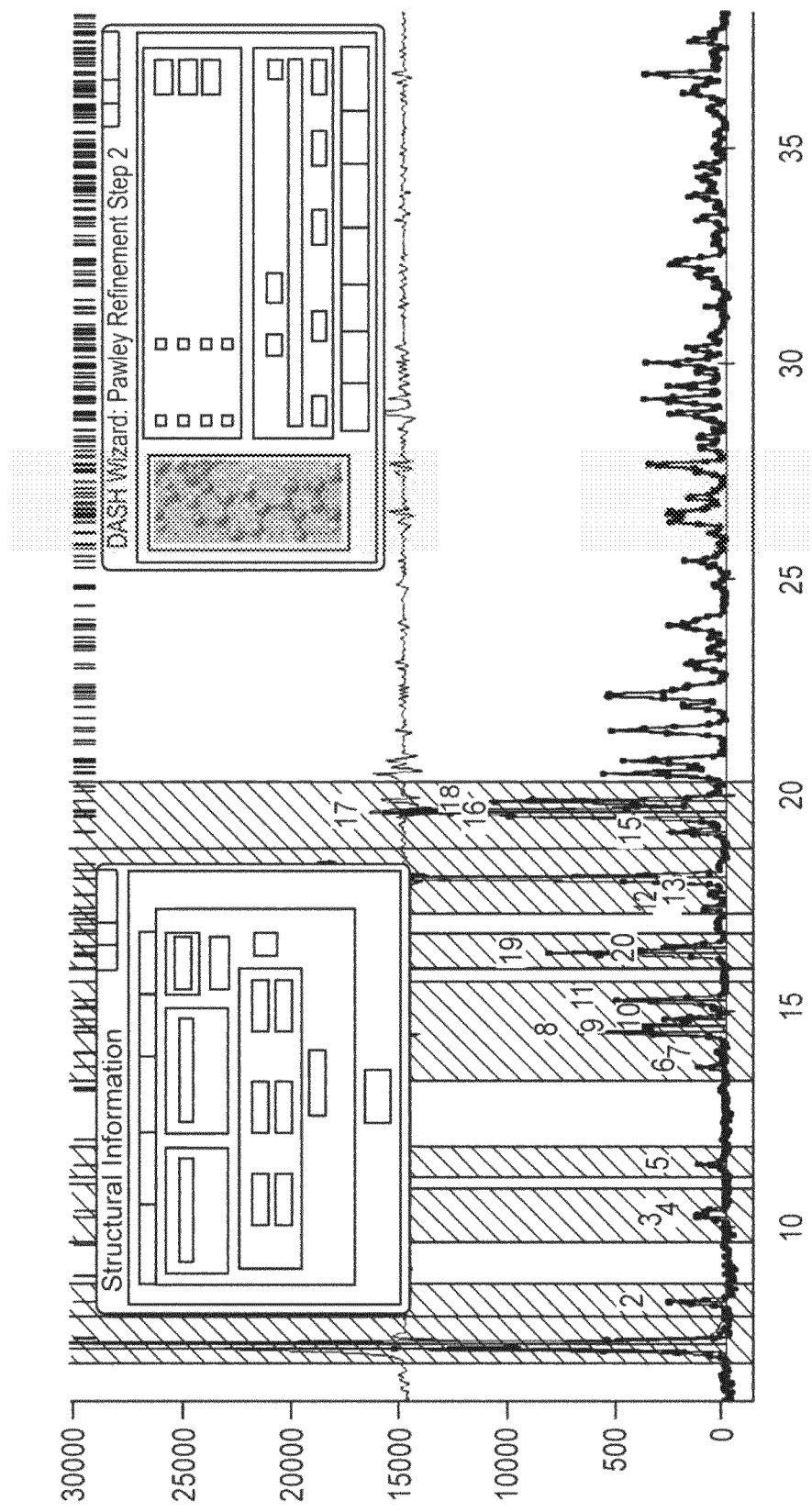
FIG. 10 shows an XRPD spectrum of a Pawley fitting procedure for Sample 3 of Morphic Form I of marizomib.

The Pawley fitting procedure can enable visualization of the presence or absence of a different phase. The peak at about 8°2θ, on the micronized sample (i.e., Sample 3) diffractogram was found to be also present in the non-micronized sample (Sample 1) diffractogram, as seen in the FIGS. 9-10. FIG. 9 shows an XRPD spectrum of a Pawley fitting procedure for Sample 1 of Morphic Form I of marizomib. FIG. 10 shows an XRPD spectrum of a Pawley fitting procedure for Sample 3 of Morphic Form I of marizomib. Without wishing to be bound by theory, these results suggest that the majority of the material from these two batches (i.e., Sample 1 and Sample 3) is representative of the single crystal data and any subtle difference between them is attributable to crystal morphology inducing preferred orientation.

Figure 11:
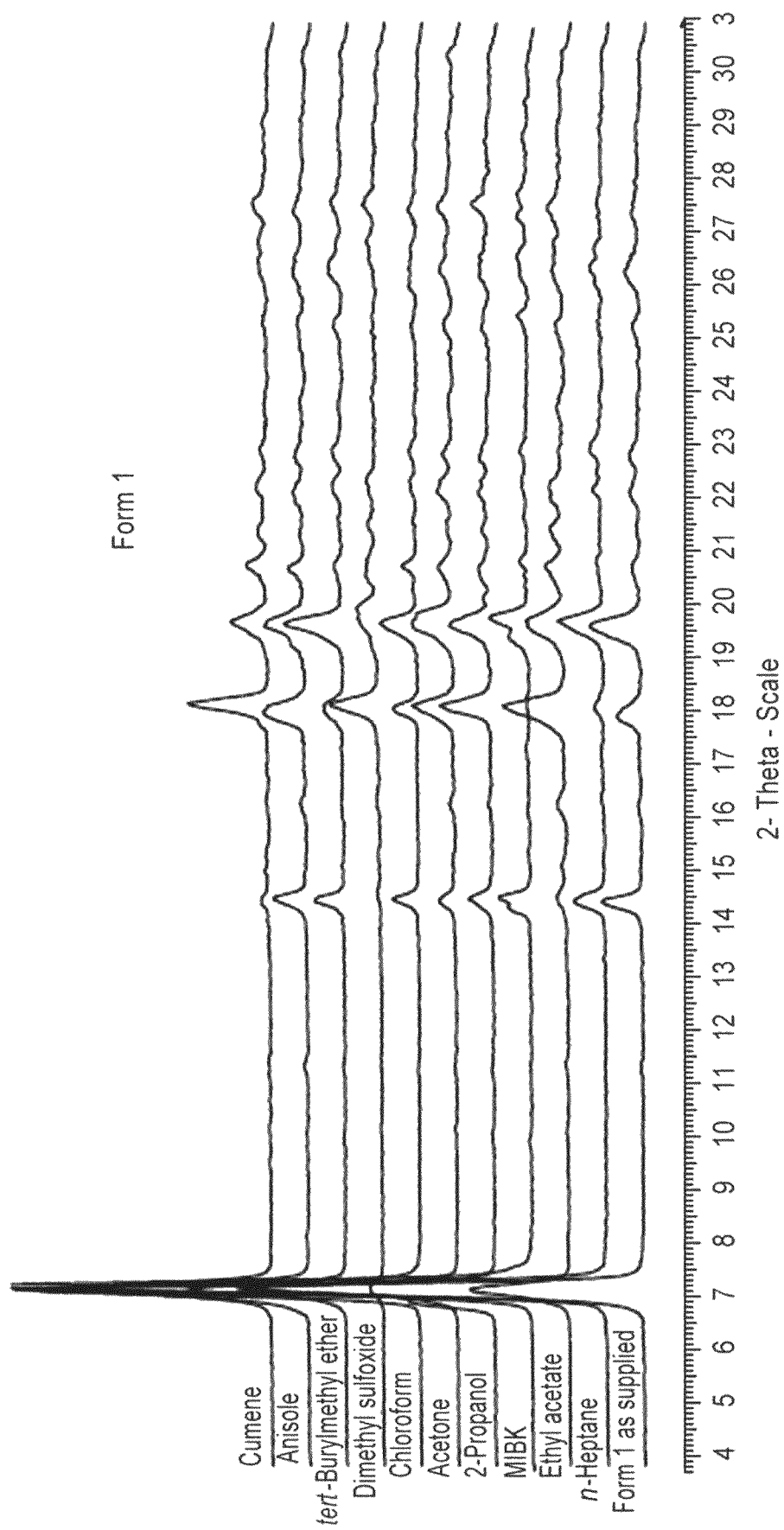
FIG. 11 shows an overlay of XRPD spectra from a polymorph screen.
Figure 12:
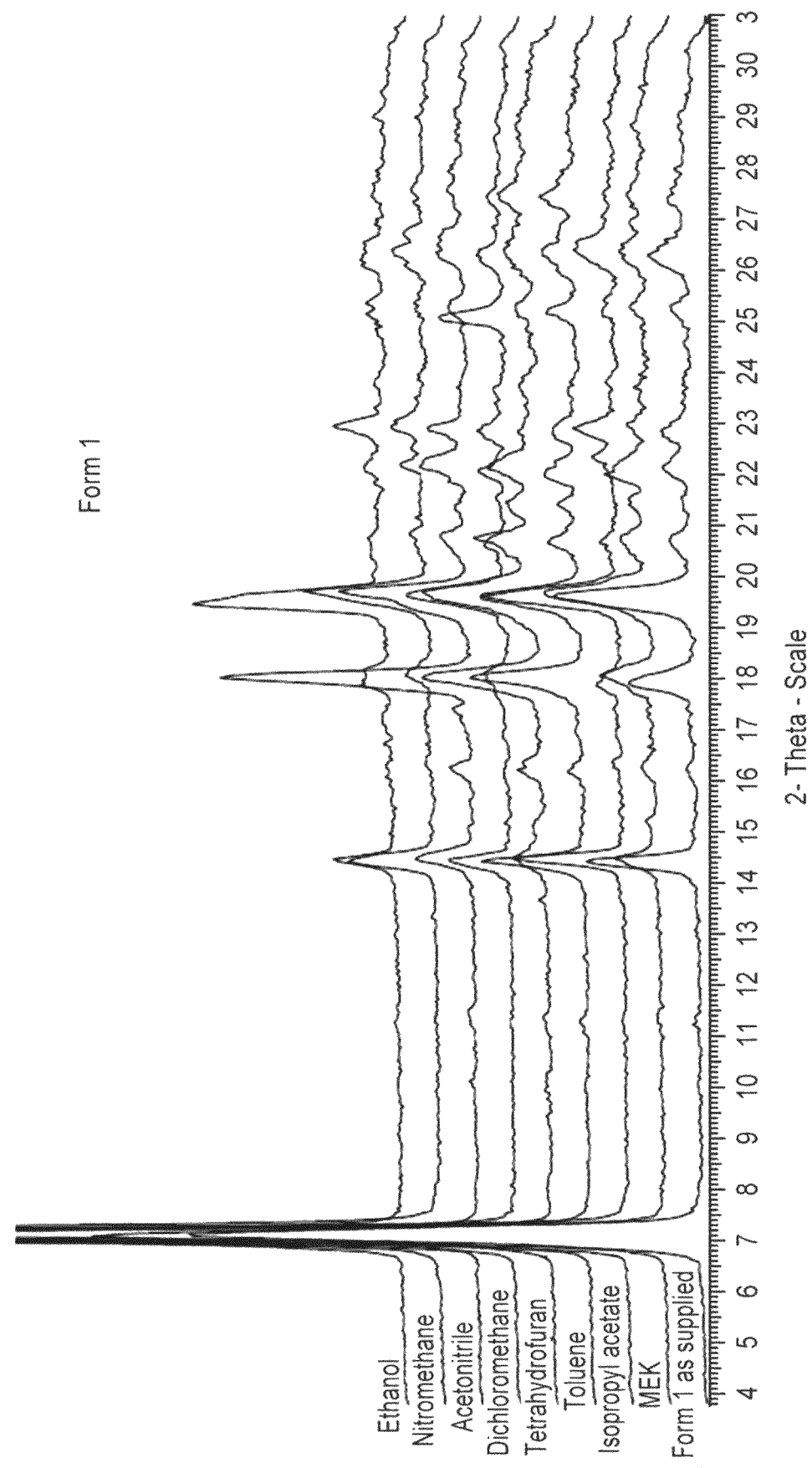
FIG. 12 shows an overlay of XRPD spectra from a polymorph screen.

FIGS. 11 and 12 show a overlays of XRPD spectra of the solids isolated from the polymorph screen set forth in Example 2 using the various solvents used in the screen. A solid was not obtained for two solvents (DMF and DMA) since marizomib remained in solution and did not precipitate, thus no XRPD pattern for DMF or DMA was obtained. The solvents are listed next to the corresponding spectra.

Figure 13:
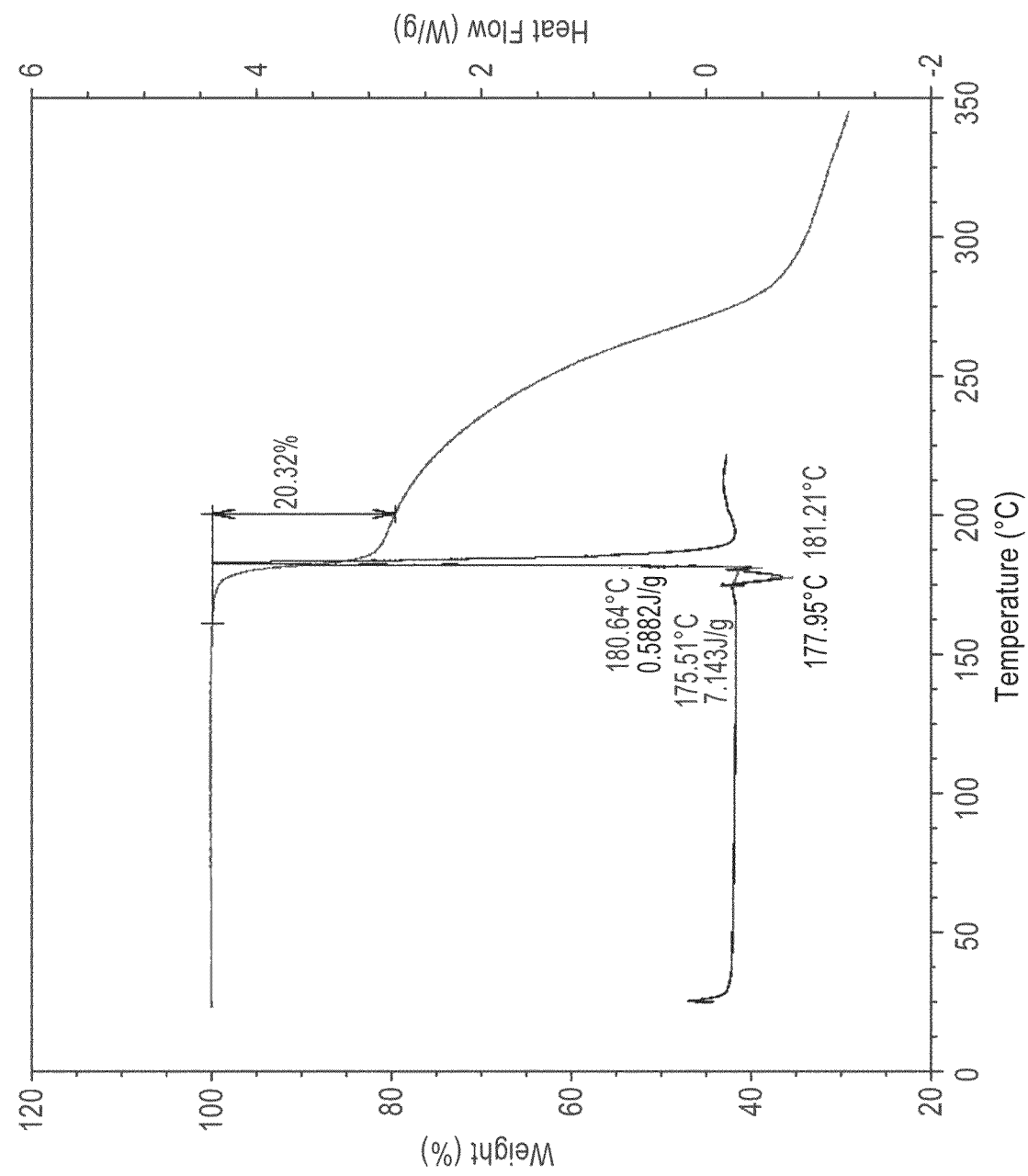
FIG. 13 shows a plot of a thermogravimetric analysis of Sample 1 of Morphic Form I of marizomib.

FIG. 13 shows a plot of a thermogravimetric analysis of Sample 1 of morphic Form I of marizomib. As shown in FIG. 13, no weight loss was observed until about 175° C. Without wishing to be bound by theory, this weight loss can be due to sample degradation.

Figure 14:
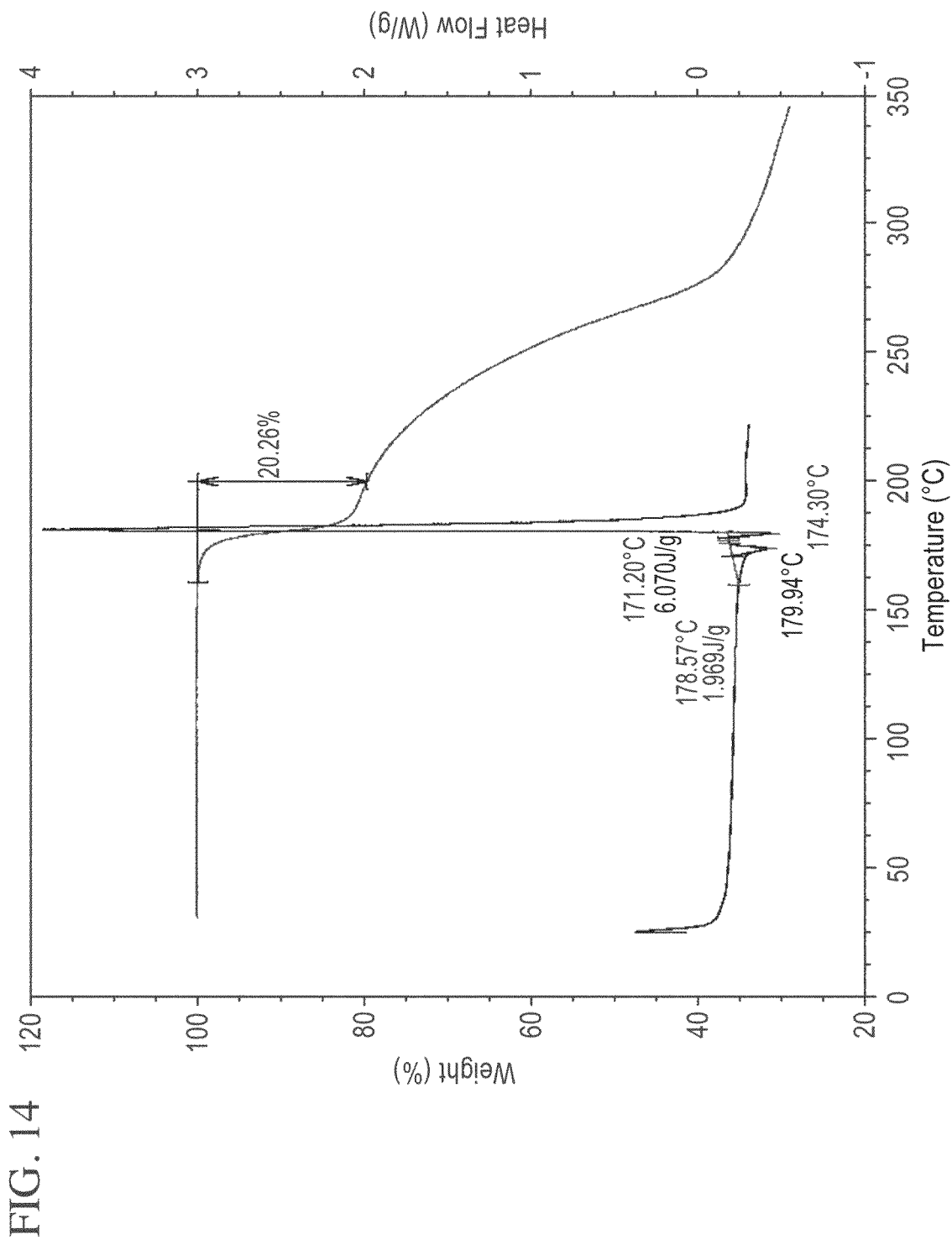
FIG. 14 shows a plot of a thermogravimetric analysis of Sample 3 of Morphic Form I of marizomib.

Similarly, FIG. 14 shows a plot of a thermogravimetric analysis of sample 3 of morphic Form I of marizomib. As shown in FIG. 14, no weight loss was observed until about 175° C. Without wishing to be bound by theory, this weight loss can be due to sample degradation.

Figure 15:
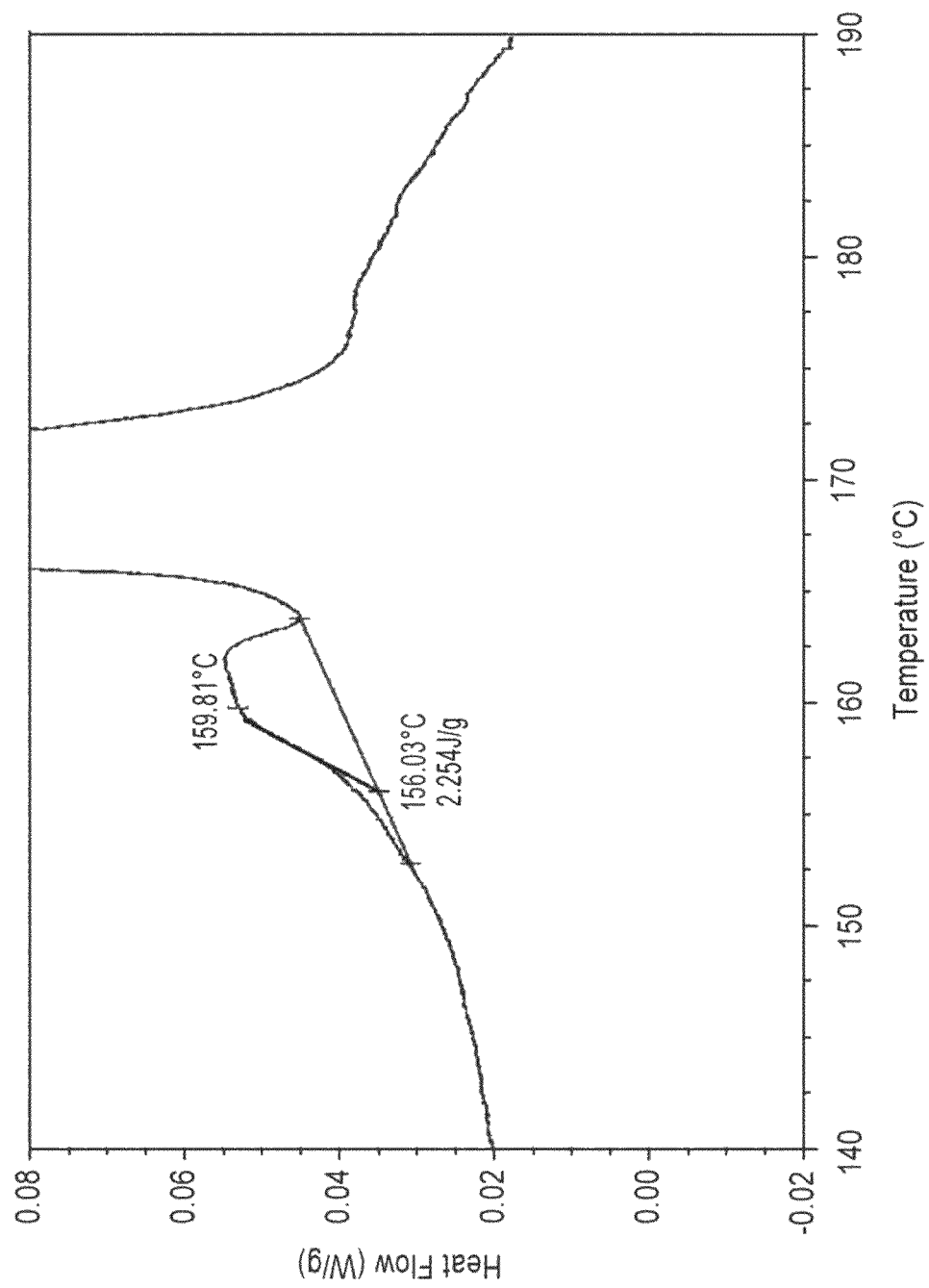
FIG. 15 shows a differential scanning calorimetry plot of Sample 1 of Morphic Form I of marizomib at 2° C. per minute.

FIG. 15 shows a differential scanning calorimetry plot of Sample 1 of Morphic Form I of marizomib at 2° C. per minute. As shown in FIG. 15, no endotherm was observed. Two exotherms were observed between about 150-180° C. The first exotherm was smaller than the second exotherm. Without wishing to be bound by theory, the exotherms could be due to sample degradation.

Figure 16:
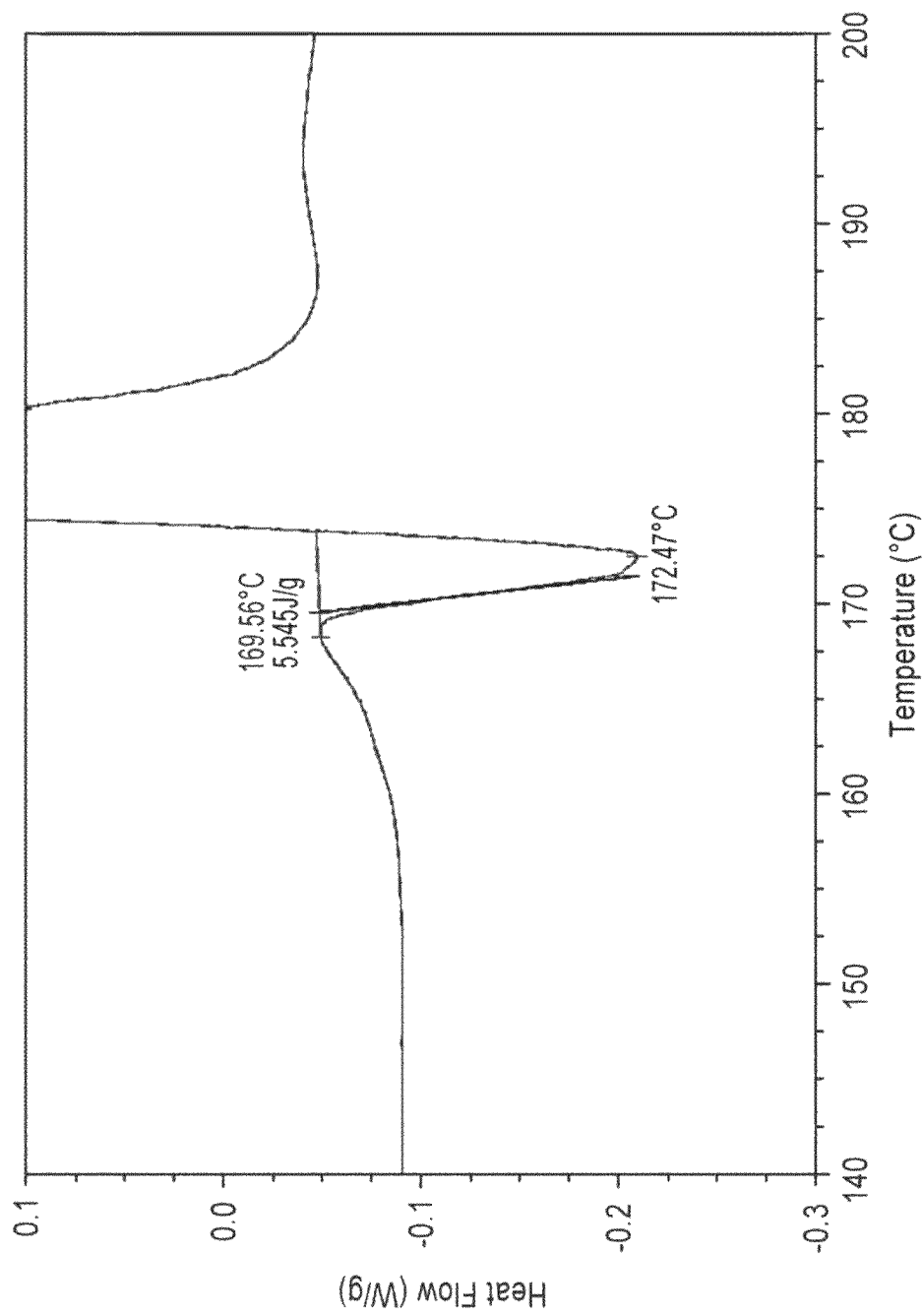
FIG. 16 shows a differential scanning calorimetry plot of Sample 1 of Morphic Form I of marizomib at 5° C. per minute.

FIG. 16 shows a differential scanning calorimetry plot of Sample 1 of Morphic Form I of marizomib at 5° C. per minute. As shown in FIG. 16, an endotherm was observed at 169.6° C. (5.5. J/g) followed by a sharp exotherm at 173-183° C. Without wishing to be bound by theory, the exotherm could be due to sample degradation.

Figure 17:
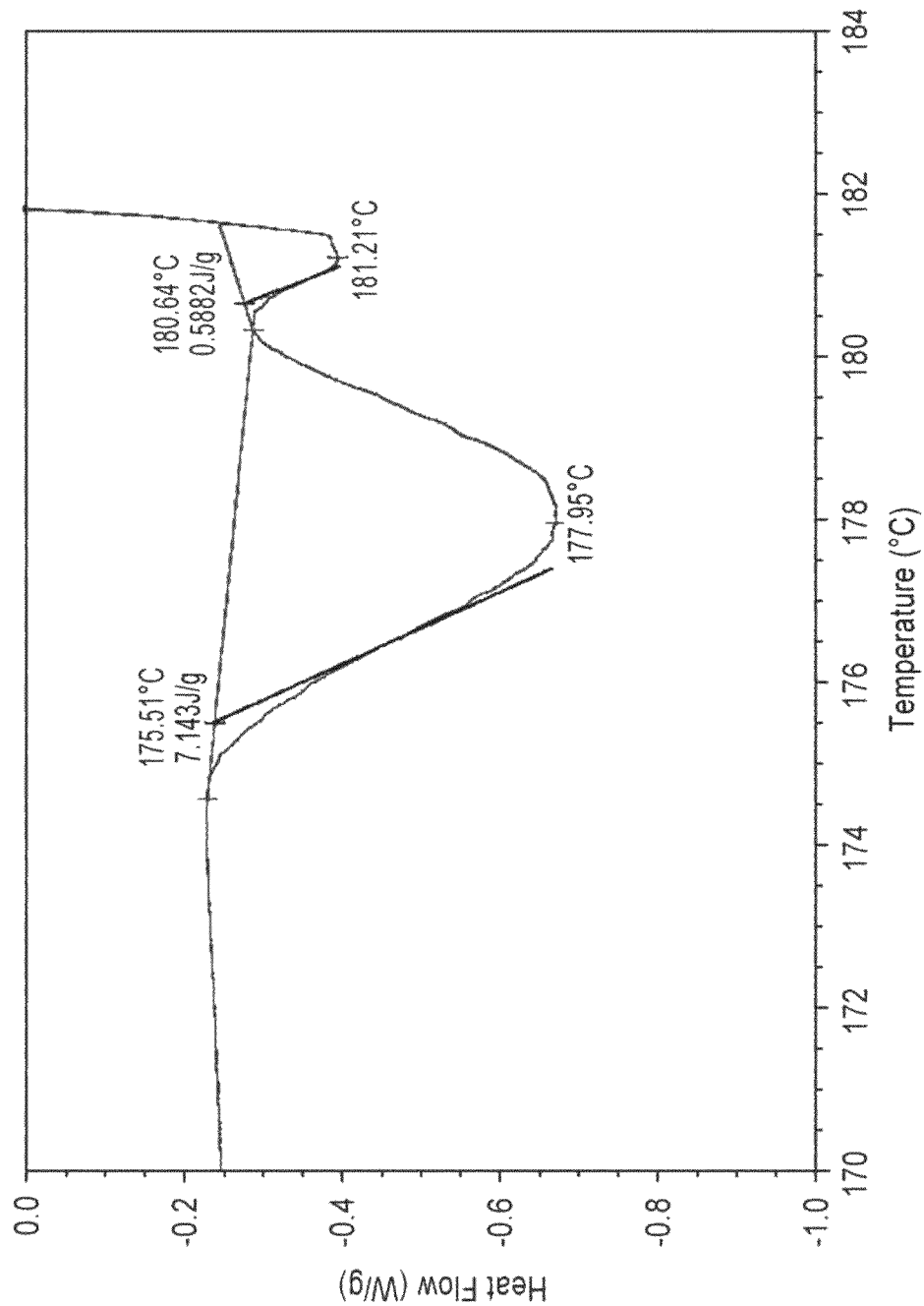
FIG. 17 shows a differential scanning calorimetry plot of Sample 1 of Morphic Form I of marizomib at 10° C. per minute.

FIG. 17 shows a differential scanning calorimetry plot of Sample 1 of Morphic Form I of marizomib at 10° C. per minute. As shown in FIG. 17, a small endotherm was observed at 175.5° C. (7.1 J/g) and 180.6° C. (0.6 J/g). The two endotherms were followed by an exotherm at about 183-193° C. Without wishing to be bound by theory, the exotherm could be due to sample degradation.

Figure 18:
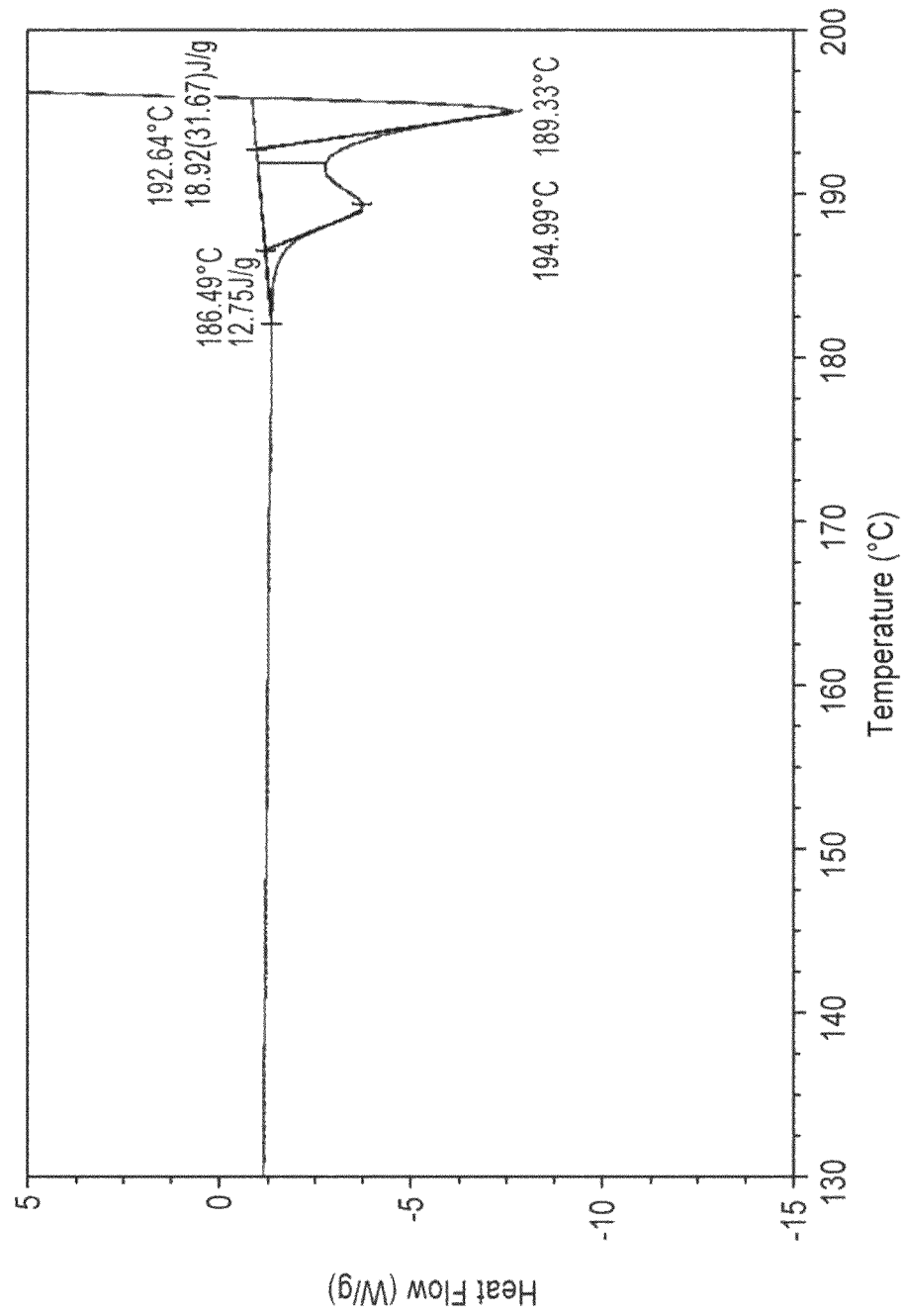
FIG. 18 shows a differential scanning calorimetry plot of Sample 1 of Morphic Form I of marizomib at 50° C. per minute.

FIG. 18 shows a differential scanning calorimetry plot of Sample 1 of Morphic Form I of marizomib at 50° C. per minute. As shown in FIG. 18, two small endotherms were observed at about 186.5° C. (12/8 J/g) and about 192.6° C. (18.9 J/g). The two endotherms were followed by an exotherm at about 193-205° C. Without wishing to be bound by theory, this could be due to sample degradation.

Figure 19:
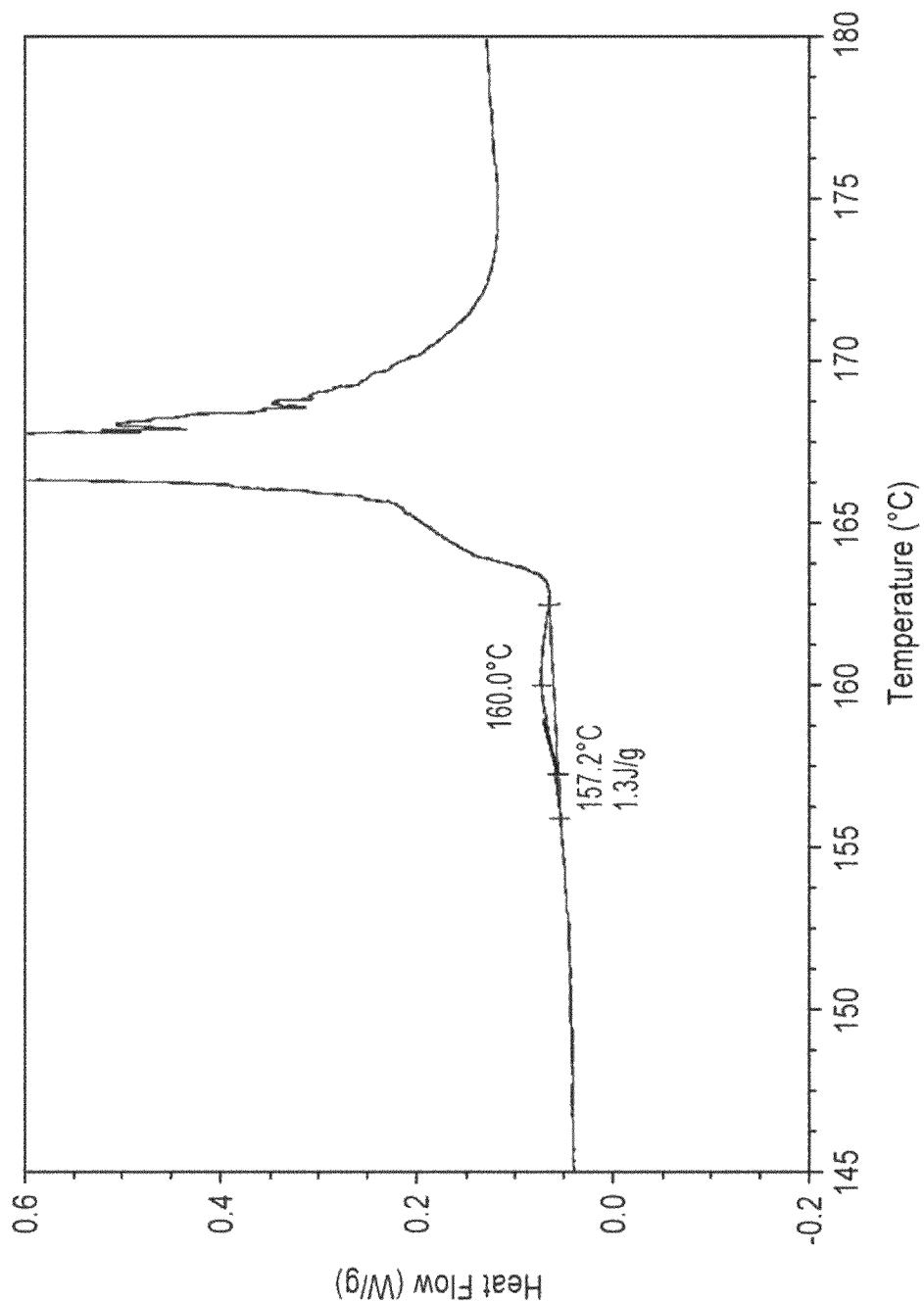
FIG. 19 shows a differential scanning calorimetry plot of Sample 3 of Morphic Form I of marizomib at 2° C. per minute.

FIG. 19 shows a differential scanning calorimetry plot of Sample 3 of Morphic Form I of marizomib at 2° C. per minute. As shown in FIG. 19, no endotherms were observed. Two exotherms were observed at about 155-175° C. Without wishing to be bound by theory, this could be due to sample degradation.

Figure 20:
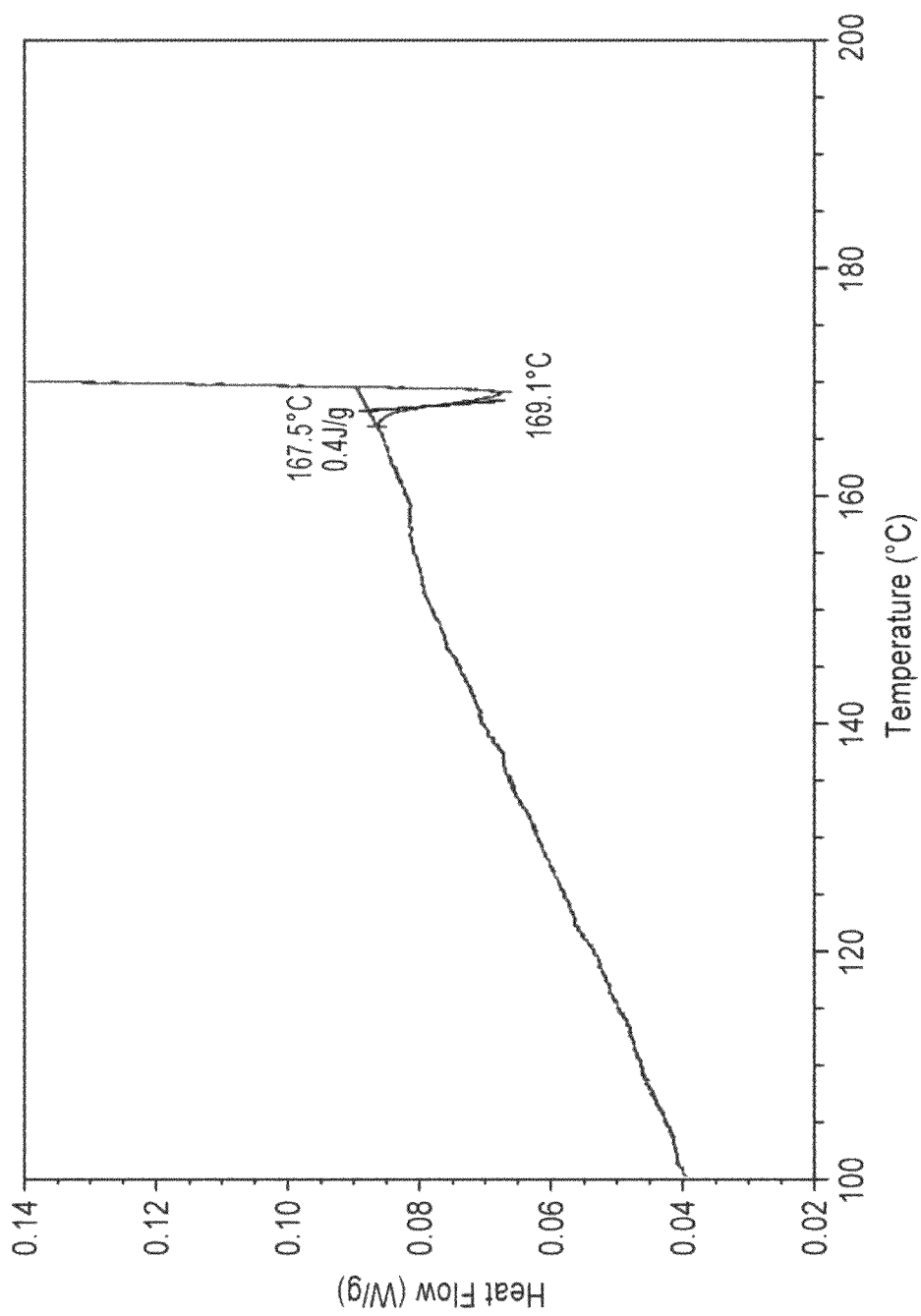
FIG. 20 shows a differential scanning calorimetry plot of Sample 3 of Morphic Form I of marizomib at 5° C. per minute.

FIG. 20 shows a differential scanning calorimetry plot of Sample 3 of Morphic Form I of marizomib at 5° C. per minute. As shown in FIG. 20, a small endotherm was observed at 167.5° C. (0.4 J/g) followed by a sharp exotherm at about 173-183° C. Without wishing to be bound by theory, this could be due to sample degradation.

Figure 21:
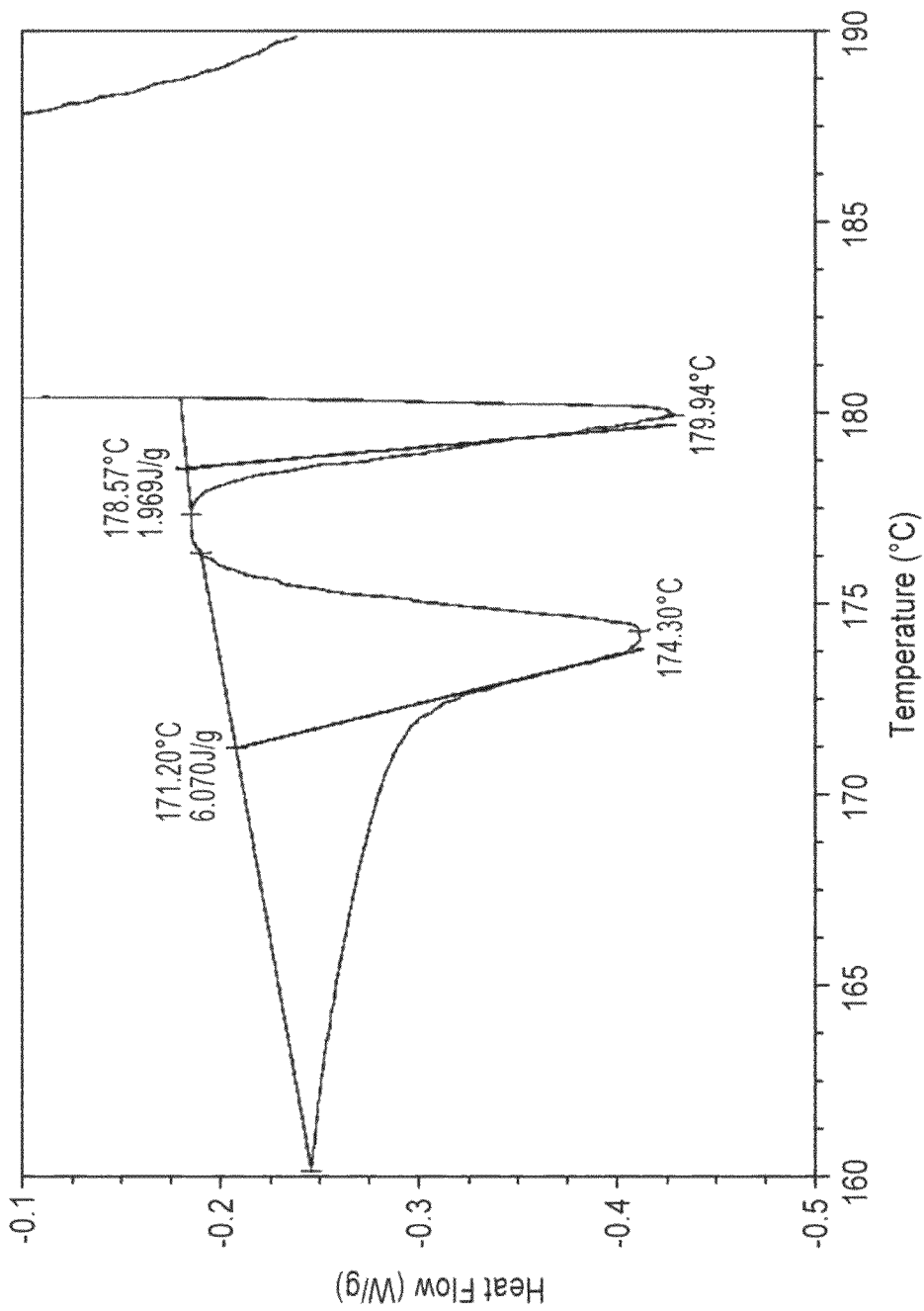
FIG. 21 shows a differential scanning calorimetry plot of Sample 3 of Morphic Form I of marizomib at 10° C. per minute.

FIG. 21 shows a differential scanning calorimetry plot of Sample 3 of Morphic Form I of marizomib at 10° C. per minute. As shown in FIG. 21, two small endotherms were observed at about 171.2° C. (6.1 J/g) and about 178.6° C. (2.0 J/g), followed by an exotherm at about 183-193° C. Without wishing to be bound by theory, this could be due to sample degradation.

Figure 22:
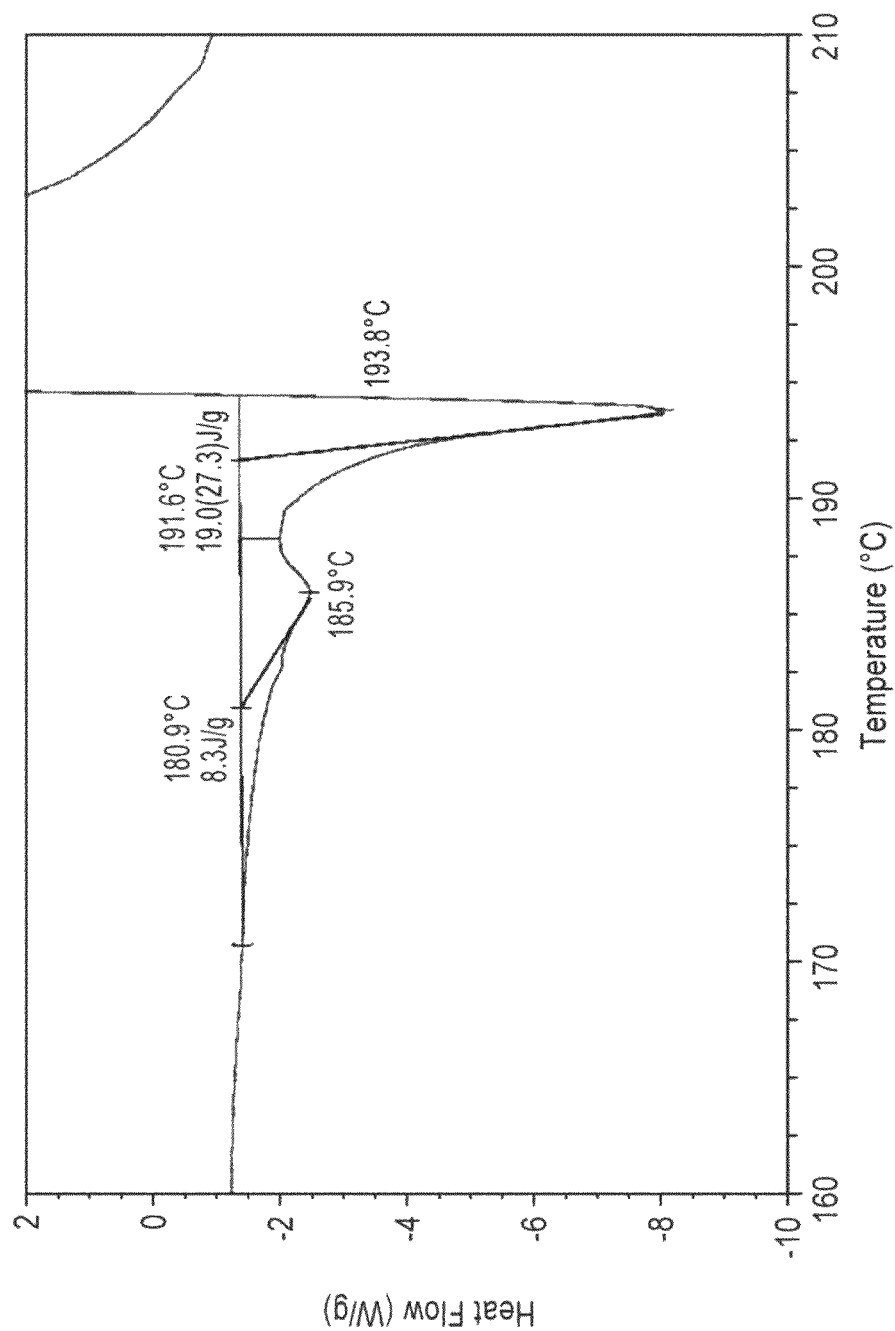

FIG. 22 shows a differential scanning calorimetry plot of Sample 3 of Morphic Form I of marizomib at 50° C. per minute. As shown in FIG. 22, two small endotherms were observed at about 180.9° C. (8.3 J/g) and 191.6° C. (19.0 J/g). The two small endotherms were followed by an exotherm at about 193-205° C. Without wishing to be bound by theory, this could be due to sample degradation.

As set forth in FIGS. 15-22, as the heating rate of the DSC experiments increased, a shift in onset temperature as well as a variation in enthalpy was observed. Without wishing to be bound by theory, these fluctuations observed in the temperature onset and enthalpy can be due to combination of melt and degradation of the sample. In other words, without wishing to be bound by theory, a pure melt of a crystalline, non-solvated morphic form is a thermodynamic event, so that changes in heating rate and/or amount of input material will not significantly affect the onset temperature of the melt. In contrast, sample degradation is a kinetic event, so that changes in the experimental parameters (amount of input material, heating rate, type of pan used, i.e. sealed or unsealed) can cause a shift in the onset temperature of that event.

Without wishing to be bound by theory, based on the results of DSC analysis of Samples 1 and 3, the changes observed in the main endothermic event can be due to both thermodynamic and kinetic factors, i.e. both melt and degradation of the sample.

Without wishing to be bound by theory, the results of the DSC and TG analysis of morphic Form I is consistent with the results set forth in FIGS. 5 and 6. FIGS. 5 and 6 demonstrate that Sample 1 and 3 remained as Form I throughout the increase in temperature from 25° C. to 160° C. Discoloration of the sample was observed at about 160° C. from white to yellow, as shown in FIGS. 33-36. However, after about five minutes to enable equilibration at about 160° C., the sample was observed to melt and degrade simultaneously.

Without wishing to be bound by theory, this result is further supported by the outcome from the hot stage microscopy experiments, in which crystals from Sample 1 were subjected to heating under air at ~30° C./min. No changes were observed between 30 and 150° C. Between 160-175° C. changes were observed which captured the melt of the crystals and degradation of the sample (in form of discoloration) occurring substantially simultaneously.

Figure 23:
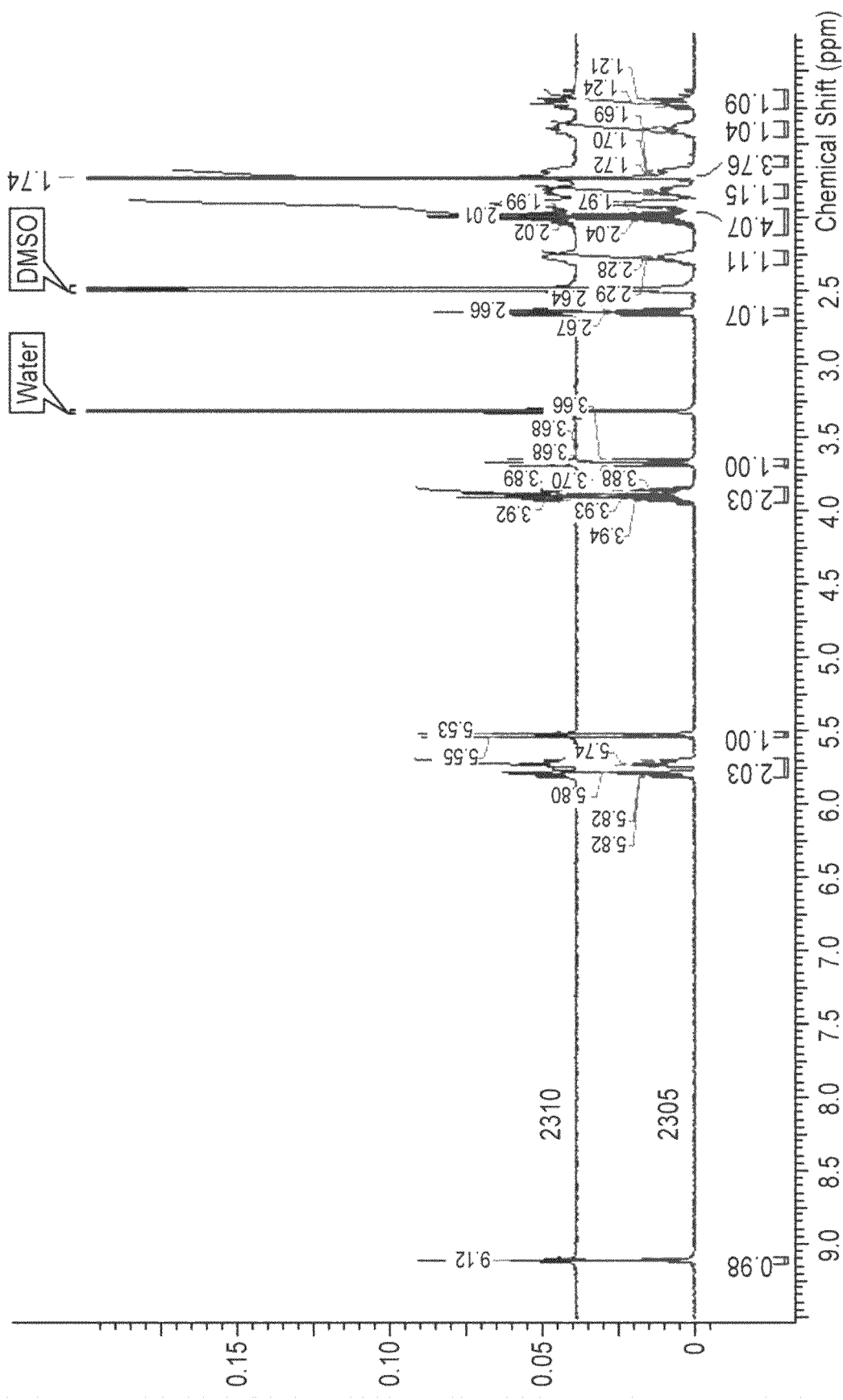
FIG. 23 shows a $^1$HNMR spectrum for both Sample 1 and Sample 3 of marizomib.

FIG. 23 shows a $^1$HNMR spectrum for both Sample 1 (2305) and Sample 3 (2310) of marizomib. As shown in FIG. 23, both spectra are consistent with the structure of marizomib.

Figure 24:
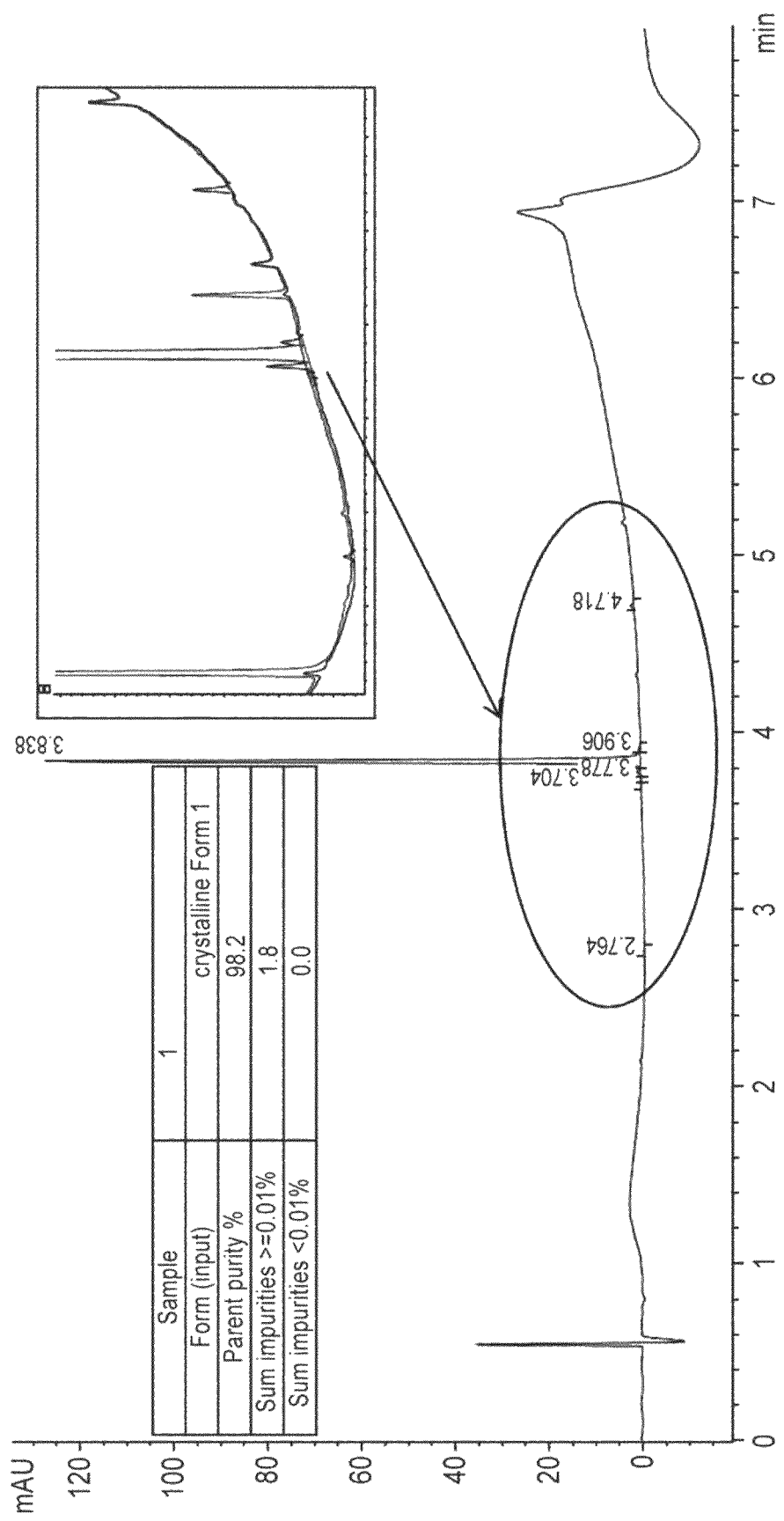
FIG. 24 is an HPLC plot of Sample 1 of marizomib.

FIG. 24 is an HPLC plot of Sample 1 of marizomib. As shown in FIG. 24, the purity of Sample 1 was at least 98.2%.

Figure 25:
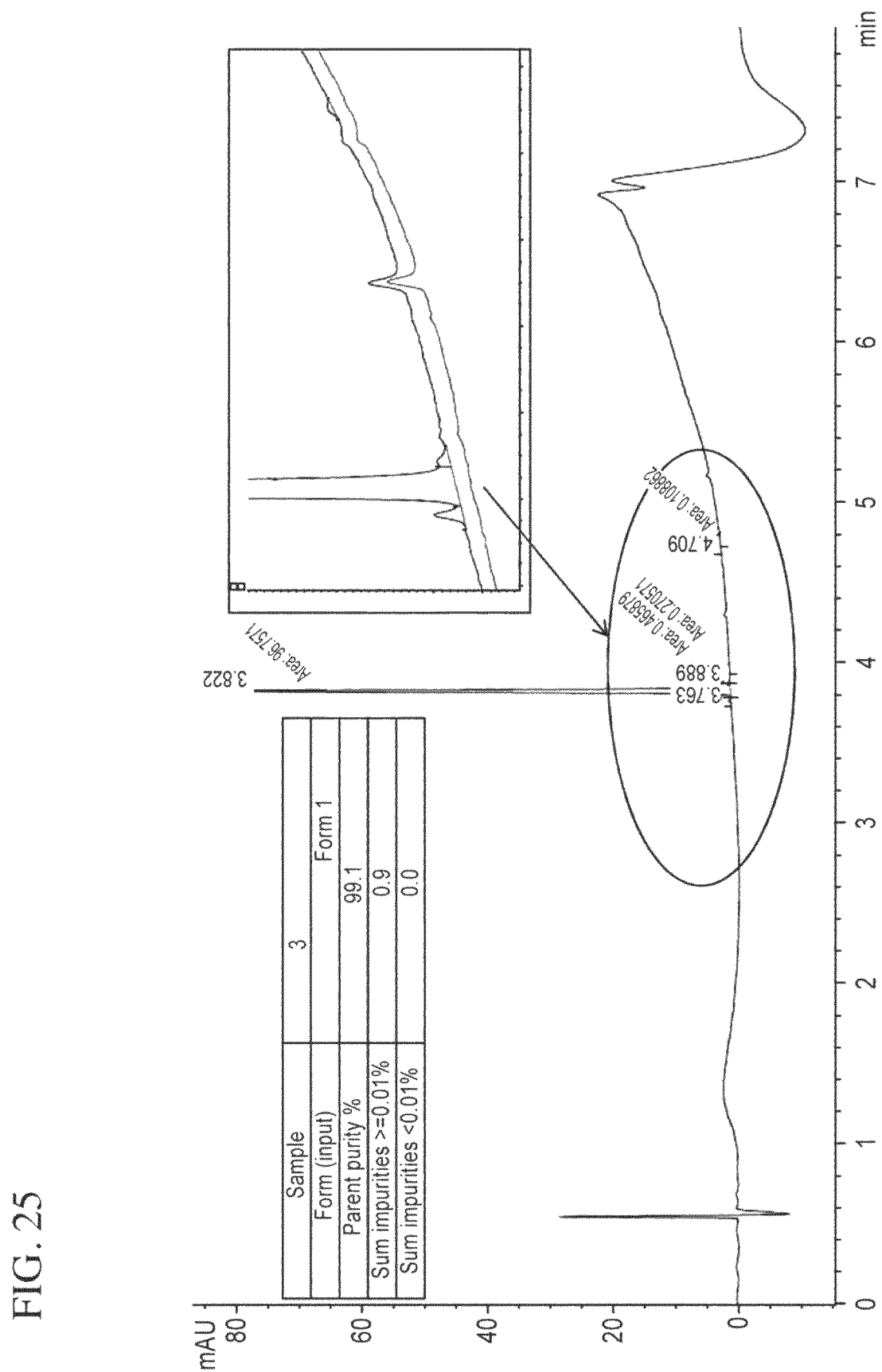
FIG. 25 is an HPLC plot of Sample 3 of marizomib.

FIG. 25 is an HPLC plot of Sample 3 of marizomib. As shown in FIG. 25, the purity of Sample 3 was at least 99.1%.

Figure 31:
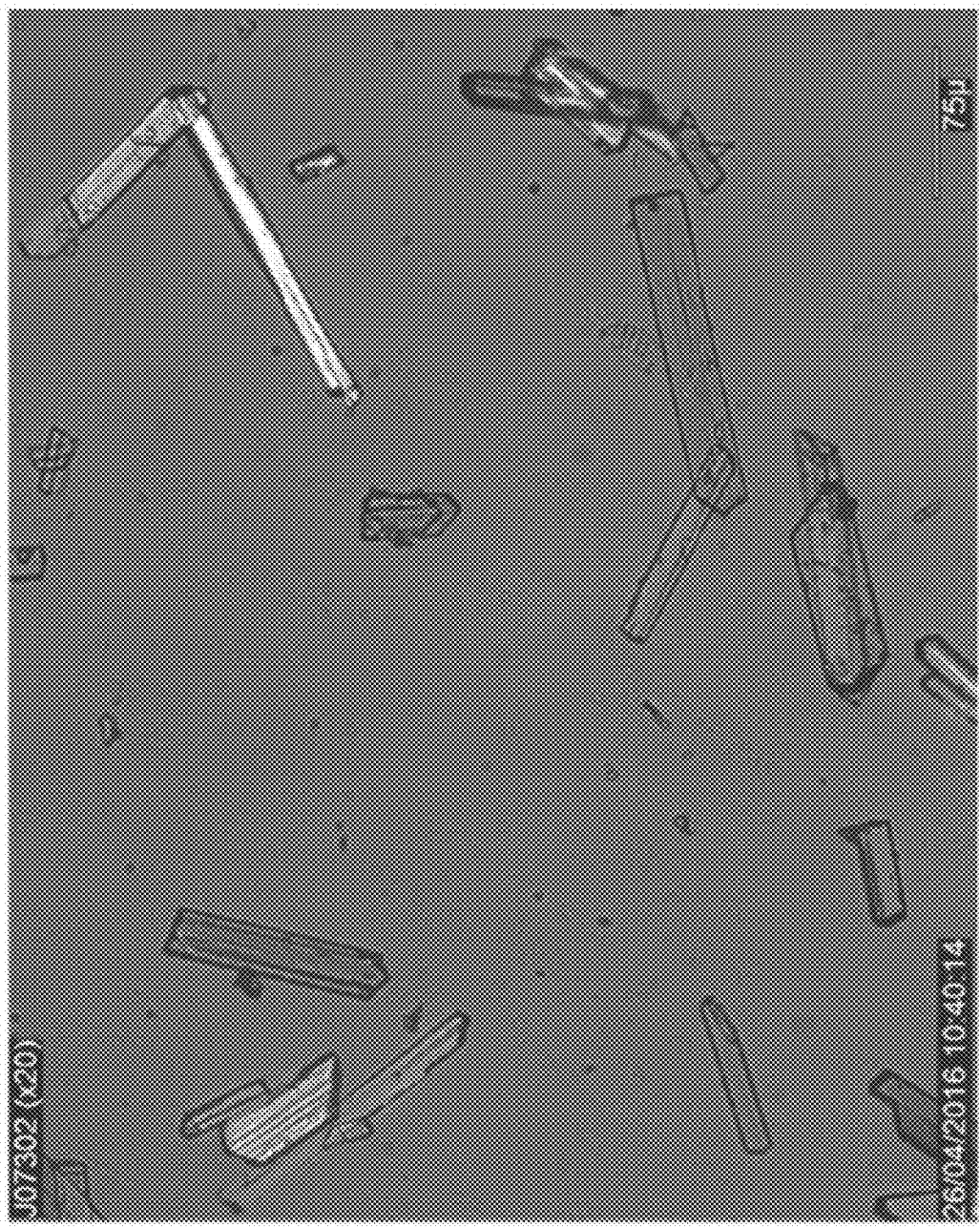
FIG. 31 is a polarized light microscope image of Morphic Form I of Sample 1 of marizomib.

FIG. 31 is a polarized light microscope image of Morphic Form I of Sample 1 of marizomib. As shown in FIG. 31, particles of Sample 1 had a lath morphology with particle size of 150 μm up to 300 μm in length.

Figure 32:
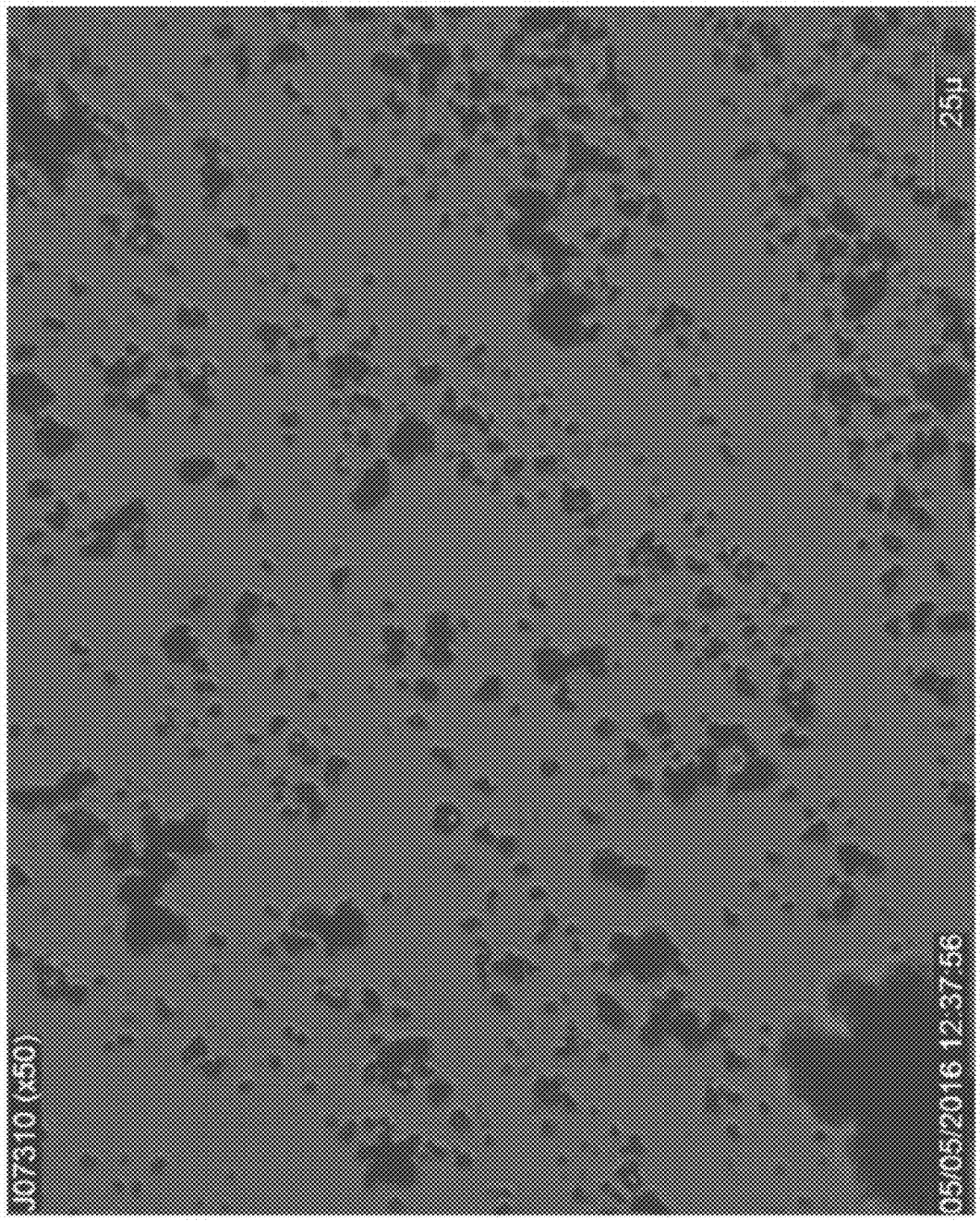
FIG. 32 is a polarized light microscope image of Morphic Form 1 of Sample 3 of marizomib.

FIG. 32 is a polarized light microscope image of Morphic Form I of Sample 3 of marizomib. As shown in FIG. 32, there is no lath morphology in the micronized sample. The samples are in some embodiments more sphere-like.

Figure 33:
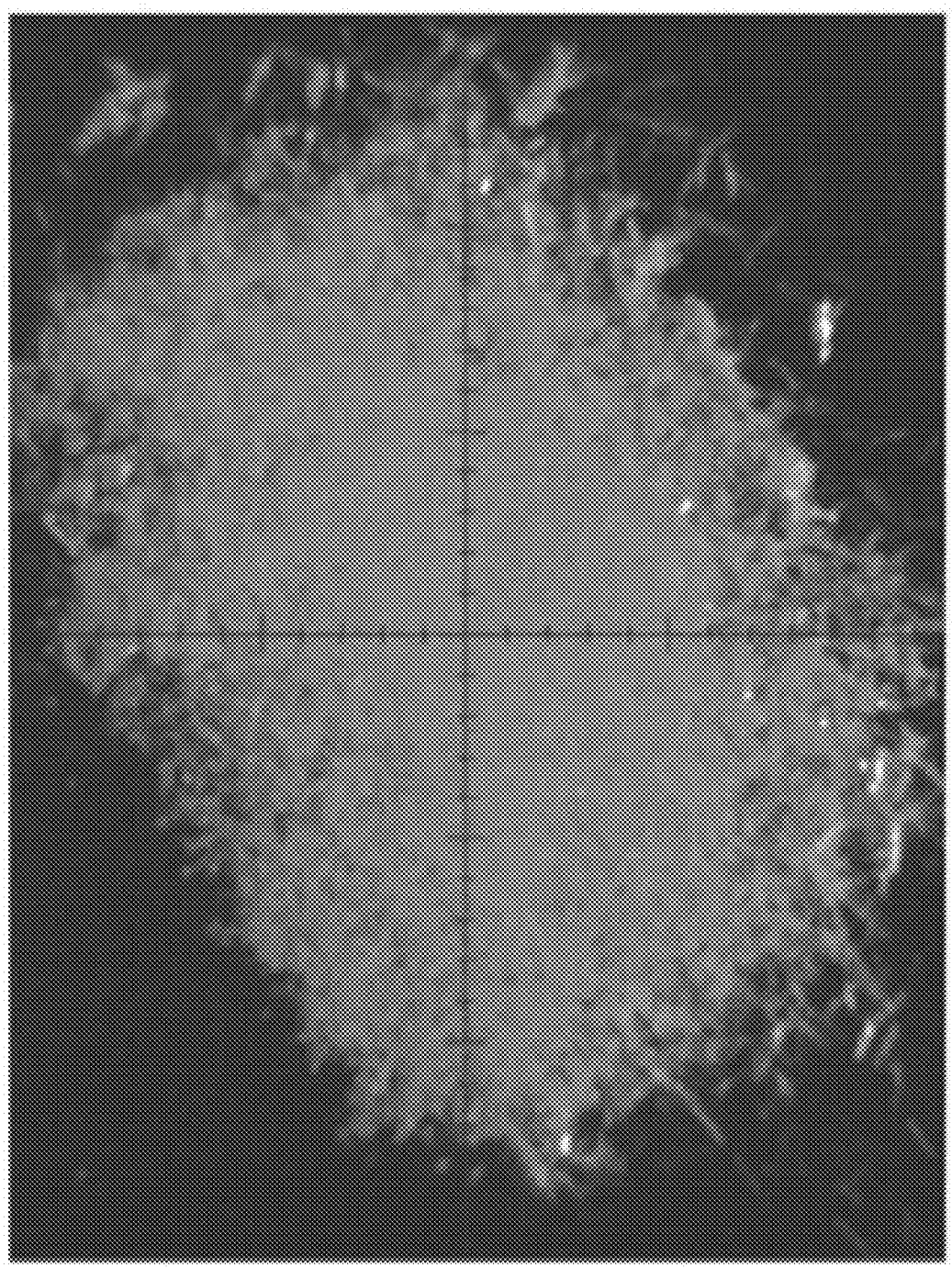
FIG. 33 is a photo of Sample 1 of Morphic Form I of marizomib at 25° C.
Figure 34:
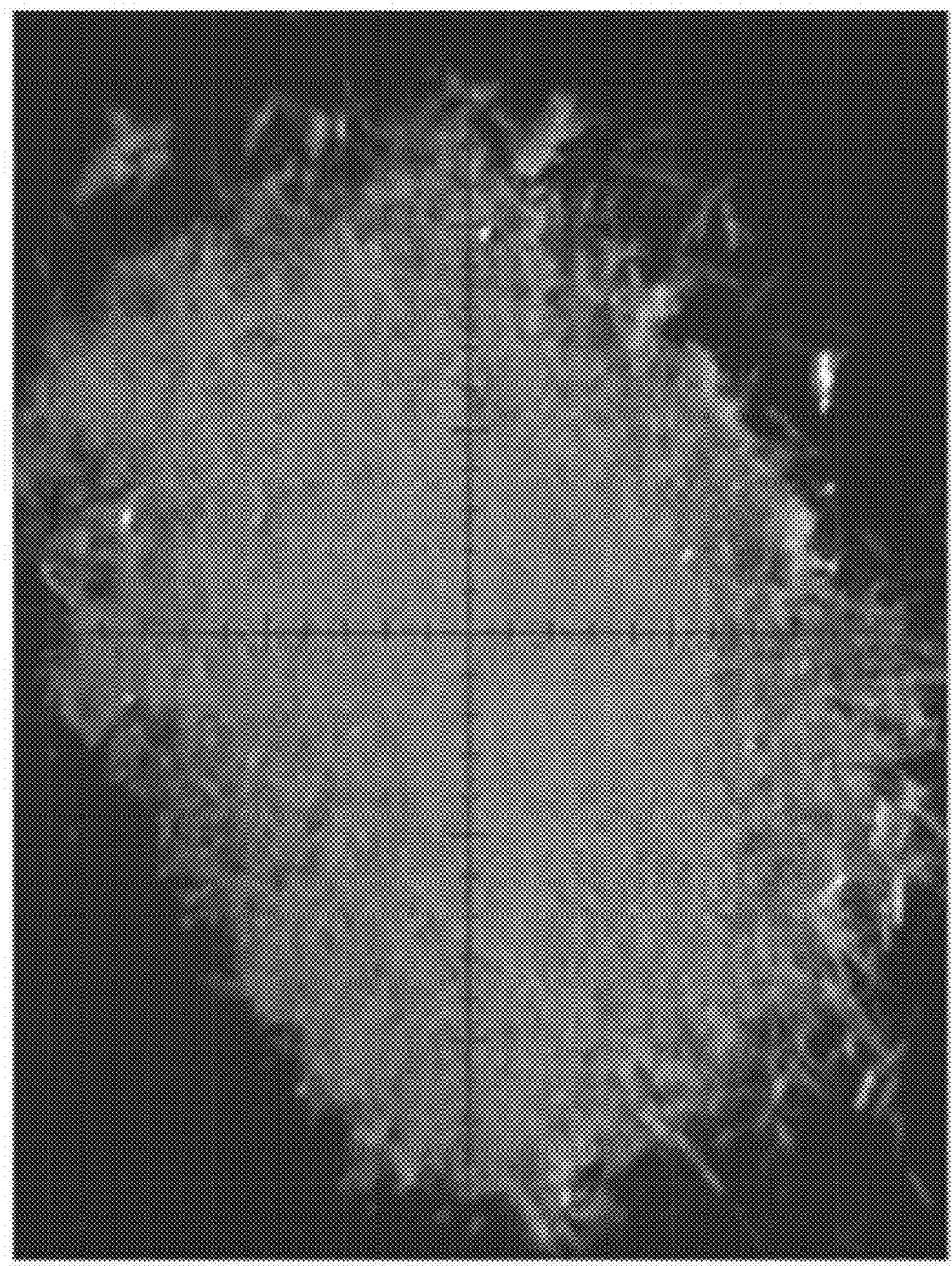
FIG. 34 is a photo of Sample 1 of Morphic Form I of marizomib at 150° C.
Figure 35:
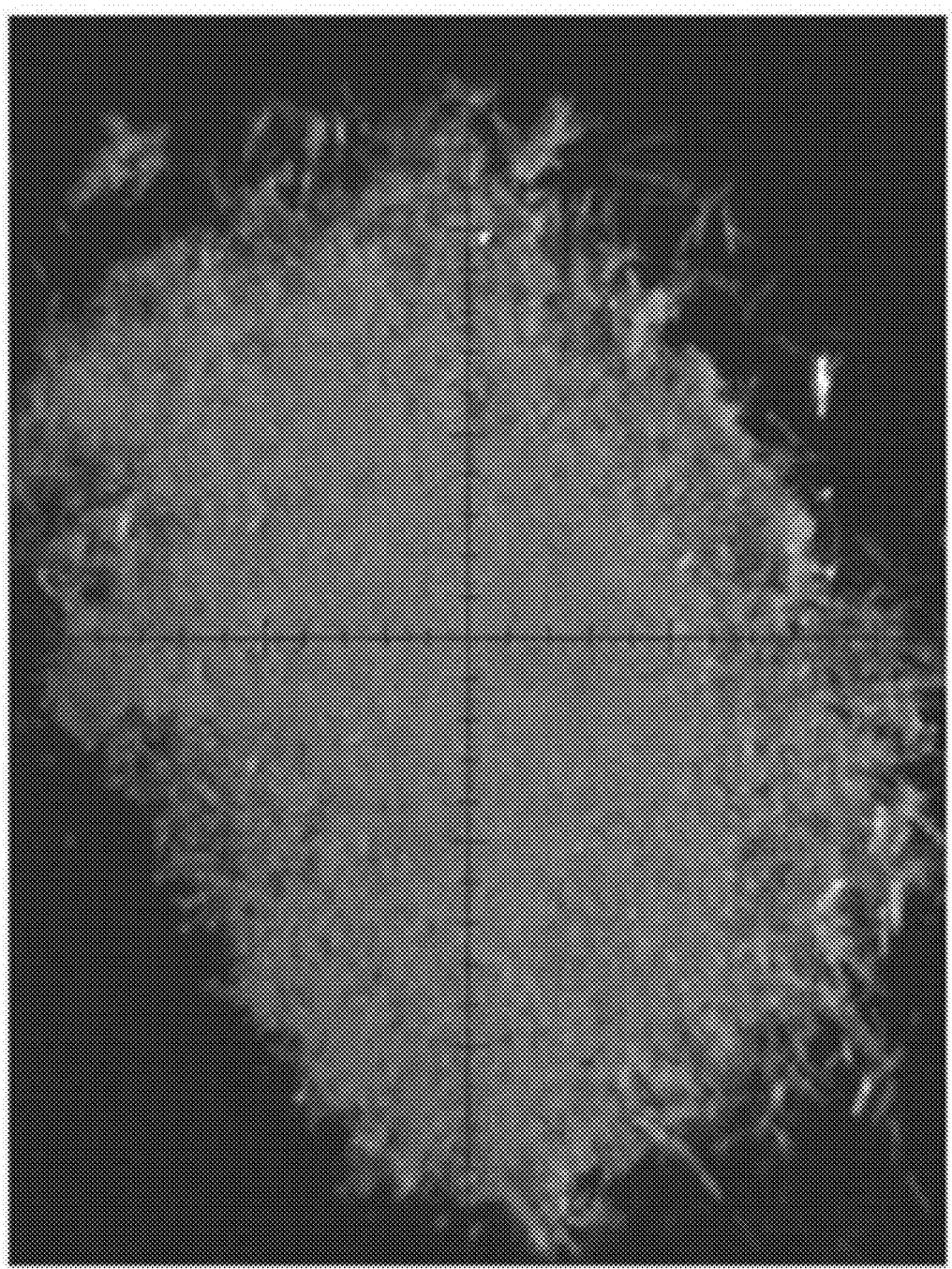
FIG. 35 is a photo of Sample 1 of Morphic Form I of marizomib at 160° C.

FIG. 33 is a photo of Sample 1 of Morphic Form I of marizomib during the variable temperature XRPD analysis at 25° C. FIG. 34 is a photo of Sample 1 of Morphic Form I of marizomib during the variable temperature XRPD analysis at 150° C. FIG. 35 is a photo of Sample 1 of Morphic Form I of marizomib at during the variable temperature XRPD analysis 160° C. Discoloration of the sample, from white to yellow, was observed at about 160° C.

Figure 36:
FIG. 36 is a photo of Sample 1 of Morphic Form I of marizomib at 160° C. after five minutes.

FIG. 36 is a photo of Sample 1 of Morphic Form I of marizomib at during the variable temperature XRPD analysis 160° C. after five minutes. As shown in FIG. 36, the sample appears to be both melting and degrading. Without wishing to be bound by theory, this result is consistent with the TG and DSC analysis of Sample 1, which suggested that the morphic Form I begins to melt and/or degrade at about 160° C.

Figure 37:
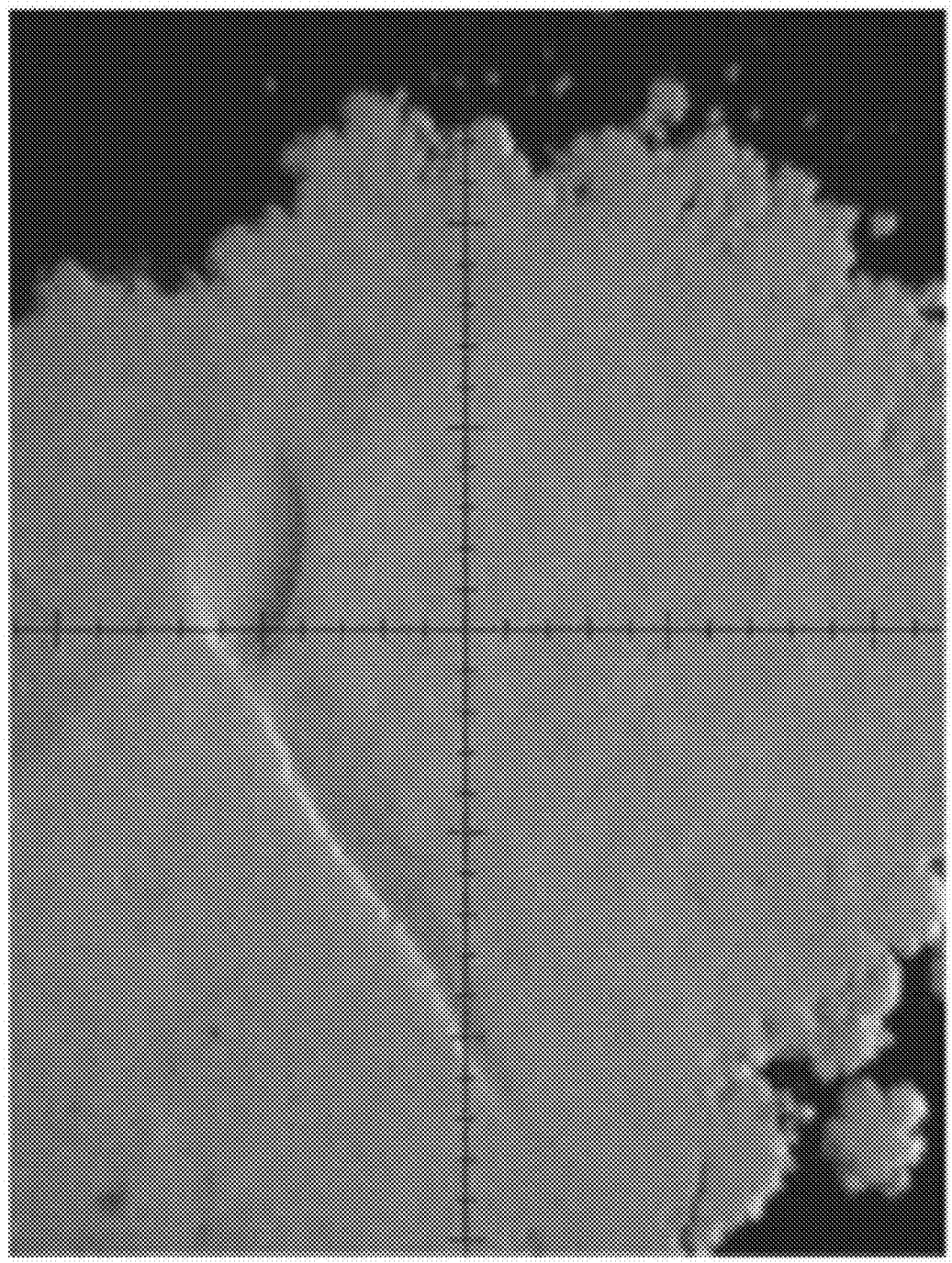
FIG. 37 is a photo of Sample 3 of Morphic Form 1 of marizomib at 25° C.
Figure 38:
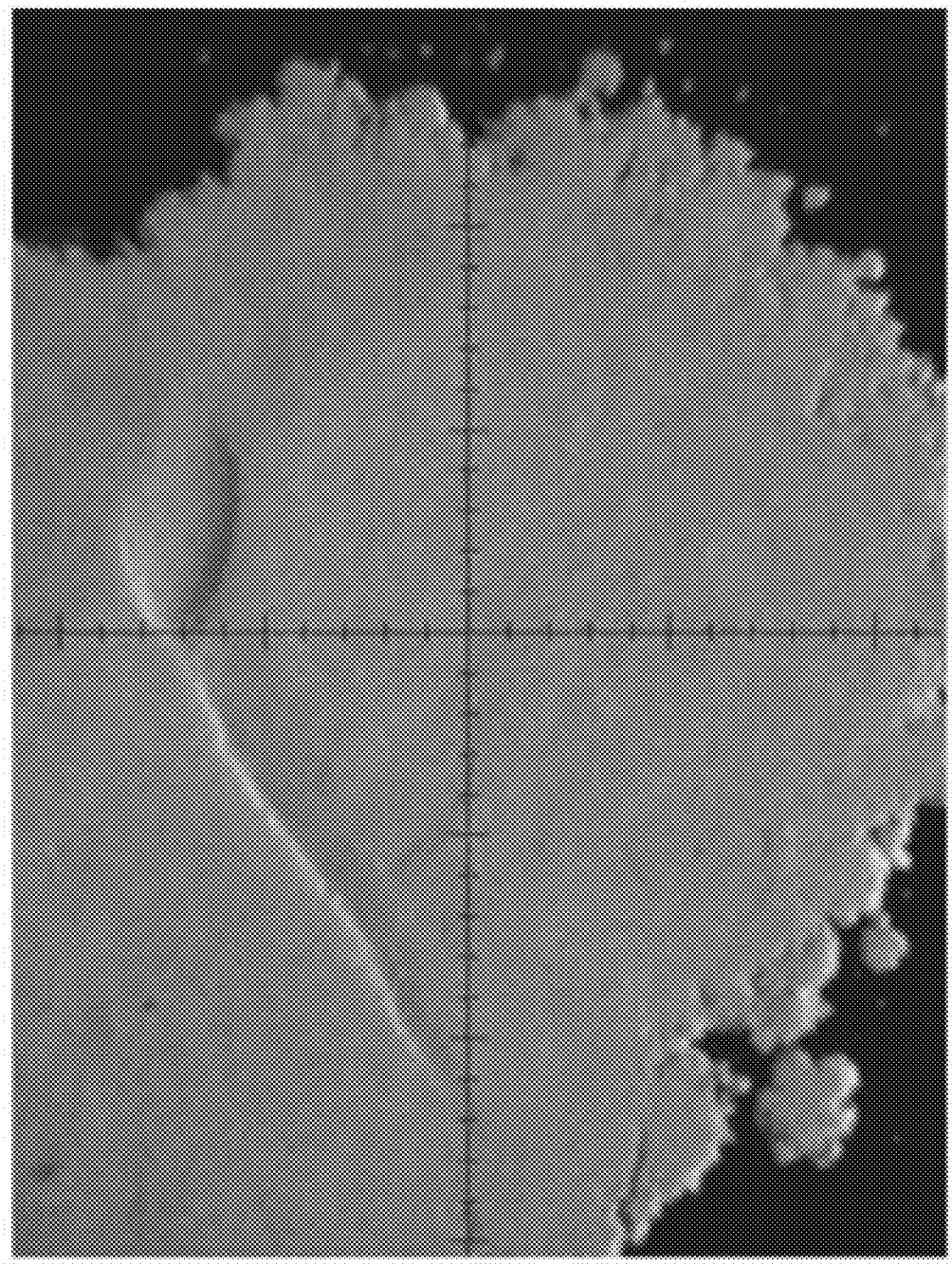
FIG. 38 is a photo of Sample 3 of Morphic Form I of marizomib at 150° C.
Figure 39:
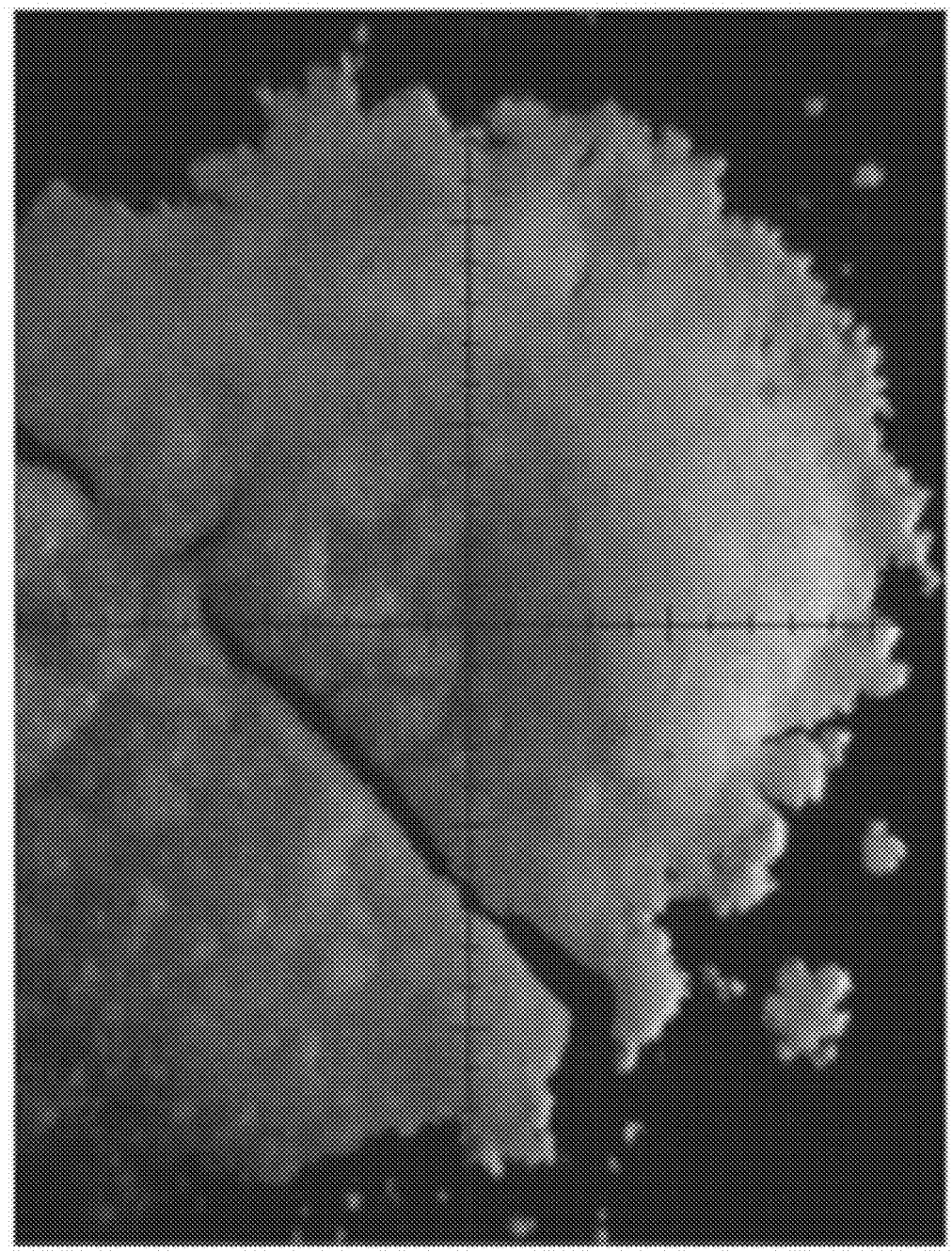
FIG. 39 is a photo of Sample 3 of Morphic Form I of marizomib at 160° C.
Figure 40:
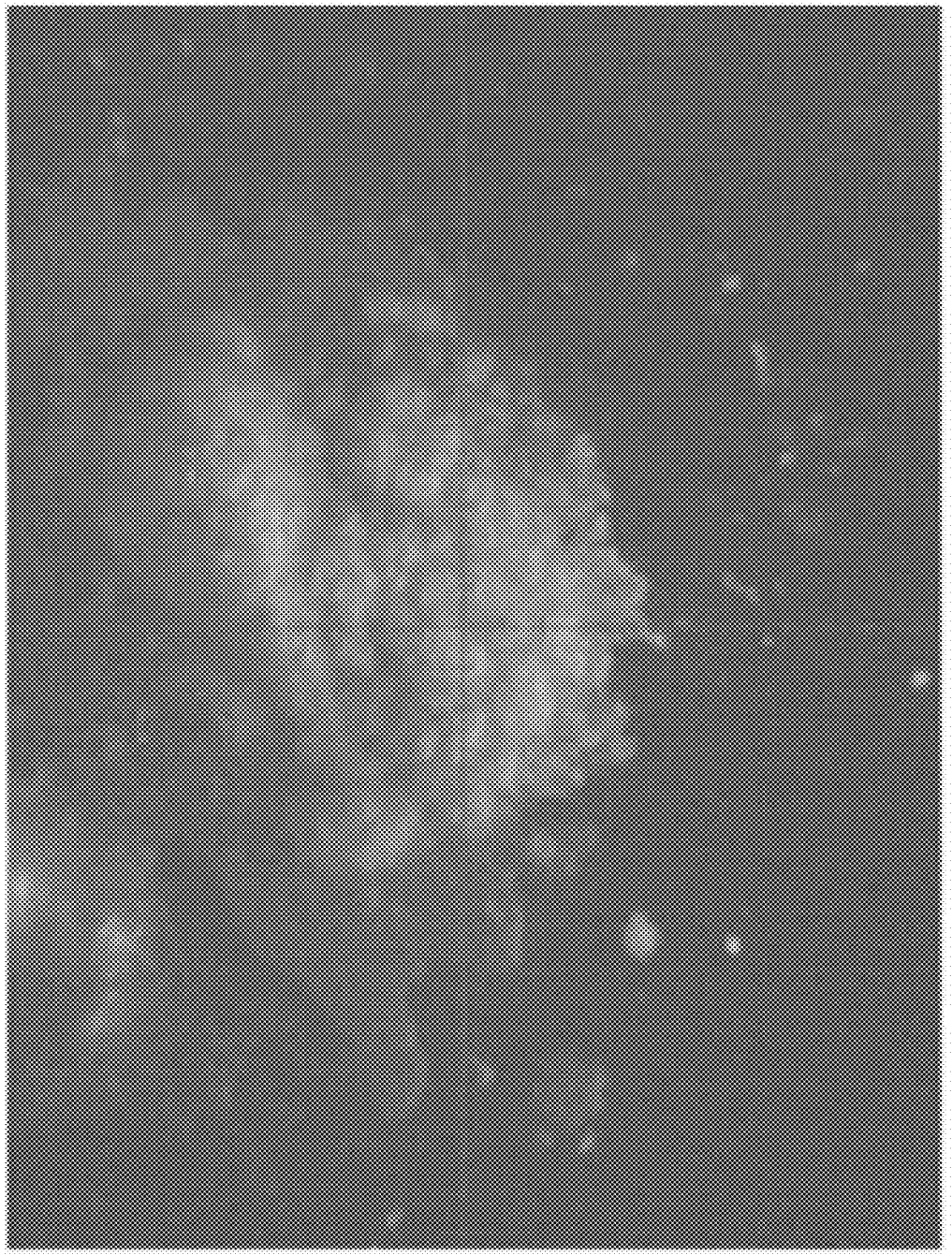
FIG. 40 is a photo of Sample 3 of Morphic Form I of marizomib at 160° C. after five minutes.

Sample 3 of morphic Form I showed similar characteristics to Sample 1. FIG. 37 is a photo of Sample 3 of Morphic Form I of marizomib at 25° C. FIG. 38 is a photo of Sample 3 of Morphic Form I of marizomib at 150° C. FIG. 39 is a photo of Sample 3 of Morphic Form I of marizomib at 160° C. FIG. 40 is a photo of Sample 3 of Morphic Form I of marizomib at 160° C. after five minutes. As shown in FIGS. 37-40, Sample 3 had properties similar to Sample 1. For example, both samples exhibited discoloration at about 160° C. and melting and/or degradation after holding for about five minutes at about 160° C.

A fourth sample of marizomib, Form 1 ("Sample 4") was subjected to various conditions to attempt to prepare a different morphic form beyond Form I. The indexing parameters of Sample 4 are given below in Table-4:

TABLE 4

Parameters for Sample 4 Indexing

| | |
|---|---|
| Bravais Type | Primitive Monoclinic |
| a [Å] | 10.594 |
| b [Å] | 24.507 |
| c [Å] | 12.661 |
| α [deg] | 90 |
| β [deg] | 108.53 |
| γ [deg] | 90 |
| Volume [Å³/cell] | 3, 116.3 |
| Chiral Contents? | Chiral |
| Extinction Symbol | P 1 2$_1$ 1 |
| Space Group(s) | P2$_1$(4) |

Attempted Hydrolysis of Marizomib

Figure 26:
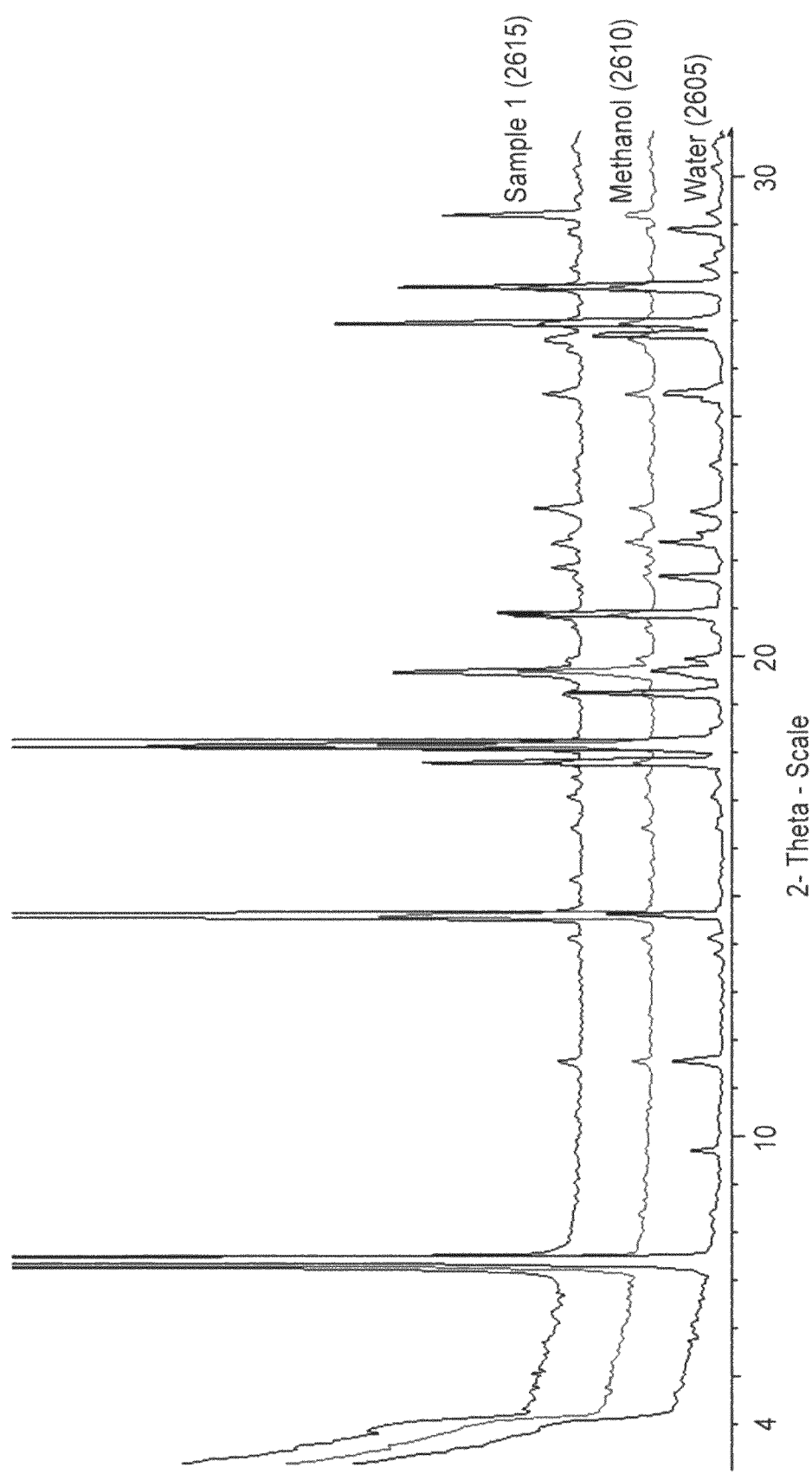
FIG. 26 is an XRPD plot of marizomib before and after attempted hydrolysis.
Figure 27:
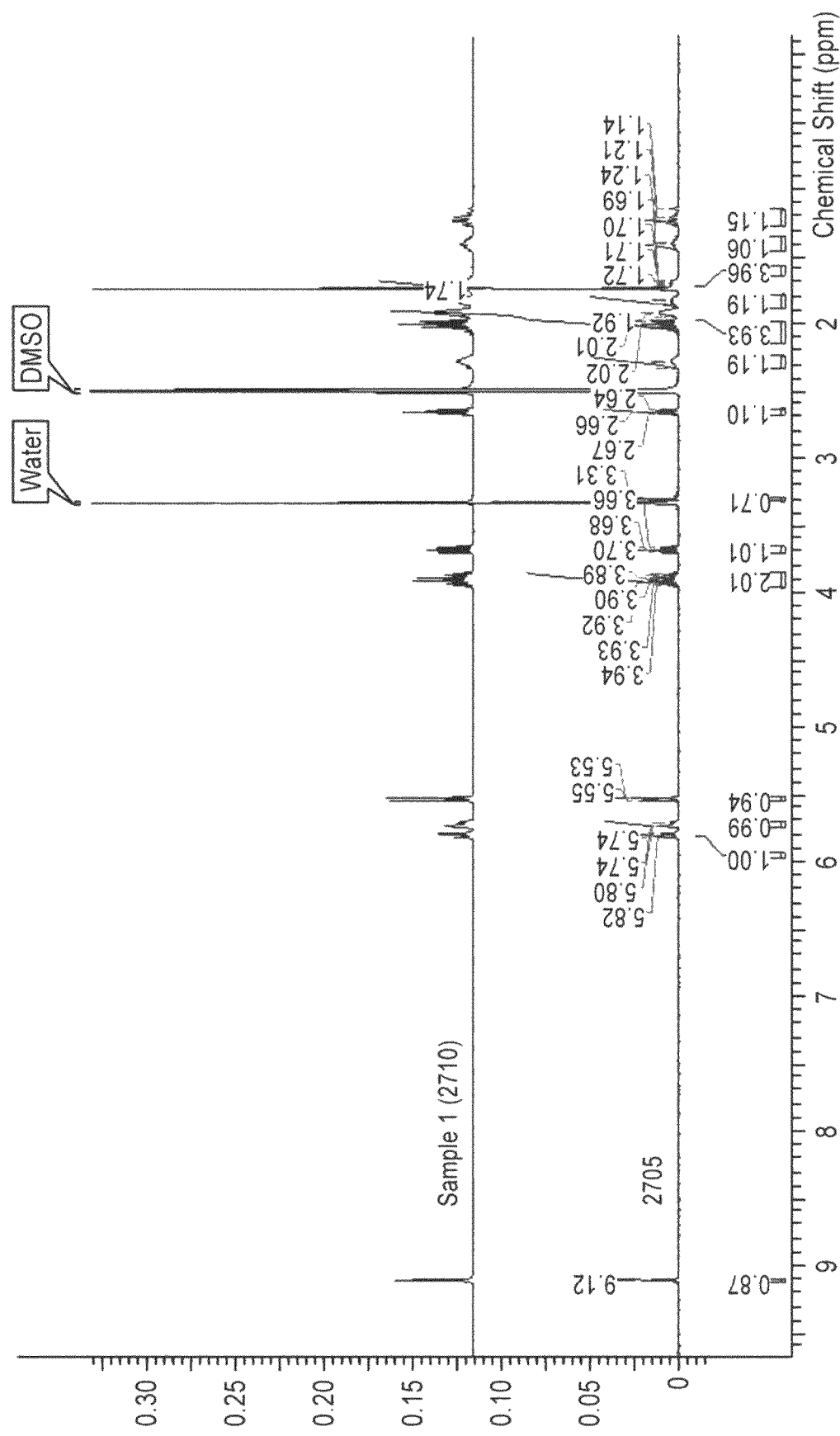
FIG. 27 is a 1HNMR plot of marizomib before and after attempted hydrolysis.
Figure 28:
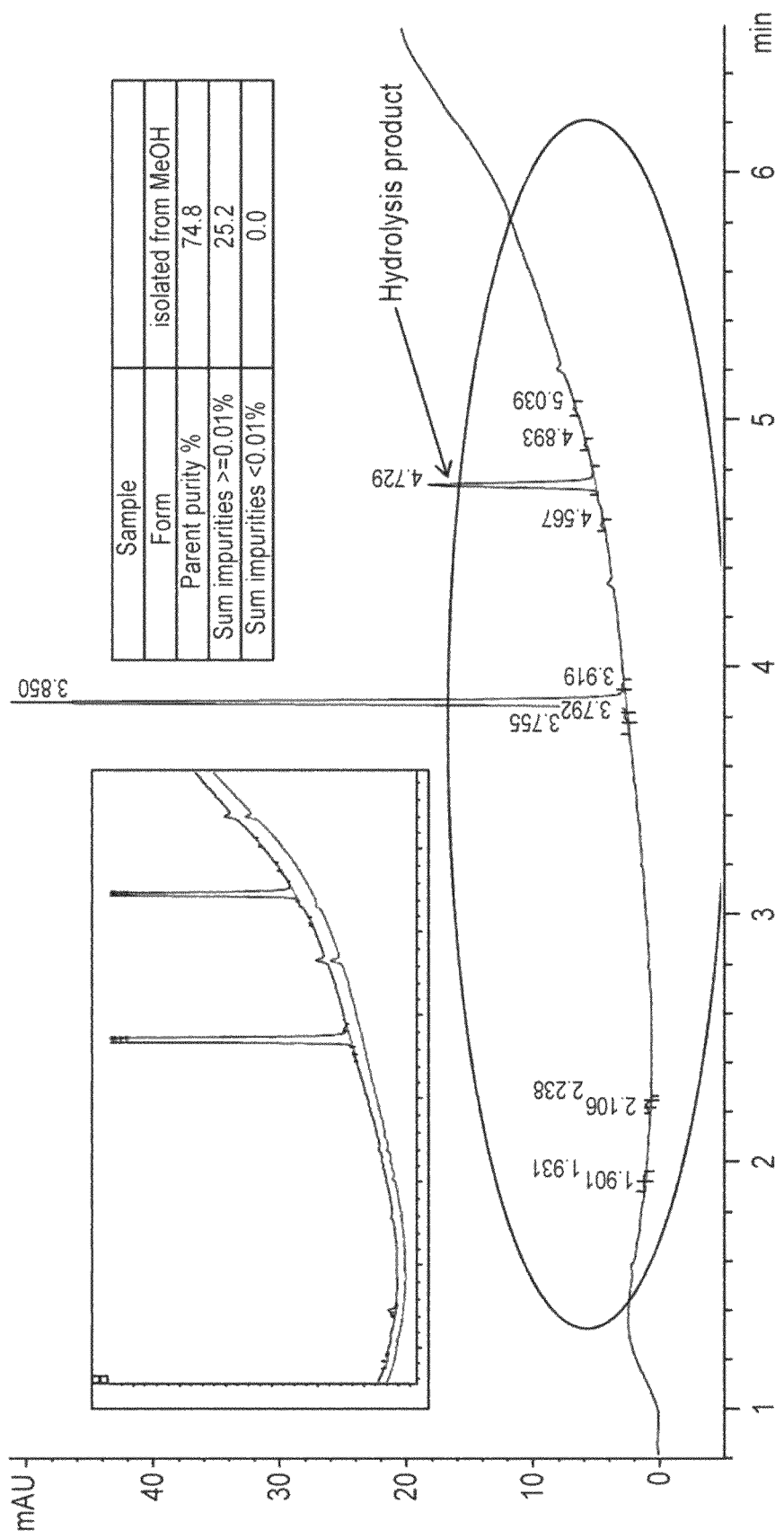
FIG. 28 is an HPLC plot of marizomib isolated after a hydrolysis attempt.
Figure 29:
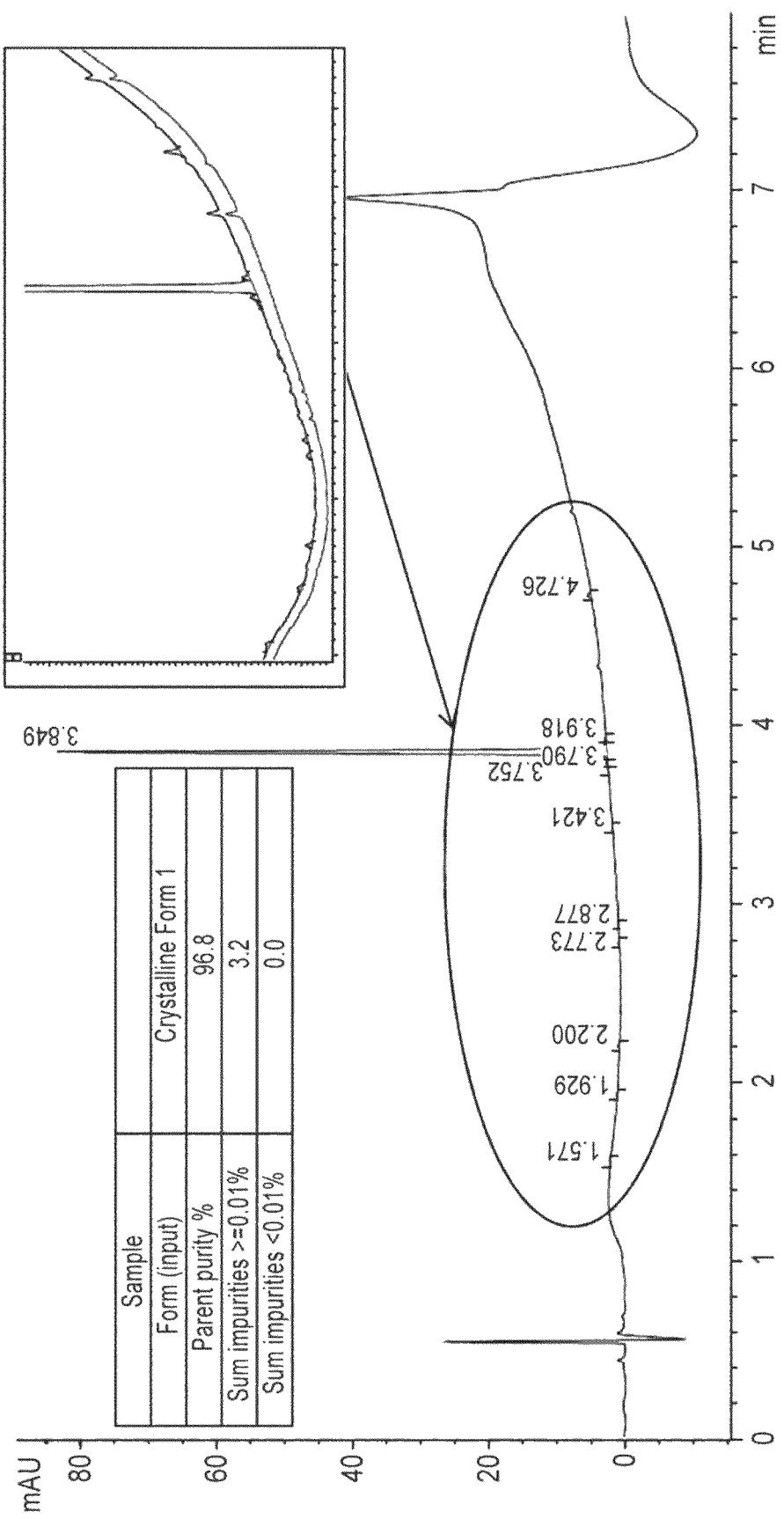
FIG. 29 is an HPLC plot of marizomib isolated from ethyl acetate
Figure 30:
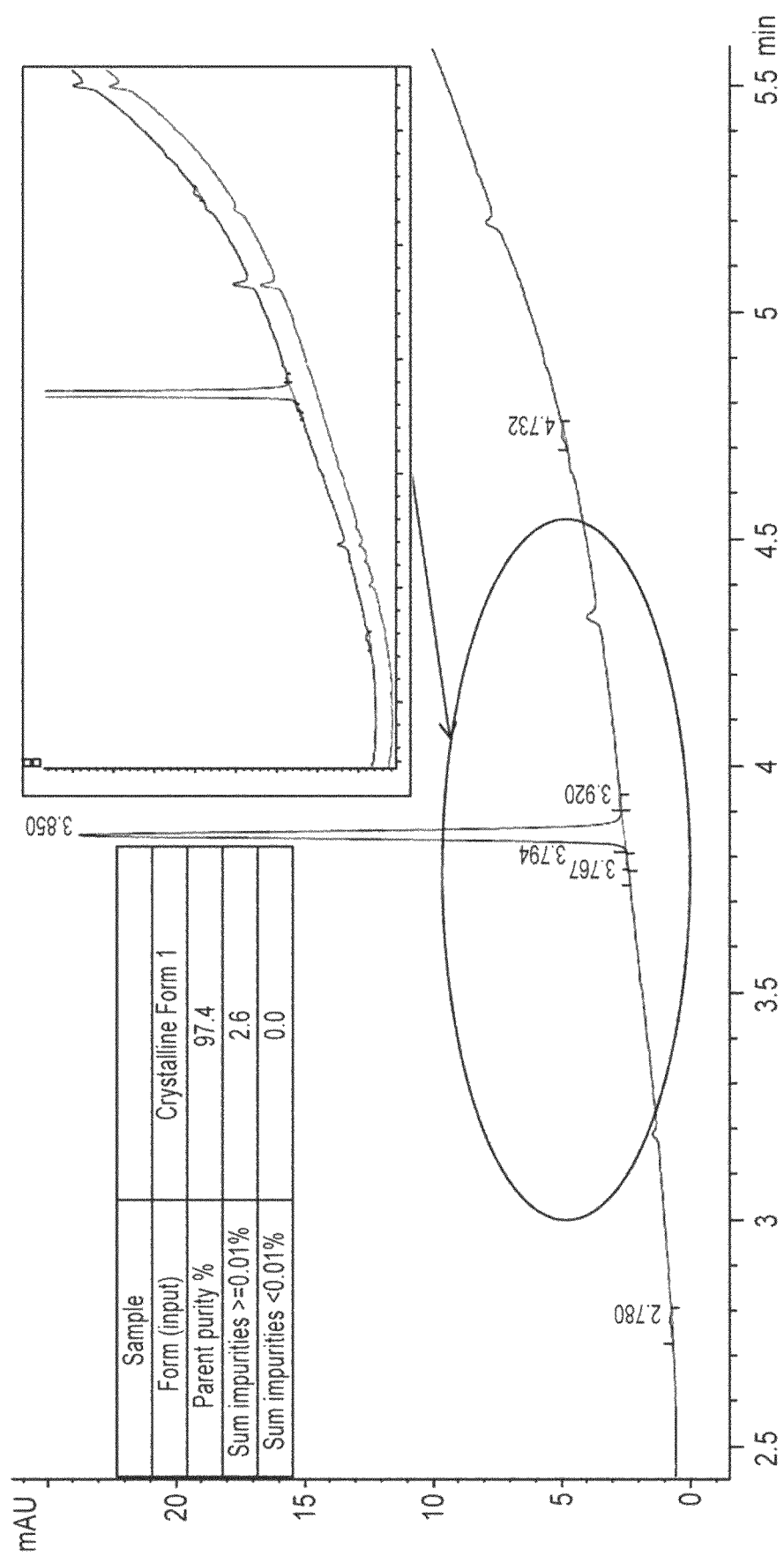
FIG. 30 is an HPLC plot of marizomib isolated from ethanol.

Without wishing to be bound by theory, it was hypothesized that marizomib could be hydrolyzed upon exposure to water. The results are given in Example 1. FIG. 26 is an overlay of three XRPD plots of Sample 1 of marizomib before (2615) and after attempted hydrolysis with water (2610) and methanol (2605). FIG. 27 is a $^1$HNMR plot of Sample 1 of marizomib before (2710) and after (2705) attempted hydrolysis. FIG. 28 is an HPLC plot of Sample 1 of marizomib isolated after a hydrolysis attempt with water. The samples were matured between 50° C. and room temperature heat-cool cycles (8 h per cycle) for 96 h. As shown in FIG. 28, the purity of the sample is reduced from about 99% to about 75% after four days. FIG. 29 is an HPLC plot of Sample 1 of marizomib isolated from ethyl acetate. FIG. 30 is an HPLC plot of Sample 1 of marizomib isolated from ethanol. As shown in FIG. 28, there was observed a new peak at a retention time of about 4.729 minutes. Without wishing to be bound by theory, this peak is understood to represent the hydrolysis product, as set forth in Scheme 1, below:

Scheme 1: Proposed Hydrolysis of Marizomib

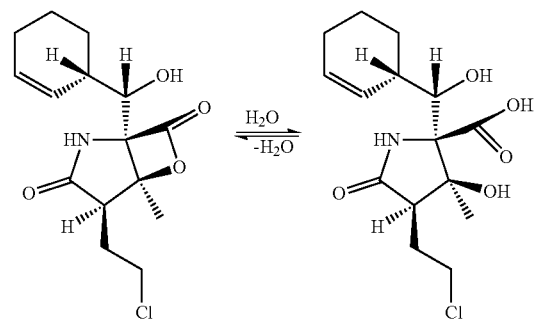

However, as shown in FIGS. 26 and 27, the spectral characterization before and after attempted hydrolysis was substantially similar. Without wishing to be bound by theory, it is proposed that the hydrolysed product crystallizes in the same morphic form as the starting material (Form I). Alternatively, without wishing to be bound by theory, it is proposed that the hydrolysis product (above) is more soluble in aqueous media and does not crystallize under the same conditions as marizomib itself. In other words, XRPD could not be used to distinguish between morphic Form I and the hydrolysis product.

Methods of Preparing Morphic Form I

Morphic Form I of marizomib can be prepared by a number of methods as set forth herein. In one embodiment, marizomib is dissolved in a solvent (e.g., acetone) and crystallization is initiated by addition of an anti-solvent (e.g., heptane).

In some embodiments, the solvent is selected from the group consisting of n-heptane, ethyl acetate, methyl-isobutyl ketone, 2-propanol, acetone, chloroform, dimethyl sulfoxide, tert-butyl methyl ether, anisole, cumene, methyl ethyl ketone, isopropyl acetate, dimethylformamide, toluene, tetrahydrofuran, dichloromethane, acetonitrile, nitromethane, ethanol, and dimethylacetamide.

Without wishing to be bound by theory, a morphic form of a compound (e.g., marizomib) does not have to fully dissolve to convert to a new polymorphic form of the compound in an anti-solvent. In some embodiments, anti-solvents can lead to new polymorphs. Without wishing to be bound by theory, even if an anti-solvent is incapable of dissolving 1/50 its volume of marizomib, a small yet appreciable amount of marizomib can still be dissolved in the anti-solvent. Without wishing to be bound by theory, as a small amount of drug (e.g., marizomib) dissolves and then precipitates, the solvent characteristics can lead to a new form (in some embodiments called a seed) in the precipitate. As the drug (e.g., marizomib) dissolves and precipitates to the new form, over time or near-complete or in some embodiments complete conversion to a new form can be observed. Without wishing to be bound by theory, such interconversion was not observed following the morphic form screen set forth herein. That is, only morphic Form I was observed when exposing Form I to both solvents and anti-solvents.

Methods of Using Morphic Form I

In some embodiments, morphic Form I of the present disclosure can be used for the treatment of a disease. For instance, morphic Form I can be used in the manufacture of a medicament for the treatment of a disease. Additionally, the present disclosure contemplates a pharmaceutical composition comprising morphic Form I and a pharmaceutically acceptable carrier.

In some embodiments, the disease is cancer or a neoplastic disease. In some embodiments, the neoplastic disease treated by the morphic Forms disclosed herein may be a cancer selected from breast cancer, sarcoma, leukemia, ovarian cancer, uretal cancer, bladder cancer, prostate cancer, colon cancer, rectal cancer, stomach cancer, lung cancer, lymphoma, multiple myeloma, pancreatic cancer, liver cancer, kidney cancer, endocrine cancer, skin cancer, melanoma, angioma, and brain or central nervous system (CNS) cancer. In one embodiment, the neoplastic disease is a multiple myeloma.

Salt and Co-Crystal Screen

As set forth in Example 12 and Table 18, approximately 117 screening experiments were conducted using 46 coformers/counterions targeting salts and cocrystal of marizomib (Sample 4). Experiments were conducted at various stoichiometric ratios using standard crystallization techniques, including cooling, evaporation, anti-solvent addition, reaction crystallization, slurry at ambient and elevated temperature, solvent assisted grinding or a combination of these techniques. Solids isolated from screening experiments were analyzed by XRPD and/or $^1$HNMR and compared to the known XRPD pattern of marizomib and representative XRPD patterns of the coformer/counterion.

Cocrystal screening of marizomib was conducted using primarily pharmaceutically acceptable coformers containing a diverse range of complementary functional groups including carboxylic acids, amino acids, amines, sulfonamides and amides that could potentially form supramolecular heterosynthons that could compete with the 2-point recognition amide-amide interaction present within the crystal structure of marizomib. However, solids isolated from cocrystal screening experiments were primarily consistent with marizomib, coformer, or mixtures of marizomib and coformer, indicating cocrystal formation did not occur under the tested experimental conditions. The detailed conditions and observations of all attempted cocrystal formation experiments and the results from PLM and XRPD analysis are summarized in Table 18.

Additional coformers such as pyroglutamic acid, 2-pyrrolidone and cytosine that contain secondary amides groups similar to marizomib were explored. Additionally, coformers that contain the 2-aminopyridine moiety e.g. adenine and melamine, were also included in screening.

Figure 41:
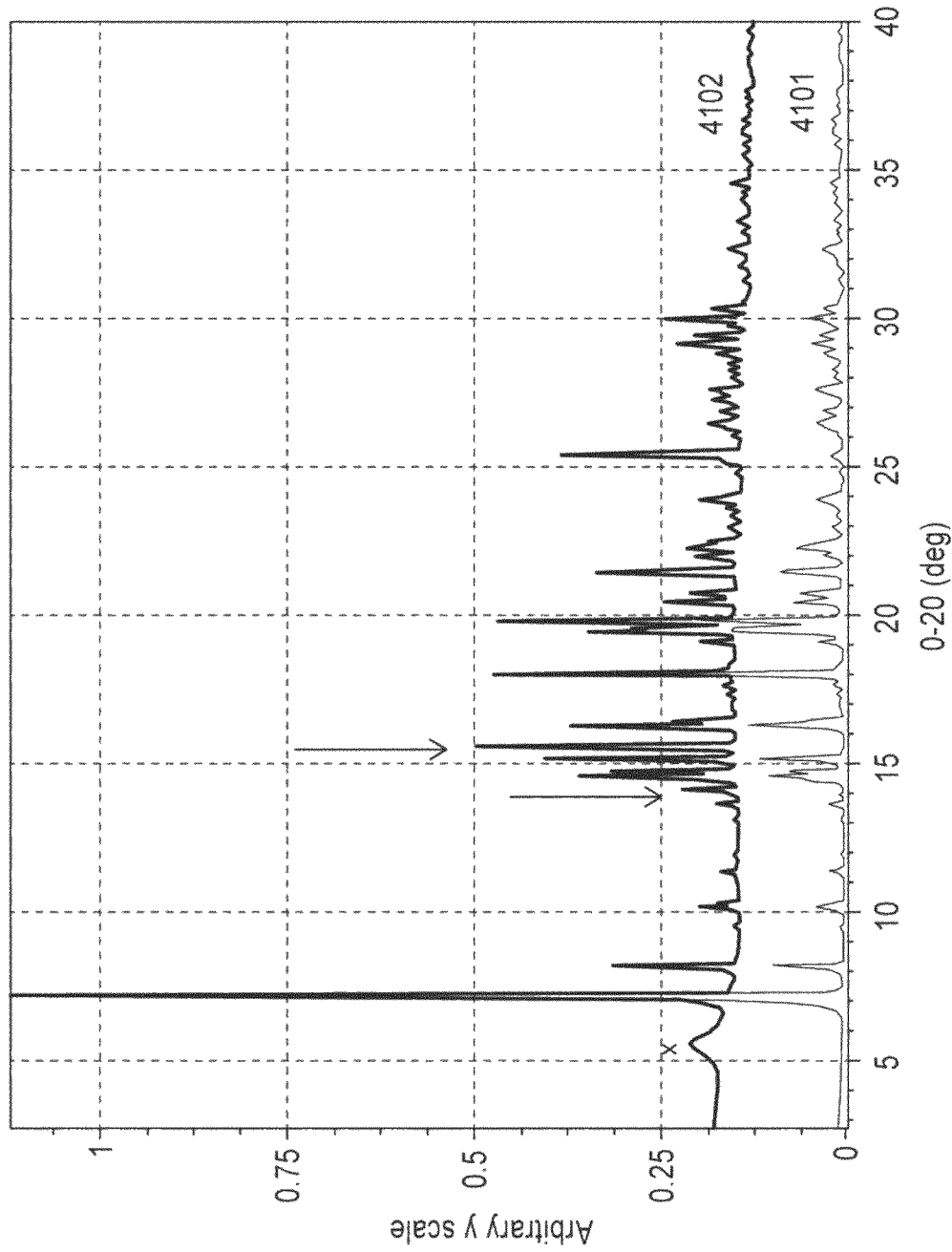
FIG. 41 is an overlay of an XRPD pattern of marizomib with solids from the 2-pyrrolidone experiment described in Example 12.
Figure 45:
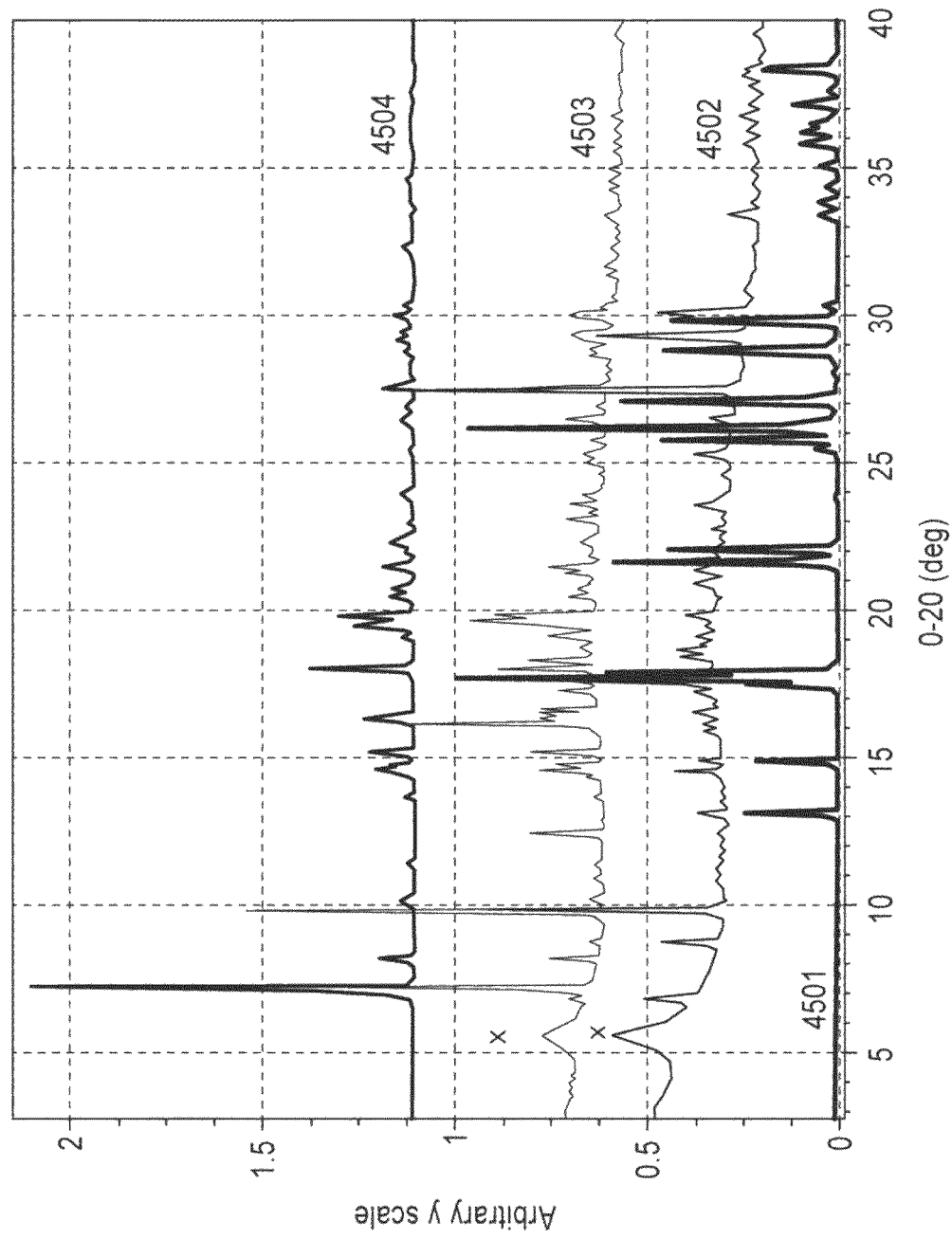
FIG. 45 is an overlay of XRPD patterns of marizomib with the solids of the melamine 1:1 and 1:3 experiments described in Example 12.
Figure 46:
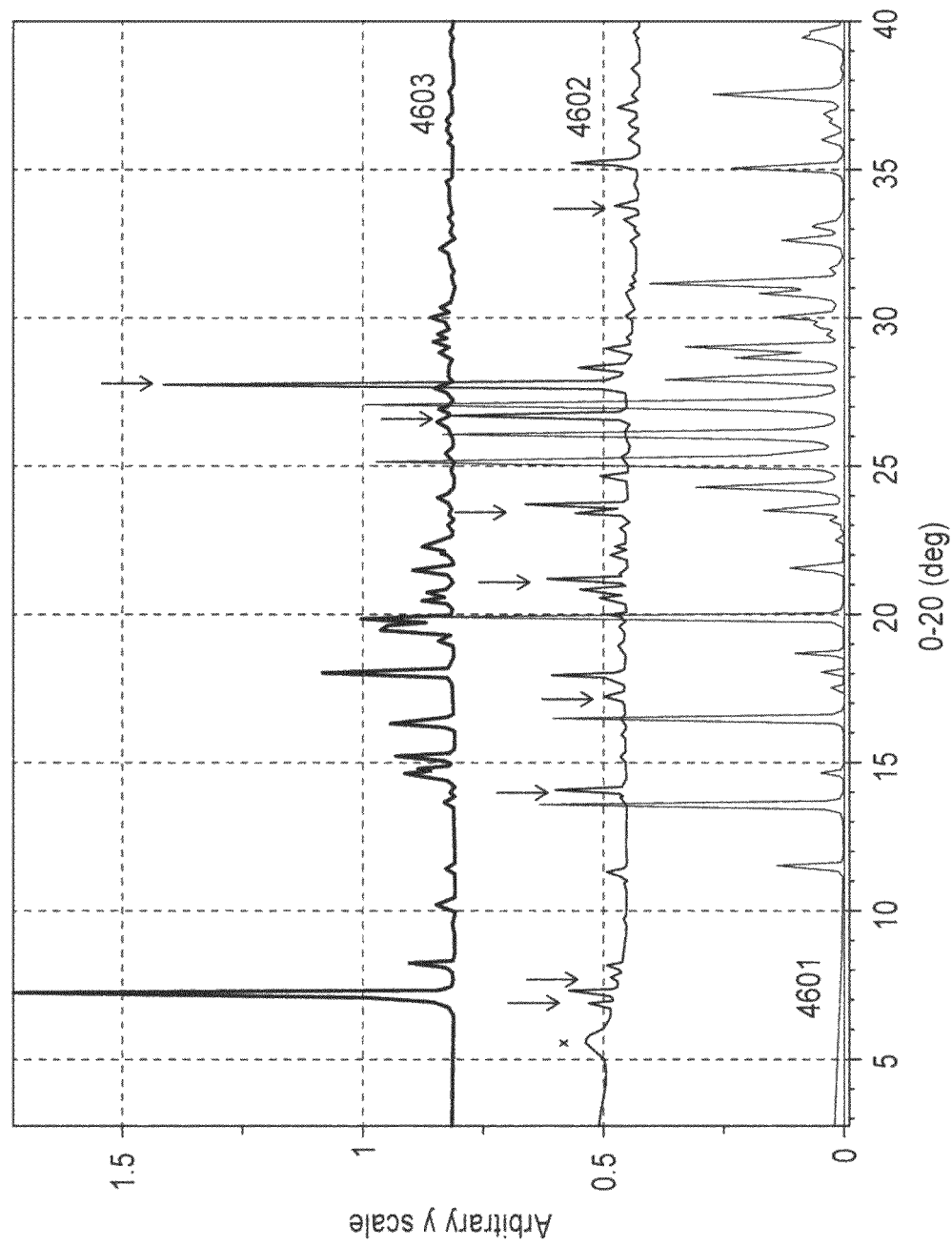
FIG. 46 is an overlay of XRPD patterns of marizomib with solids from the cytosine experiments described in Example 12.

Unique peaks in the presence of marizomib and/or coformer were identified from experiments involving marizomib with several coformers including 2-pyrrolidone (FIG. 41), melamine (FIG. 43, FIG. 45), and cytosine (FIG. 46).

Figure 42:
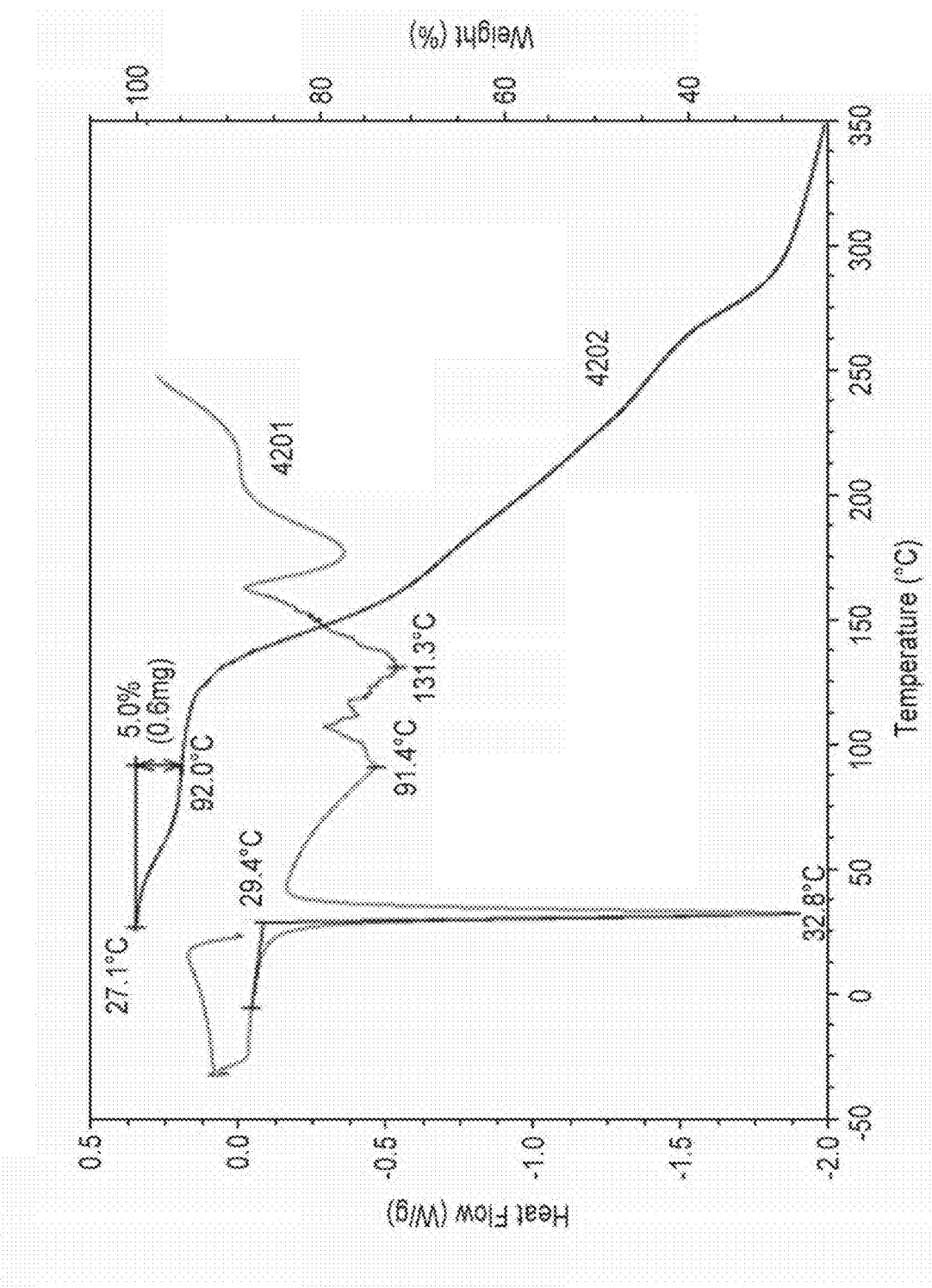
FIG. 42 is a thermal analysis of solids from —pyrrolidone experiment described in Example 12.

A mixture of marizomib and a unique material (FIG. 41), as evidenced by the two additional diffraction peaks at 14.1 and 15.5°2θ, was crystallized after slow evaporation of a hazy solution produced from a temperature cycling (50° C. to RT) experiment in acetone containing equimolar amounts of marizomib and 2-pyrrolidone. Trace 4101 shows marizomib Sample 4. Trace 4102 shows a trace of marizomib and 2-pyrrolidone (1:1) after slow evaporation after temperature cycles between 50° C. and room temperature (4 cycles). The proton NMR spectrum of solids isolated from this experiment showed marizomib: 2-pyrrolidone in approximate 1:1.2 mole ratio. Thermal analysis of solids isolated from this experiment is presented in FIG. 42. Trace 4201 shows the heat flow (W/g). Trace 4202 shows the weight percent of the sample. A sharp endotherm was observed at 32.8° C. (peak maximum), likely attributed to the melting of residual 2-pyrrolidone, followed by broad endothermic events at 91.4° C. and 131.3° C. (peak maxima) in the DSC data. By TGA, a weight loss of 5% was observed upon heating between 27° C. and 92° C. and a change in the slope after approximately 120° C. likely due to decomposition was seen. The thermal behavior for this material was different from that observed for marizomib Sample 4 used as starting material. As noted herein, marizomib Sample 4 exhibits a negligible weight loss prior to decomposition after approximately 150° C. and no thermal events are observed in the DSC data up to approximately 166° C., where an exotherm is observed followed by a small endotherm at approximately 175° C.

Grinding marizomib in a mortar and pestle in the presence of 2-pyrrolidone also produced the same unique peaks observed in the solution based experiment, in addition to peaks which were characteristic of marizomib. A third experiment was conducted in which marizomib was dissolved in 2-pyrrolidone at 50° C., cooled to RT and evaporated. However, no solids were produced and the clear solution remained.

Figure 43:
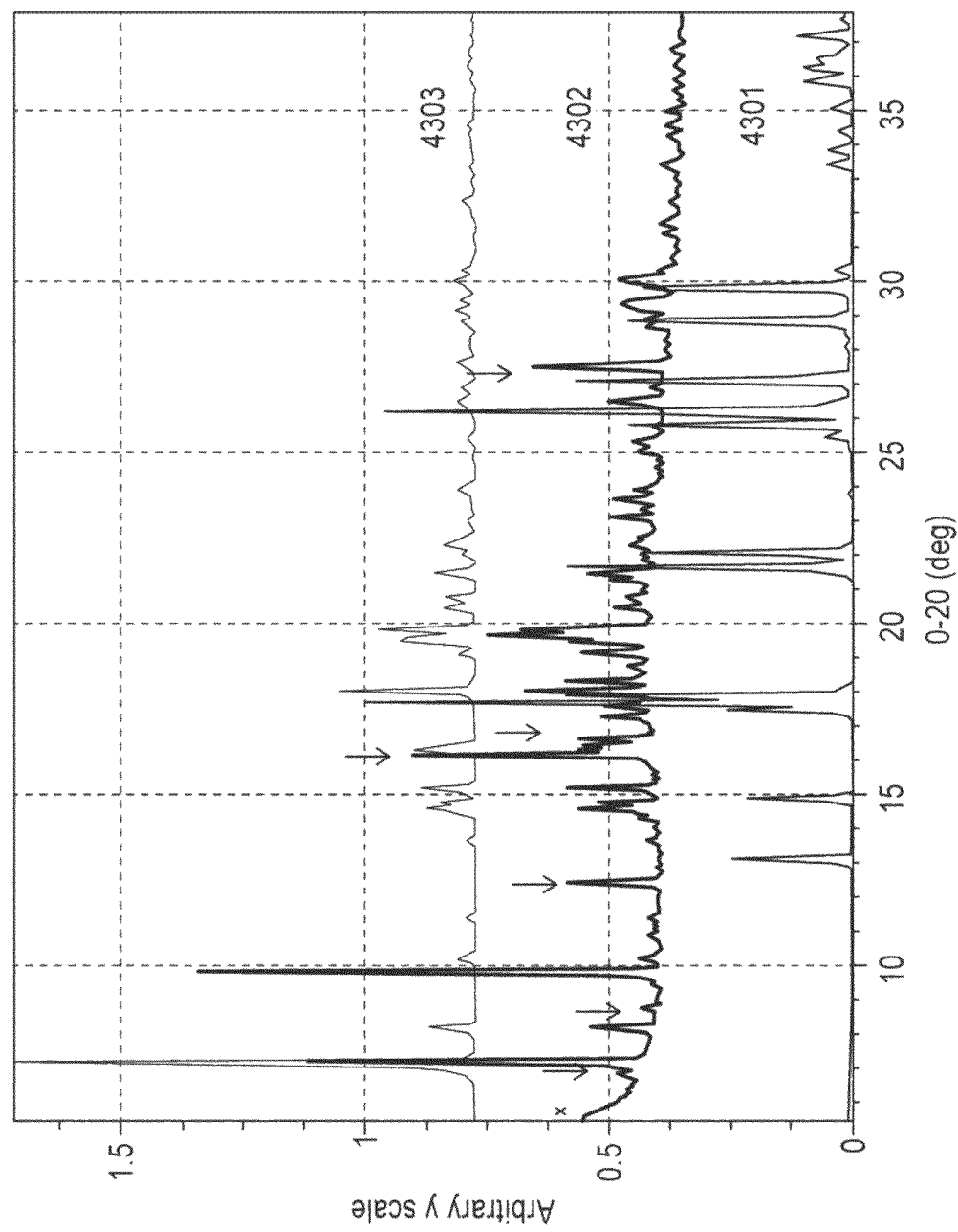
FIG. 43 is an Overlay of an XRPD pattern of marizomib with solids from the melamine experiment described in Example 12.
Figure 44:
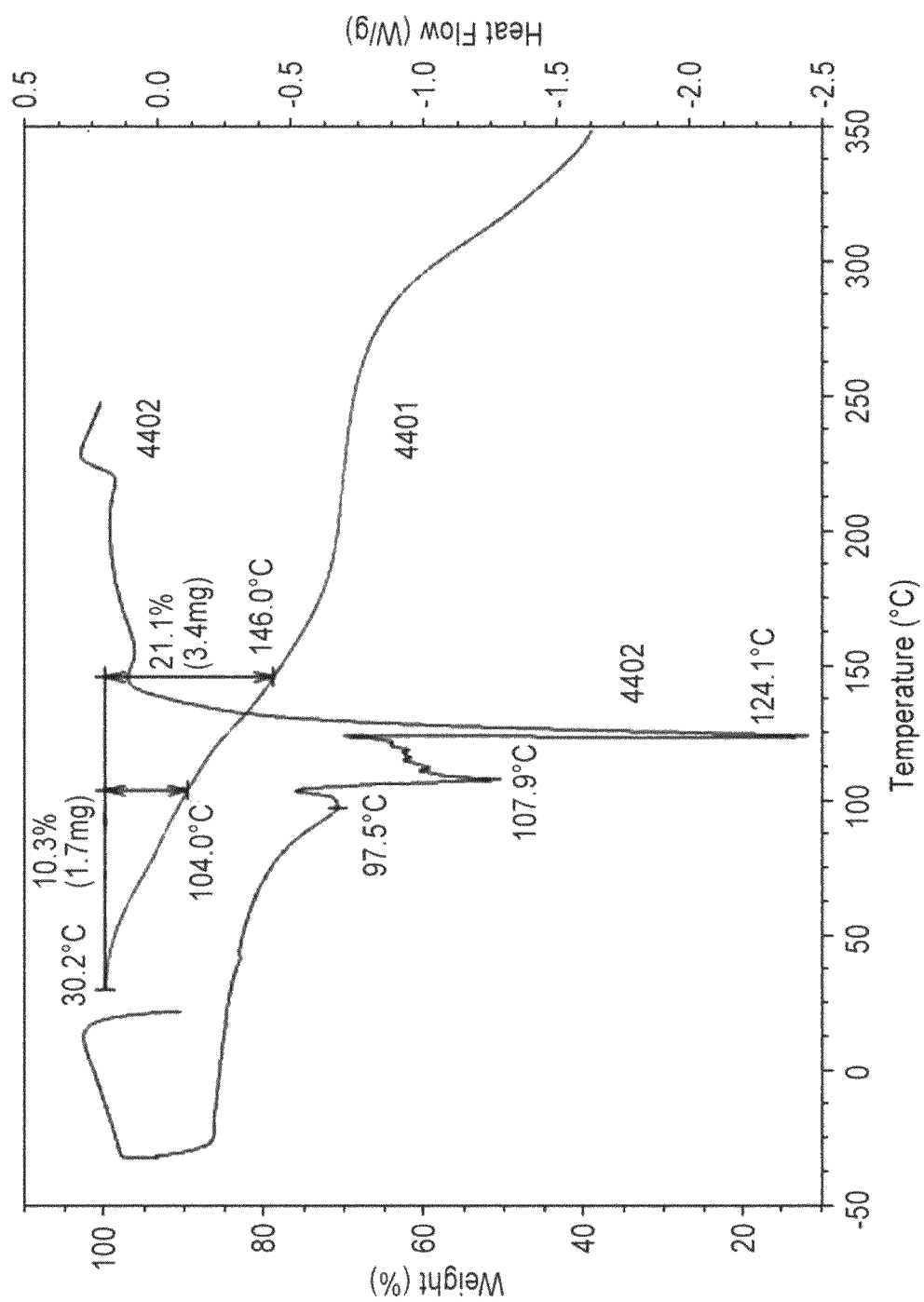
FIG. 44 is a thermal analysis of solids the melamine experiment described in Example 12.

A suspension containing equimolar amounts of marizomib and melamine in DMSO:H$_2$O (1:1) was slurried at 50° C. for approximately 2 days then at RT for 6 days and produced a mixture of marizomib and a unique material based on XRPD. The acquired proton NMR spectrum of the material from the experiment showed marizomib:melamine in approximate 1:1.6 mole ratio. Additional peaks, not present in the proton NMR spectrum of marizomib Sample 4 used as starting material were also observed, suggesting possible degradation of the marizomib. DMSO and water were also detected in the spectrum. An overlay of XRPD patterns is shown in FIG. 43. Trace 4301 shows a melamine reference. Trace 4302 shows the mixture of marizomib and melamine (1:1) slurry. Trace 4303 shows a trace of marizomib Sample 4 for reference. Thermal analysis of solids isolated from this experiment is presented in FIG. 44. Trace 4401 shows the weight percent of the sample. Trace 4402 shows the heat flow (W/g). Multiple endotherms are observed at 97.5° C., 107.9° C., and 124.1° C. (peak maxima). Note: no thermal events are observed in the DSC data for marizomib up to approximately 166° C., where an exotherm is observed followed by a small endotherm at approximately 175° C. Melamine is reported to have a melting point around 345° C. The TGA thermogram shows continuous weight loss with heating. Approximately 10% weight loss is observed between ~30° C. and 104° C. associated with the broad endotherm at 97.5° C. (peak max.) in the DSC data.

A second experiment containing marizomib and an excess of melamine (1:3 mole ratio) was performed in an attempt to isolate the unique material as a single crystalline phase. The sample was slurried overnight at 60° C. then at RT for 1 day and produced a mixture of marizomib and melamine with unique peaks (FIG. 45). Trace 4501 shows a melamine reference. Trace 4502 shows marizomib:melamine (1:3) after slurry at 60° C. in DMSO:H$_2$O (1:1) and then room temperature for 1 day. Trace 4503 shows marizomib:melamine (1:1) after slurry at 50° C. in DMSO:H$_2$O (1:1) for two days and then room temperature for 6 days. Trace 4504 shows marizomib Sample 4 for reference.

A suspension containing marizomib and an excess of cytosine (1:3 mole ratio) in dioxane:water was slurried at 60° C. overnight and produced a light yellow clear solution. After stirring at RT for 1 day, solids precipitated. Based on XRPD, the isolated solids were composed of a mixture of unique peaks and marizomib suggesting the presence of a secondary unidentified phase (FIG. 46). Trace 4601 shows an XPRD pattern of cytosine. Trace 4602 shows a pattern of marizomib:cytosine (1:3) after slurry at 60° C. overnight and then at room temperature for 1 day. Trace 4603 shows an XRPD spectrum of marizomib Sample 4. Proton NMR analysis of the solids from the experiment revealed primarily cytosine with trace marizomib and minor additional peaks. Dioxane was also observed. The data suggest no cocrystal formation occurred with cytosine and that the unique peaks are possibly attributable to a form of cytosine.

In a few cases, additional unidentified peaks were observed as a mixture with marizomib and/or coformer/counterion, and were likely due to partial degradation.

Based on the chemical structure of marizomib, the formation of stable salts of the compound was anticipated to be unlikely (predicted pKa ~−1.4), but the use of strong acids was included within the screen to evaluate possible salt formation. Salt screening attempts with sulfonic acids and mineral acids produced marizomib, mixtures of marizomib and counterion, or discolored solutions suggesting possible degradation (Example 13, Table 19). No crystalline salt of marizomib was produced in this study.

Pharmaceutical Compositions

In some embodiments, the present disclosure relates to a pharmaceutical composition comprising physiologically acceptable surface active agents, carriers, diluents, excipients, smoothing agents, suspension agents, film forming substances, and coating assistants, or a combination thereof; and morphic Form I. Acceptable carriers or diluents for therapeutic use are well known in the pharmaceutical art, and are described, for example, in Remington's Pharmaceutical Sciences, 18th Ed., Mack Publishing Co., Easton, Pa. (1990), which is incorporated herein by reference in its entirety. Preservatives, stabilizers, dyes, sweeteners, fragrances, flavoring agents, and the like may be provided in the pharmaceutical composition. For example, sodium benzoate, ascorbic acid and esters of p-hydroxybenzoic acid may be added as preservatives. In addition, antioxidants and suspending agents may be used. In various embodiments, alcohols, esters, sulfated aliphatic alcohols, and the like may be used as surface active agents; sucrose, glucose, lactose, starch, crystallized cellulose, mannitol, light anhydrous silicate, magnesium aluminate, magnesium methasilicate aluminate, synthetic aluminum silicate, calcium carbonate, sodium acid carbonate, calcium hydrogen phosphate, calcium carboxymethyl cellulose, and the like may be used as excipients; magnesium stearate, talc, hardened oil and the like may be used as smoothing agents; coconut oil, olive oil, sesame oil, peanut oil, soya may be used as suspension agents or lubricants; cellulose acetate phthalate as a derivative of a carbohydrate such as cellulose or sugar, or methylacetate-methacrylate copolymer as a derivative of polyvinyl may be used as suspension agents; and plasticizers such as ester phthalates and the like may be used as suspension agents.

Unless otherwise defined, a "solvent" of marizomib is a substance that can dissolve at least 1/50 its volume of marizomib at 50° C. or below. Unless otherwise defined, an "anti-solvent" is any substance that fails to dissolve at least 1/50 its volume of marizomib at 50° C.

The term "pharmaceutical composition" refers to morphic Form I in combination with other chemical components, such as diluents or carriers. The pharmaceutical composition facilitates administration of the compound (e.g., a morphic Form such as morphic Form I) to an organism. Multiple techniques of administering a compound exist in the art including, but not limited to, oral, injection, aerosol, parenteral, and topical administration. Pharmaceutical compositions can also be obtained by reacting compounds (e.g., a morphic Form such as morphic Form I) with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "carrier" defines a chemical compound that facilitates the incorporation of a compound (e.g., morphic Form I) into cells or tissues. For example dimethyl sulfoxide (DMSO) is a commonly utilized carrier as it facilitates the uptake of many organic compounds into the cells or tissues of an organism.

The term "diluent" defines chemical compounds diluted in water that will dissolve the compound of interest (e.g., a morphic Form such as morphic Form I) as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound.

The term "physiologically acceptable" defines a carrier or diluent that does not abrogate the biological activity and properties of the compound.

The pharmaceutical compositions described herein can be administered to a human patient per se, or in pharmaceutical compositions where they are mixed with suitable carriers or excipient(s). Techniques for formulation and administration of the compounds of the instant application may be found in "Remington's Pharmaceutical Sciences," Mack Publishing Co., Easton, Pa., 18th edition, 1990.

Suitable routes of administration may, for example, include oral, rectal, transmucosal, topical, or intestinal administration; parenteral delivery, including intramuscular, subcutaneous, intravenous, intramedullary injections, as well as intrathecal, direct intraventricular, intraperitoneal, intranasal, or intraocular injections. The morphic Forms (e.g., morphic Form I) can also be administered in sustained or controlled release dosage forms, including depot injections, osmotic pumps, pills, transdermal (including electrotransport) patches, and the like, for prolonged and/or timed, pulsed administration at a predetermined rate.

The pharmaceutical compositions of the present invention may be manufactured in a manner that is itself known, e.g., by means of conventional mixing, dissolving, granulating, dragee-making, levigating, emulsifying, encapsulating, entrapping or tabletting processes.

Pharmaceutical compositions for use in accordance with the present invention thus may be formulated in conventional manner using one or more physiologically acceptable carriers comprising excipients and auxiliaries which facilitate processing of the active compounds (e.g., a morphic Form such as morphic Form I) into preparations which can be used pharmaceutically. Proper formulation is dependent upon the route of administration chosen. Any of the well-known techniques, carriers, and excipients may be used as suitable and as understood in the art; e.g., in Remington's Pharmaceutical Sciences, above.

Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. Physiologically compatible buffers include, but are not limited to, Hanks's solution, Ringer's solution, or physiological saline buffer. If desired, absorption enhancing preparations (for example, liposomes), may be utilized.

For transmucosal administration, penetrants appropriate to the barrier to be permeated may be used in the formulation.

Pharmaceutical formulations for parenteral administration, e.g., by bolus injection or continuous infusion, include aqueous solutions of the active compounds (e.g., a morphic Form such as morphic Form I) in water-soluble form. Additionally, suspensions of the active compounds (e.g., a morphic Form such as morphic Form I) may be prepared as appropriate oily injection suspensions. Suitable lipophilic solvents or vehicles include fatty oils such as sesame oil, or other organic oils such as soybean, grapefruit or almond oils, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents that increase the solubility of the compounds (e.g., a morphic Form such as morphic Form I) to allow for the preparation of highly concentrated solutions. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

For oral administration, the compounds (e.g., a morphic Form such as morphic Form I) can be formulated readily by combining the active compounds with pharmaceutically acceptable carriers well known in the art. Such carriers enable the morphic Forms (e.g., morphic Form I) to be formulated as tablets, pills, dragees, capsules, liquids, gels, syrups, slurries, suspensions and the like, for oral ingestion by a patient to be treated. Pharmaceutical preparations for oral use can be obtained by combining the morphic Forms (e.g., morphic Form I) with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuff or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the morphic Forms (e.g., morphic Form I) may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds (e.g., a morphic Form such as morphic Form I) for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound (e.g., a morphic Form such as morphic Form I) and a suitable powder base such as lactose or starch.

Further disclosed herein are various pharmaceutical compositions well known in the pharmaceutical art for uses that include intraocular, intranasal, and intraauricular delivery. Suitable penetrants for these uses are generally known in the art. Pharmaceutical compositions for intraocular delivery include aqueous ophthalmic solutions of the morphic Forms (e.g., morphic Form I) in water-soluble form, such as eyedrops, or in gellan gum (Shedden et al., *Clin. Ther.*, 23(3):440-50 (2001)) or hydrogels (Mayer et al., *Ophthalmologica*, 210(2):101-3 (1996)); ophthalmic ointments; ophthalmic suspensions, such as microparticulates, drug-containing small polymeric particles that are suspended in a liquid carrier medium (Joshi, A., J. *Ocul. Pharmacol.* 10(1): 29-45 (1994)), lipid-soluble formulations (Alm et al., *Prog. Clin. Biol. Res.* 312:447-58 (1989)), and microspheres (Mordenti, *Toxicol. Sci.,* 52(1):101-6 (1999)); and ocular inserts. All of the above-mentioned references, are incorporated herein by reference in their entireties. Such suitable pharmaceutical formulations are most often and preferably formulated to be sterile, isotonic and buffered for stability and comfort. Pharmaceutical compositions for intranasal delivery may also include drops and sprays often prepared to simulate in many respects nasal secretions to ensure maintenance of normal ciliary action. As disclosed in Remington's Pharmaceutical Sciences, 18th Ed., Mack Publishing Co., Easton, Pa. (1990), which is incorporated herein by reference in its entirety, and well-known to those skilled in the art, suitable formulations are most often and preferably isotonic, slightly buffered to maintain a pH of 5.5 to 6.5, and most often and preferably include antimicrobial preservatives and appropriate drug stabilizers. Pharmaceutical formulations for intrarticular delivery include suspensions and ointments for topical application in the ear. Common solvents for such aural formulations include glycerin and water.

The morphic Forms (e.g., morphic Form I) may also be formulated in rectal compositions such as suppositories or retention enemas, e.g., containing conventional suppository bases such as cocoa butter or other glycerides.

In addition to the formulations described previously, the morphic Forms (e.g., morphic Form I) may also be formulated as a depot preparation. Such long acting formulations may be administered by implantation (for example subcutaneously or intramuscularly) or by intramuscular injection. Thus, for example, the compounds (e.g., a morphic Form such as morphic Form I) may be formulated with suitable polymeric or hydrophobic materials (for example as an emulsion in an acceptable oil) or ion exchange resins, or as sparingly soluble derivatives, for example, as a sparingly soluble salt.

In some embodiments, a suitable pharmaceutical carrier may be a cosolvent system comprising benzyl alcohol, a nonpolar surfactant, a water-miscible organic polymer, and an aqueous phase. A common cosolvent system used is the VPD co-solvent system, which is a solution of 3% w/v benzyl alcohol, 8% w/v of the nonpolar surfactant Polysorbate 80™, and 65% w/v polyethylene glycol 300, made up to volume in absolute ethanol. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of POLYSORBATE 80™; the fraction size of polyethylene glycol may be varied; other biocompatible polymers may replace polyethylene glycol, e.g., polyvinyl pyrrolidone; and other sugars or polysaccharides may substitute for dextrose.

Alternatively, other delivery systems for hydrophobic pharmaceutical compounds (e.g., a morphic Form such as morphic Form I) may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds (e.g., a morphic Form such as morphic Form I) may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

Agents intended to be administered intracellularly may be administered using techniques well known to those of ordinary skill in the art. For example, such agents may be encapsulated into liposomes. All molecules present in an aqueous solution at the time of liposome formation are incorporated into the aqueous interior. The liposomal contents are both protected from the external micro-environment and, because liposomes fuse with cell membranes, are efficiently delivered into the cell cytoplasm. The liposome may be coated with a tissue-specific antibody. The liposomes will be targeted to and taken up selectively by the desired organ. Alternatively, small hydrophobic organic molecules may be directly administered intracellularly.

Additional therapeutic or diagnostic agents may be incorporated into the pharmaceutical compositions. Alternatively or additionally, pharmaceutical compositions may be combined with other compositions that contain other therapeutic or diagnostic agents.

Methods of Administration

The morphic Forms (e.g., morphic Form I) and pharmaceutical compositions comprising the same may be administered to the patient by any suitable means. Non-limiting examples of methods of administration include, among others, (a) administration though oral pathways, which administration includes administration in capsule, tablet, granule, spray, syrup, or other such forms; (b) administration through non-oral pathways such as rectal, vaginal, intraurethral, intraocular, intranasal, or intraauricular, which administration includes administration as an aqueous suspension, an oily preparation or the like or as a drip, spray, suppository, salve, ointment or the like; (c) administration via injection, subcutaneously, intraperitoneally, intravenously, intramuscularly, intradermally, intraorbitally, intracapsularly, intraspinally, intrasternally, or the like, including infusion pump delivery; (d) administration locally such as by injection directly in the renal or cardiac area, e.g., by depot implantation; as well as (e) administration topically; as deemed appropriate by those of skill in the art for bringing the compound of the invention (e.g., a morphic Form such as morphic Form I) into contact with living tissue.

Pharmaceutical compositions suitable for administration include compositions where the active ingredients are contained in an amount effective to achieve its intended purpose. The therapeutically effective amount of the compounds disclosed herein (e.g., a morphic Form such as morphic Form I) required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize. More specifically, a therapeutically effective amount means an amount of compound (e.g., a morphic Form such as morphic Form I) effective to prevent, alleviate or ameliorate symptoms of disease or prolong the survival of the subject being treated. Determination of a therapeutically effective amount is well within the capability of those skilled in the art, especially in light of the detailed disclosure provided herein.

As will be readily apparent to one skilled in the art, the useful in vivo dosage to be administered and the particular mode of administration will vary depending upon the age, weight and mammalian species treated, the particular compounds employed (e.g., a morphic Form such as morphic Form I), and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

In non-human animal studies, applications of potential products are commenced at higher dosage levels, with dosage being decreased until the desired effect is no longer achieved or adverse side effects disappear. The dosage may range broadly, depending upon the desired affects and the therapeutic indication. Typically, dosages may be between about 10 microgram/kg and 100 mg/kg body weight, preferably between about 100 microgram/kg and 10 mg/kg body weight. Alternatively dosages may be based and calculated upon the surface area of the patient, as understood by those of skill in the art.

The exact formulation, route of administration and dosage for the pharmaceutical compositions of the present invention can be chosen by the individual physician in view of the patient's condition. (See e.g., Fingl et al. 1975, in "The Pharmacological Basis of Therapeutics", which is hereby incorporated herein by reference in its entirety, with particular reference to Ch. 1, p. 1). Typically, the dose range of the composition administered to the patient can be from about 0.5 to 1000 mg/kg of the patient's body weight. The dosage may be a single one or a series of two or more given in the course of one or more days, as is needed by the patient. In instances where human dosages for compounds (e.g., a morphic Form such as morphic Form I) have been established for at least some condition, the present invention will use those same dosages, or dosages that are between about 0.1% and 500%, more preferably between about 25% and 250% of the established human dosage. Where no human dosage is established, as will be the case for newly-discovered pharmaceutical compounds, a suitable human dosage can be inferred from $ED_{50}$ or $ID_{50}$ values, or other appropriate values derived from in vitro or in vivo studies, as qualified by toxicity studies and efficacy studies in animals.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Although the exact dosage will be determined on a drug-by-drug basis, in most cases, some generalizations regarding the dosage can be made. The daily dosage regimen for an adult human patient may be, for example, an oral dose of between 0.1 mg and 2000 mg of each active ingredient, preferably between 1 mg and 500 mg, e.g. 5 to 200 mg. In other embodiments, an intravenous, subcutaneous, or intramuscular dose of each active ingredient of between 0.01 mg and 100 mg, preferably between 0.1 mg and 60 mg, e.g. 1 to 40 mg is used. In cases of administration of a pharmaceutically acceptable salt, dosages may be calculated as the free base. In some embodiments, the composition is administered 1 to 4 times per day. Alternatively the compositions of the invention may be administered by continuous intravenous infusion, preferably at a dose of each active ingredient up to 1000 mg per day. As will be understood by those of skill in the art, in certain situations it may be necessary to administer the compounds disclosed herein (e.g., a morphic Form such as morphic Form I) in amounts that exceed, or even far exceed, the above-stated, preferred dosage range in order to effectively and aggressively treat particularly aggressive diseases or infections. In some embodiments, the compounds (e.g., a morphic Form such as morphic Form I) will be administered for a period of continuous therapy, for example for a week or more, or for months or years.

Dosage amount and interval may be adjusted individually to provide plasma levels of the active moiety which are sufficient to maintain the modulating effects, or minimal effective concentration (MEC). The MEC will vary for each compound (e.g., a morphic Form such as morphic Form I) but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. Compositions should be administered using a regimen which maintains plasma levels above the MEC for 10-90% of the time, preferably between 30-90% and most preferably between 50-90%.

In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

Compounds disclosed herein (e.g., a morphic Form such as morphic Form I) can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds (e.g., a morphic Form such as morphic Form I) in an animal model, such as mice, rats, rabbits, or monkeys, may be determined using known methods. The efficacy of a particular compound may be established using several recognized methods, such as in vitro methods, animal models, or human clinical trials. Recognized in vitro models exist for nearly every class of condition, including but not limited to cancer, cardiovascular disease, and various immune dysfunction. Similarly, acceptable animal models may be used to establish efficacy of chemicals to treat such conditions. When selecting a model to determine efficacy, the skilled artisan can be guided by the state of the art to choose an appropriate model, dose, and route of administration, and regime. Of course, human clinical trials can also be used to determine the efficacy of a compound (e.g., a morphic Form such as morphic Form I) in humans.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising a compound of the invention formulated in a compatible pharmaceutical carrier may also be prepared, placed in an appropriate container, and labeled for treatment of an indicated condition.

EXAMPLES

The disclosure is further illustrated by the following examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Abbreviations used herein are given below:

| Acronym | Meaning |
| --- | --- |
| ca. | Approximately |
| DMA | Dimethylacetamide |
| DMF | Dimethylformamide |
| DSC | Differential Scanning Calorimetry |
| H$_2$O | Water |
| $^1$H-NMR | Proton Nuclear Magnetic Resonance |
| HPLC | High Performance Liquid Chromatography |
| ID | Identification |
| MeCN | Acetonitrile |
| MEK | Methyl Ethyl Ketone |
| MeOH | Methanol |
| MIBK | Methyl Isobutyl Ketone |
| N/A | Not Applicable |
| PLM | Polarised Light Microscopy |
| RT | Room Temperature |
| SCXRD | Single Crystal X-Ray Diffraction |
| SEM | Scanning Electron Microscope |
| TGA | Thermal Gravimetric Analysis |
| UV | Ultra Violet |
| VT-XRPD | Variable Temperature X-Ray Powder Diffraction |
| XRPD | X-Ray Powder Diffraction |

Analytical Techniques

| Acronyms | Full Name/Description |
| --- | --- |
| DSC | Differential scanning calorimetry |
| mDSC | Modulated differential scanning calorimetry |
| NMR | Nuclear magnetic resonance spectroscopy |
| TGA | Thermogravimetric analysis |
| XRPD | X-ray powder diffraction |
| DVS | Dynamic vapor sorption |

Methods

| Acronym | Full Name/Description |
| --- | --- |
| CC | Crash cooling |
| CP | Crash precipitation |
| FC | Fast cooling |
| FE | Fast evaporation |
| SC | Slow cooling |

Miscellaneous

| Acronym | Full Name/Description |
| --- | --- |
| Agg. (agg.) | Aggregates |
| Agg. (agg.) | Aggregates |
| API | Active pharmaceutical ingredient |
| B/E | Birefringence and extinction |
| B | Birefringence |
| d | Day(s) |
| decomp. | Decomposition |
| endo | Endotherm |
| exo | Exotherm |
| h | Hour(s) |
| LIMS | Laboratory information management system |

-continued

| Acronym | Full Name/Description |
| --- | --- |
| RT | Room temperature/ambient temperature |
| UM | Unknown morphology |
| A$_w$ | water activity |
| w/ | With |
| IS | Insufficient amount |
| Anh. | Anhydrous |
| API | Active pharmaceutical ingredient |
| B | Birefringence |
| B/E | Birefringence and extinction |
| MRZ | Marizomib |
| O/N | Overnight |
| PLM | Polarized light microscope |
| RT | Room temperature/ambient temperature |
| Sat'd | Saturated |

Solvents

| Acronyms | Full Name/Description |
| --- | --- |
| [EMIm][Cl] | 1-Ethyl-3-methylimidazolium chloride |
| [EMIm][NTF$_2$] | 1-Ethyl-3-methylimidazolium bis(trifluoromethylsulfonyl)imide |
| 2-Me THF | 2-Methyltetrahydrofuran |
| ACN | acetonitrile |
| CHCl$_3$ | chloroform |
| DCM | dichloromethane |
| DMF | dimethylformamide |
| EtOAc | ethyl acetate |
| Formulation System A | 55% propylene glycol + 5% EtOH + 40% citrate buffer (10 mM; pH 5) |
| Formulation System B | 14/86 (v/v) H$_2$O/tBA containing 30 mg/ml sucrose, and titrated with HCl to pH 3.2 ± 0.2 |
| IPA | isopropyl alcohol |
| MEK | butanone (methyl ethyl ketone) |
| MeOAc | methyl acetate |
| MIBK | methyl isobutyl ketone |
| MTBE | methyl Tertiary Butyl Ether |
| NMP | N-Methyl-2-pyrrolidone |
| THF | tetrahydrofuran |
| t-BuOH | Tert-butanol |
| DMSO | Dimethylsulfoxide |
| EtOH | Ethanol |
| H2O | Water |
| H2SO4 | Sulfuric acid |
| HCl | Hydrochloric acid |
| HFIPA | 1,1,1,3,3,3-hexafluoro-2-propanol |
| IPrOAc | Isopropyl acetate |
| MeOH | Methanol |
| NMP | N-methyl-2-pyrrolidone |
| 1-PrOH | 1-propanol |
| TFE | 2,2,2-trifluoroethanol |

XRPD Terminology

The term "crystalline" is understood to mean a form that exhibits an XRPD pattern with sharp peaks (similar to instrumental peak widths) and weak diffuse scattering (relative to the peaks).

The term "disordered crystalline" is understood to mean a form that exhibits an XRPD pattern with broad peaks (relative to instrumental peak widths) and/or strong diffuse scattering (relative to the peaks). Disordered materials may be microcrystalline; crystalline with large defect density; mixtures of crystalline and x-ray amorphous phases; or a combination of the above. Additional analysis may differentiate among these options.

The term "insufficient signal" is used when insufficient signal above the expected background scattering was observed. This may indicate, for example, that the x-ray beam missed the sample and/or that the sample was of insufficient mass for analysis.

"Particle statistics artifacts" can occur when the particle size distribution contains a small number of large crystals which may in some cases lead to sharp spikes in the XRPD pattern.

"Preferred orientation artifacts" can occur when the particle morphology is prone to non-random orientation in the sample holder which may in some cases lead to changes in relative peak intensities.

"No peaks" can occur when no Bragg peaks are observed in the XRPD pattern. The absence of peaks may in some cases be due to an x-ray amorphous sample and/or insufficient signal.

"Single crystalline phase" can refer to when an XRPD pattern is judged to contain evidence of a single crystalline phase if the Bragg peaks can be indexed with a single unit cell.

"X-ray amorphous" can refer to situations in which diffuse scatter is present, but no evidence for Bragg peaks is found in an XRPD pattern. X-ray amorphous materials may be: nano-crystalline; crystalline with a very large defect density; kinetic amorphous material; thermodynamic amorphous material; or a combination of the above. Additional analysis may differentiate among these options.

Hygroscopicity

The term "low hygroscopicity" refers to samples that exhibit <0.5 weight percent water uptake over a specified relative humidity range.

The term "limited hygroscopicity" refers to samples that exhibit <2.0 weight percent water uptake over a specified relative humidity range.

The term "significant hygroscopicity" refers to samples that exhibit ≥2.0 weight percent water uptake over a specified relative humidity range.

The term "deliquescence" refers to spontaneous liquefaction associated with water sorption from atmospheric moisture.

The term "stoichiometric hydrate" refers to crystalline material with stable stoichiometric water content over an extended relative humidity range. Exemplary stoichiometric hydrates can be, for instance, hemihydrates, monohydrates, sesquihydrate, or dehydrates.

A "variable hydrate" can refer to crystalline material with variable water content over an extended relative humidity range, yet with no phase change.

Experimental Procedures

Examples 3-11 used Sample 4 of marizomib.

X-Ray Powder Diffraction (XRPD)—Samples 1-3

X-Ray Powder Diffraction patterns were collected on a Bruker AXS C2 GADDS diffractometer using Cu Kα radiation (40 kV, 40 mA), automated XYZ stage, laser video microscope for auto-sample positioning and a HiStar 2-dimensional area detector. X-ray optics consists of a single Göbel multilayer mirror coupled with a pinhole collimator of 0.3 mm. A weekly performance check was carried out using a certified standard NIST 1976 Corundum (flat plate).

The beam divergence, i.e. the effective size of the X-ray beam on the sample, was approximately 4 mm. A θ-θ continuous scan mode was employed with a sample-detector distance of 20 cm which gave an effective 2θ range of 3.2°-29.7°. Unless otherwise specified, the sample would be exposed to the X-ray beam for about 120 seconds. The software used for data collection was GADDS for XP/2000 4.1.43 and the data were analyzed and presented using Diffrac Plus EVA v15.0.0.0.

Samples run under ambient conditions were prepared as flat plate specimens using powder as received without grinding. Approximately 1-2 mg of the sample was lightly pressed on a glass slide to obtain a flat surface.

Samples run under non-ambient conditions were mounted on a silicon wafer with heat-conducting compound. The sample was then heated to the appropriate temperature at 20° C./min and subsequently held isothermally for 1 minute before data collection was initiated.

Alternatively, X-Ray Powder Diffraction patterns were collected on a Bruker D8 diffractometer using Cu Kα radiation (40 kV, 40 mA), 0-2θ goniometer, and divergence of V4 and receiving slits, a Ge monochromator and a Lynxeye detector. The instrument was performance checked using a certified Corundum standard (NIST 1976). The software used for data collection was Diffrac Plus XRD Commander v2.6.1 and the data were analysed and presented using Diffrac Plus EVA v15.0.0.0.

Samples were run under ambient conditions as flat plate specimens using powder as received. The sample was gently packed into a cavity cut into polished, zero-background (510) silicon wafer. The sample was rotated in its own plane during analysis. The details of the data collection are: Angular range: 2 to 42°2θ; Step size: 0.05°2θ; Collection time: 0.5 s/step.

X-Ray Powder Diffraction (XRPD)—Sample 4

Transmission Mode: XRPD patterns were collected with a PANalytical X'Pert PRO MPD diffractometer using an incident beam of Cu radiation produced using an Optix long, fine-focus source. An elliptically graded multilayer mirror was used to focus Cu Kα X-ray radiation through the specimen and onto the detector. Prior to the analysis, a silicon specimen (NIST SRM 640e) was analyzed to verify the observed position of the Si (111) peak is consistent with the NIST-certified position. A specimen of the sample was sandwiched between 3-µm-thick films and analyzed in transmission geometry. A beam-stop, short antiscatter extension, and antiscatter knife edge, were used to minimize the background generated by air. Soller slits for the incident and diffracted beams were used to minimize broadening from axial divergence. Diffraction patterns were collected using a scanning position-sensitive detector (X'Celerator) located 240 mm from the specimen and Data Collector software v. 2.2b.

Reflection Mode: XRPD patterns were collected with a PANalytical X'Pert PRO MPD diffractometer using an incident beam of Cu Kα radiation produced using a long, fine-focus source and a nickel filter. The diffractometer was configured using the symmetric Bragg-Brentano geometry. Prior to the analysis, a silicon specimen (NIST SRM 640c) was analyzed to verify the observed position of the Si 111 peak is consistent with the NIST-certified position. A specimen of the sample was prepared as a thin, circular layer centered on a silicon zero-background substrate. Antiscatter slits (SS) were used to minimize the background generated by air. Soller slits for the incident and diffracted beams were used to minimize broadening from axial divergence. Diffraction patterns were collected using a scanning position-sensitive detector (X'Celerator) located 240 mm from the sample and Data Collector software v. 2.2b.

A high-resolution XRPD pattern was indexed using proprietary SSCI software, TRIADS™. Indexing and structure refinement are computational studies. Agreement between the allowed peak positions, marked with red bars, and the observed peaks indicates a consistent unit cell determination. Successful indexing of the pattern indicates that the sample is composed primarily of a single crystalline phase. To confirm the tentative indexing solution, the molecular packing motifs within the crystallographic unit cells must be determined. No attempts at molecular packing were performed.

Proton Nuclear Magnetic Resonance ($^1$H-NMR)—Samples 1-3

NMR spectra were collected on a Bruker 400 MHz instrument equipped with an auto-sampler and controlled by a DRX400 console. Automated experiments were acquired using ICON-NMR v4.0.7 running with Topspin v1.3 using the standard Bruker loaded experiments. For non-routine spectroscopy, data were acquired through the use of Topspin alone.

Samples were prepared in DMSO-d$_6$, unless otherwise stated. Off-line analysis was carried out using ACD Spectus Processor 2014.

Proton Nuclear Magnetic Resonance ($^1$H-NMR)—Sample 4

Initial characterization solution proton NMR spectra were acquired with an Agilent DD2-400 spectrometer using deuterated methanol.

Other solution NMR spectra were acquired using a Bruker-Biospin 5 mm gradient broadband probe on a Bruker-Biospin AVANCE II 400 MHz NMR spectrometer. The spectrum was referenced using the tetramethylsilane resonance and set equal to 0.0 ppm. The FID was processed using Bruker TopSpin 2.1.

For the coformer screen and salt screen (Examples 12 and 13), the solution NMR spectra were acquired with an Agilent DD2-400 spectrometer. Samples were prepared by dissolving approximately 5-10 mg of sample in DMSO-d6 containing TMS. The data acquisition parameters are displayed in each plot of the spectrum in the Data section of this report.

Differential Scanning Calorimetry (DSC)—Samples 1-3

DSC data were collected on a TA Instruments Q2000 equipped with a 50-position auto-sampler. The calibration for thermal capacity was carried out using sapphire and the calibration for energy and temperature was carried out using certified indium. Typically 0.5-3 mg of each sample, in a pin-holed aluminum pan, was heated at 10° C./min from 25° C. to 300° C. A purge of dry nitrogen at 50 ml/min was maintained over the sample.

The instrument control software was Advantage for Q Series v2.8.0.394 and Thermal Advantage v5.5.3 and the data were analyzed using Universal Analysis v4.5A.

Differential scanning calorimetry experiments were performed in duplicate at each of the four heating rates (i.e., 2, 5, 10 and 50° C./min).

Differential Scanning Calorimetry (DSC)—Sample 4

DSC was performed using a TA Instruments Q2000 differential scanning calorimeter. Temperature calibration was performed using NIST-traceable indium metal. The sample was placed into an aluminum Tzero DSC pan, covered with a lid, and the weight was accurately recorded. A weighed aluminum pan configured as the sample pan was placed on the reference side of the cell.

Modular Differential Scanning Calorimetry (mDSC)—Sample 4 mDSC data was obtained on a TA Instruments 2920 differential scanning calorimeter equipped with a refrigerated cooling system (RCS). Temperature calibration was performed using NIST traceable indium metal. The sample was placed into an aluminum DSC pan, covered with a lid, and the weight was accurately recorded. A weighed aluminum pan configured as the sample pan was placed on the reference side of the cell.

Thermo-Gravimetric Analysis (TGA)—Samples 1-3

TGA data were collected on a TA Instruments Q500 TGA, equipped with a 16-position auto-sampler. The instrument was temperature calibrated using certified Alumel™ and Nickel. Typically 5-10 mg of each sample was loaded onto a pre-tared aluminum DSC pan and heated at 10° C./min from ambient temperature to 350° C. A nitrogen purge at 60 ml/min was maintained over the sample.

The instrument control software was Advantage for Q Series v2.5.0.256 and Thermal Advantage v5.5.3 and the data were analyzed using Universal Analysis v4.5A.

Thermo-Gravimetric Analysis (TGA)—Sample 4

TG analyses were performed using a TA Instruments Q5000 IR thermogravimetric analyzer. Temperature calibration was performed using nickel and Alumel™. Each sample was placed in an aluminum pan. The sample was hermetically sealed, the lid pierced, then inserted into the TG furnace. The furnace was heated under nitrogen.

Polarized Light Microscopy (PLM)—Samples 1-3

Samples were studied on a Leica LM/DM polarized light microscope with a digital video camera for image capture. A small amount of each sample was placed on a glass slide, mounted in immersion oil and covered with a glass slip, the individual particles being separated as well as possible. The sample was viewed with appropriate magnification and partially polarized light, coupled to a λ false-color filter.

Polarized Light Microscopy (PLM)—Sample 4

Light microscopy was performed using a Motic SMZ-168 stereomicroscope. Various objectives typically ranging from 0.8-10× were used with crossed-polarized light to view samples. Samples were either viewed in situ, or in a drop of mineral oil.

For the coformer screen and salt screen (Examples 12 and 13), light microscopy was performed using Fisher Scientific Stereomaster stereomicroscope. Various objectives typically ranging from 0.8-10× were used with crossed-polarized light to view samples.

Hot Stage Microscopy (HSM)

Hot Stage Microscopy was carried out using a Leica LM/DM polarised light microscope combined with a Mettler-Toledo FP82HT hot-stage and a digital video camera for image capture. A small amount of each sample was placed onto glass slide with individual particles separated as well as possible. The sample was viewed with appropriate magnification and partially polarised light, coupled to a λ false-colour filter, whilst being heated from ambient temperature typically at 10-20° C./min.

Chemical Purity Determination by HPLC

Purity analysis was performed on an Agilent HP1100 series system equipped with a diode array detector and using ChemStation software vB.04.03 using the method set forth in Table-6.

TABLE 5

HPLC Conditions for Purity Determination

| Parameter | Value | | |
|---|---|---|---|
| Type of method | Reverse phase with gradient elution | | |
| Sample Preparation | 0.5 mg/ml in acetonitrile:water 1:1 + 0.1% TFA | | |
| Column | Supelco Ascentis Express C18, 100 × 4.6 mm, 2.7 µm | | |
| Column Temperature (° C.) | 25 | | |
| injection (µl) | 5 | | |
| Wavelength, Bandwidth (nm) | 255, 90 | | |
| Flow Rate (ml/min) | 2 | | |
| Phase A | 0.1% TFA in water | | |
| Phase B | 0.085% TFA in acetonitrile | | |
| Timetable | Time (min) | % Phase A | % Phase B |
| | 0 | 95 | 5 |
| | 6 | 5 | 95 |
| | 6.2 | 95 | 5 |
| | 8 | 95 | 5 |

Example 1—Hydrolysis of Marizomib 30 mg of Sample 1 was suspended in the given solvent shown in Table 6 (1 ml) at room temperature. The samples were matured between 50° C. and room temperature heat-cool cycles (8 h per cycle) for 96 h. The solids were filtered, air dried and analyzed by XRPD.

TABLE 6

Preparation and Characterization of Solids from Hydrolysis Experiments

| Solvent | Obs. at r.t. | Obs. post maturation | XRPD | ¹H-NMR | HPLC Purity |
|---|---|---|---|---|---|
| MeOH | Suspension | Suspension | Crystalline - similar to Form I | n/a | n/a |
| Water | Suspension | Suspension | Crystalline - similar to Form 1 | Comparable with ref. spectrum | 74.8% (ref. to starting material: 98.2%) |

After 4 days maturation in water, the chemical purity was down from 98% to 75%, with emphasis on a particular peak on the HPLC chromatogram (RRT=4.75 min) as shown in FIG. 28. However, the solid phase remained the same by XRPD as shown in FIG. 26. Without wishing to be bound by theory, it is proposed that the hydrolysed product crystallizes in the same phase as the starting material (Form I). In other words, XRPD could not be used to distinguish between morphic Form I and the hydrolysis product.

Example 2—Polymorphism Screening

Polymorphism studies on marizomib were carried out in different solvents and conditions to understand the polymorphic behavior of the free form.

Marizomib (Sample 1, 30 mg) was dissolved or suspended in the given solvent at room temperature. Solvent was added until the material dissolved or up to a maximum of 50 volumes. The suspensions were matured between 50° C. and room temperature heat-cool cycles (8 h per cycle) for 24 h. The solutions were cooled to and held at 5° C. for 48 h. If no solid was obtained then the solutions were allowed to evaporate slowly at room temperature. All the recovered solids were analyzed by XRPD. The results are given in Table 7.

TABLE 7

Polymorphism Screen Results

| | Obs, at r.t. | | | | | Maturation | Cooling | Evap. | |
|---|---|---|---|---|---|---|---|---|---|
| Solvent | 10 vol. | 20 vol. | 30 vol. | 40 vol. | 50 vol. | 50° C./r.t. | at 5° C. | at r.t. | XRPD |
| n-Heptane | x | x | x | x | x | x | n/a | n/a | Form I |
| Ethyl acetate | x | x | x | x | x | ✓ | ✓ | Solid | Form I |
| MIBK | x | x | x | x | x | x | n/a | n/a | Form I |
| 2-Propanol | x | x | x | x | x | x | n/a | n/a | Form I |
| Acetone | x | x | x | x | x | ✓ | ✓ | Solid | Form I |
| Chloroform | x | ✓ | | | | | ✓ | Solid | Form I |
| Dimethyl sulfoxide | x | x | x | x | x | ✓ | ✓ | Solid | Form I |
| tert-Butylmethyl ether | x | x | x | x | x | x | n/a | n/a | Form I |
| Anisole | x | x | x | x | x | x | n/a | n/a | Form I |
| Cumene | x | x | x | x | x | x | n/a | n/a | Form I |
| MEK | x | x | x | x | x | ✓ | ✓ | Solid | Form I |
| Isopropyl acetate | x | x | x | x | x | x | n/a | n/a | Form I |
| DMF | x | ✓ | | | | | ✓ | Solution after four weeks* | |
| Toluene | x | x | x | x | x | x | n/a | n/a | Form I |
| Tetrahydrofuran | x | ✓ | | | | | ✓ | Solid | Form I |
| Dichloromethane | x | x | x | x | x | x | n/a | n/a | Form I |
| Acetonitrile | x | x | x | x | x | x | n/a | n/a | Form I |
| Nitromethane | x | x | x | x | x | x | n/a | n/a | Form I |
| Ethanol | x | x | x | x | x | x | n/a | n/a | Form I |
| DMA | x | ✓ | | | | | ✓ | Solution after four weeks* | |

✓ = Soluble x = Insoluble, n/a = not applicable. Data can be found in Data Section 2. *No further work was performed on the solution.

Form I was the only form obtained from the screen. Comparison spectra from all of the solvents screened are given in FIGS. 11 and 12, with the exception of DMF and DMA, from which no solid was found to precipitate. Chemical purity profiles of two of the samples isolated from EtOH and EtOAc experiments were recorded to check the material susceptibility to hydrolysis. The results were 97.4% and 96.8% respectively (reference to chemical purity of the starting material, 98.2%) as set forth in FIGS. 29 and 30.

Example 3—Characterization and Approximate Solubility of Sample 4

Prior to any testing. Sample 4 was characterized by XRPD, TGA, DSC, 1HNMR, and DVS. The results are given below in Table-8. The Corresponding figure numbers are given in the right hand column.

TABLE 8

Characterization of Sample 4 Prior to Testing.

| Analysis | Result |
| --- | --- |
| XRPD | crystalline, pattern indexed, Form I |
| TGA | 168° C. (onset, decomp.) |
|  | negligible weight loss prior to decomp. |
| DSC | 166° C. (exo, peak); |
|  | 175° C. (endo, peak) |
| $^1$H NMR | consistent with chemical structure of MRZ |
| DVS | −0.035 wt % (at 5% RH) |
|  | +0.039 wt % (5-75% RH) |
|  | +1.158 wt % (75-95% RH) |
|  | −1.276 wt % (95-5% RH) |

Approximate Solubility

Weighed samples of MRZ, Sample 4 were treated with aliquots of the test solvents or solvent mixtures at ambient temperature. Complete dissolution of the test material was determined by visual inspection. Solubility was estimated based on the total solvent volume used to provide complete dissolution. The actual solubility may be greater than the value calculated because of the use of solvent aliquots that were too large or due to a slow rate of dissolution. If complete dissolution was not achieved during the experiment, the solubility is expressed as "less than". If complete dissolution was achieved by only one aliquot addition, the value is reported as "larger than". The results are given in Table-9, below. As set forth in Table-9, the ratio of solvent mixtures are given by volume. Solubilities are estimated at ambient temperature and reported to the nearest mg/mL; if complete dissolution was not achieved, the value is reported as "<"; the actual solubility may be greater than the reported value due to the use of solvent aliquots that were too large or due to a slow rate of dissolution. Post-solubility samples were stored at 2-8° C. for 15-16 days followed by 1 day at ambient storage before visual inspection for precipitation. Post-solubility samples were visually inspected after 2-3 days of ambient storage. Formation system A is: 55% propylene glycol+5% ethanol+40/citrate buffer (10 mM; pH5). Formation system B is: 14/86 (v/v) H$_2$O/tert-butyl alcohol containing 30 mg/mL sucrose, and titrated with HCl to pH 3.2±0.2.

TABLE 9

Approximate Solubility of Sample 4 Prior to Testing

| Solvent | Solubility (mg/mL) | Precipitates formed during storage? |
| --- | --- | --- |
| Formulation System A | <1 | N/A |
| Formulation System B | 6 | no |
| acetic acid | 10 | no |
| IPA | 6 | no |
| [EMIm][NTF$_2$] | 1 | N/A |
| [EMIm][Cl] | <2 | N/A |
| ACN | 10 | no |
| tert-butanol | 3 | no |
| acetone | 39 | no |
| anisole | 2 | no |
| CHCl$_3$ | 2 | yes |
| cyclohexanone | 22 | no |
| DMSO | >83 | no |
| DCM | 2 | no |
| dioxane | 20 | no |
| EtOAc | 15 | no |
| Formic acid | 15 | no |
| MeOAc | 20 | no |
| MIBK | 11 | no |
| MEK | 33 | yes (small amount) |
| nitromethane | 2 | no |
| NMP | 5 | no |
| pyridine | 36 | no |
| THF | 49 | no |
| 2-Me THF | 32 | no |
| 1-propanol | 2 | no |
| 2,2,2-trifluoroethanol | <1 | N/A |
| 50:50 acetone/heptane | 12 | no |
| 50:50 acetone/iso-octane | 12 | no |
| 25:75 ACN/MTBE | 10 | no |
| 20:80 CHCl$_3$/DCM | 3 | no |
| 25:75 DMF/anisole | 17 | no |
| 50:50 EtOAc/cyclohexane | 4 | no |
| 50:50 EtOAc/isooctane | 2 | no |
| 20:80 MEK/IPA | 10 | no |
| 20:80 MEK/MIBK | 12 | no |
| 50:50 MeOH/Et$_2$O | 21 | no |
| 20:80 NMP/IPA (c) | 19 | no |
| 20:80 NMP/1-propanol | 19 | no |
| 50:50 THF/hexanes | 21 | no |
| 20:80 THF/nitromethane | 15 | no |
| 20:80 2-MeTHF/MeOAc | 34 | no |

Example 4—Polymorph Screen of Marizomib Sample 4 Evaporation Attempts

For slow evaporation (SE), solutions containing marizomib Sample 4 in selected solvents were allowed to evaporate at ambient temperature from vials covered with perforated aluminum foil. For fast evaporation (FE), solutions containing marizomib Sample 4 in selected solvents were allowed to evaporate at ambient temperature from open vials. The results are given below in Table-10. For flash evaporation, solids of disordered marizomib Sample 4 were added dropwise to pre-warmed glass vials, allowing the solvent to flash evaporate immediate upon contact. Resulting solids were collected for analysis. The corresponding figure numbers are given in the right hand column.

TABLE 10

Polymorph Screen of Manzomib Sample 4 Evaporation Attempts

| Solvent | Condition | Observations/Comments | XRPD Results |
| --- | --- | --- | --- |
| acetone | SE | white solids, dendritic particles | Form I |
| CHCl$_3$ | SE | white solids, needles, agg. | Form I |
| IPA | SE | white solids, needles, B/E | Form I |
| THE | FE | white solids, dendritic particles | Form I |
| MEK | FE | white solids, columns, agg. | Form I |
| ACN | FE | white solids, needles, agg. | Form I |
| DCM | FE | white solids, columns, agg. | Form I |

Example 5—Polymorph Screen of Marizomib Sample 4 Cooling Attempts

For crash cooling (CC), concentrated solutions of marizomib Sample 4 were prepared at elevated temperature and filtered through pre-warmed 0.2-μm nylon filters into a clean vial pre-chilled in a dry ice/acetone bath. For fast cooling (FC) and slow cooling (SC), solutions containing marizomib Sample 4 in selected solvents at elevated temperatures in sealed vials. Solutions were then filtered into clean vials with 0.2-μm nylon filters and removed from the heating plate and left at ambient conditions (FC) or allowed to cool to specified temperature on the heating plate (SC). The results are given below in Table-11. Asset forth below, the ratio of solvent mixtures are given by volume. Temperature and time are approximate.

TABLE 11

Polymorph Screen of Marizomib Sample 4 Cooling Attempts

| Solvent | Condition | Observations/Comments | XRPD Results |
|---|---|---|---|
| ACN | 1. CC (65° C. to −78° C.) | 1. white solids, some columns, B/E | Form I |
| EtOAc | 1. CC (70° C. to −78° C.)<br>2. kept at RT for 5 min | 1. clear solution<br>2. white solids, small fibrous particles | Form I |
| THF/hexanes (50:50) | 1. CC (70° C. to −78° C.)<br>2. kept at RT for 10 min | 1. clear solution<br>2. white solids, IS | — |
| MeOAC | 1. CC (65° C. to −78° C.)<br>2. kept at RT for 5 min | 1. clear solution<br>2. white solids, fine particles, UM | Form I |
| MEK/IPA (20:80) | 1. CC (78° C. to −78° C.)<br>2. kept at RT for 5 min | 1. clear solution<br>2. white solids, fine particles, UM, some B | Form I + additional peaks |
| NMP/1-PrOH (20:80) | 1. CC (78° C. to −78° C.)<br>2. kept at RT for 5 rain<br>3. kept at −10 to −25° C. for 7 d | 1. clear solution<br>2. clear solution<br>3. white solids, UM small particles, IS | — |
| MIBK | 1. SC (70° C. to RT) | 1. white solids, columns, agg., B/E | Form I |
| cyclohexanone | 1. SC (70° C. to RT)<br>2. kept at 2-8° C. for 1 d<br>3. kept at −10 to −25° C. for 20 d<br>4. cyclohexane added, kept at 2-8° C. for 2 d | 1. clear solution<br>2. clear solution<br>3. clear solution<br>4. cloudy solution, white solids, fibrous needles | Form I |
| EtOAc/isooctane (50:50) | 1. SC (70° C. to RT)<br>2. kept at 2-8° C. for 1 d<br>3. kept at −10 to −25° C. for 6 d | 1. clear solution<br>2. clear solution<br>3. needles, B/E | Form I |
| THF/nitromethane (20:80) | 1. SC (65° C. to RT) | 1. white solids, columns, B/E | Form I |
| [EMIm][NTF$_2$] | 1. SC from 77° C. to RT<br>2. kept at RT for 11 d | 1. clear solution<br>2. white solids, fine particles, UM, agg., B | Form I |
| [EMIm][Cl] | 1. FC (105° C. to 81° C.) (c)<br>2. hot H$_2$O added | 1. orange solution<br>2. off-white solids, fine particles, UM, B | unique pattern + minor Form I |
| Formulation System A | 1. SC from 77° C. to RT | 1. white solids, fibrous agg. | Form I |
| Formulation System A | 1. CC (105° C. to −78° C.)<br>2. kept at 2-8° C. tor 6 d | 1. sample frozen<br>2. white solids, small particles, agg., UM | Form I |
| Formulation System B | 1. SC (85° C. to RT) | 1. white fibrous solids | Form I |

Example 6—Polymorph Screen of Marizomib Sample 4 Solvent/Antisolvent Addition Attempts For solvent/antisolvent (SAS) experiments, concentrated solutions of marizomib were prepared in selected solvents and solutions were filtered through 0.2-μm nylon filters, either into antisolvent at ambient conditions, or into clean vials and antisolvents were subsequently added into the solutions. In the case of crash precipitation (CP), concentrated solutions of marizomib were prepared in selected solvents and filtered through 0.2-μm nylon filters and into anti-solvent precooled in an ice/water bath. The results are given below in Table-12. The ratio of solvent mixtures are by volume. Time and temperature are approximate.

TABLE 12

Polymorph Screen of Marizomib Sample 4 Solvent/Antisolvent Addition Attempts

| Solvent | Condition | Observations/Comments | XRPD Results |
|---|---|---|---|
| pyridine/Et$_2$O (5:7) | 1. CP (solution in pyridine added to cold Et$_2$O) | 1. no solids | — |
| acetone/isooctane (1:3) | 1. CP (solution in acetone added to cold isooctane) | 1. white solids, some fibrous particles, some B | Form I |
| EtOAc/cyclohexane (1:2) | 1. CP (solution in EtOAc added to cold cyclohexane) | 1. white solids, agg., anh. particles | Form I |
| acetone/heptane (1:1) | 1. CP (solution in acetone added to cold heptane) | 1. white solids, agg., anh. particles | Form I |
| formic acid/CHCl$_3$ (1:1) | 1. cold CHCl$_3$ added into sample solution of 6882-21-08<br>2. kept at 2-8° C. 1 day | 1. rose colored solution, clear<br>2. no solids<br>3. sample frozen | Form I + additional peaks |

TABLE 12-continued

Polymorph Screen of Marizomib Sample 4 Solvent/Antisolvent Addition Attempts

| Solvent | Condition | Observations/ Comments | XRPD Results |
|---|---|---|---|
| | 3. kept at −10 to −25° C. overnight<br>4. kept at 2-8° C.<br>5. evaporation at RT, purged w/N$_2$ after 3 d | 4. rose colored solution<br>5. off white solids, agg., small particles, UM | |
| MEK/IPE (1:5) | 1. CP (solution in MEK added to cold IPE), manually shaken | 1. white solids, small fibrous particles, UM, B | Form I |
| THF/hexanes (1:5) | 1. CP (solution in THF added to cold hexanes), manually shaken | 1. white solids, small particles & agg., UM | Form I |
| ACN/heptane (3:10) | 1. CP (solution in ACN added to cold heptane), shaken<br>2. shaken at 5° C. on orbital shaker for 6 d<br>3. shaken at −4 to 2° C. on orbital shaker for 3 d<br>4. evaporation under N$_2$ | 1. clear solution<br>2. clear solution<br>3. clear solution<br>4. white solids, agg., columns, B/E | Form I |
| acetone/Formulation System A (1/2) | 1. solids dissolved in acetone<br>2. solution filtered into Formulation System A, shaken<br>3. stored at 2-8° C. for 1 d | 1. clear solution<br>2. mostly clear solution, small particulates<br>3. white solids, fine particles, needles, agg. | Form I |
| 2-Me THF/MTBE (1:5) | 1. CP (solution in 2-Me THF added to cold MTBE), shaken<br>2. shaken at 5° C. on orbital shaker for 6 d<br>3. shaken at −4 to 2° C. on orbital shaker for 3 d<br>4. evaporation under N$_2$ | 1. clear solution<br>2. clear solution<br>3. clear solution<br>4. white solids, needles, agg., B/E | Form I |
| MeOH/Et$_2$O (1:5) | 1, CP (solution in MeOH added to cold Et$_2$O), shaken<br>2. shaken at 5° C. on orbital shaker for 6 d<br>3. shaken at −4 to 2° C. on orbital shaker for 3 d<br>4. evaporation under N$_2$ | 1. clear solution<br>2. clear solution<br>3. clear solution<br>4. white solids, fibrous needles | Form I |
| Formulation System B/nitromethane (1:1.5) | 1. CP (solution in Formulation System B added to cold nitromethane), shaken | 1. white solids, UM, IS | — |

Example 7—Polymorph Screen of Marizomib Sample 4 Slurry Attempts

Sufficient amounts of solids of marizomib Sample 4 were added to selected solvents in vials so that excess solids initially persisted. The mixture was then triturated with a stir bar at specified temperatures for an extended period of time. The results are given below in Table-13. The ratio of solvent mixtures are by volume. Time and temperature are approximate.

TABLE 13

Polymorph Screen of Marizomib Sample 4 Slurry Attempts

| Solvent | Condition | Observations/ Comments | XRPD Results |
|---|---|---|---|
| formic acid | RT, 17 d | all solids dissolved, solution rose color | — |
| acetone/heptane (50:50) | RT, 7 d | — | Form I |
| NMP | RT, 7 d | white solids, small particles, UM, B | Form I |
| 1-propanol | 50° C., 7 d | white solids, pasty, B, UM | Form I |
| anisole | 50° C., 7 d | white solids, UM | Form I |
| nitromethane | 50° C., 7 d | white solids, small particles, UM | Form I |
| 2-Me THF/MeOAc (20:80) | RT, 7 d | white solids, some columns, B | Form I |
| CHCl$_3$ | RT, 8 d | white solids, fine particles, agg., UM, B | Form I |
| Formulation System A | RT, 13 d | white solids, agg., UM | Form I |
| Formulation System B | RT, 7 d | white solids, fine particles, UM | Form I |

TABLE 13-continued

Polymorph Screen of Marizomib Sample 4 Slurry Attempts

| Solvent | Condition | Observations/Comments | XRPD Results |
|---|---|---|---|
| acetic acid | RT, 7 d | white solids, agglomerates, B | Form I |
| acetone/$H_2O$ (40:60) ($A_w$ = 0.92) | RT, 7 d | white solids, small particles, UM, B | Form I |
| ACN/$H_2O$ (50:50) ($A_w$ = 0.90) | RT, 7 d | white solids, small particles, UM, B | Form I |
| IPA/$H_2O$ (50:50) ($A_w$ = 0.96) | RT, 7 d | white solids, small particles, UM, B | Form I |
| 2-BuOH/$H_2O$ (70:30) ($A_w$ = 1.04) | RT, 7 d | white solids, small particles, UM, B | Form I |
| HFIPA/$H_2O$ (75:25) ($A_w$ = 1.41) | RT, 7 d | white solids, small particles, UM, B | Form I |
| TFE/$H_2O$ (50:50) ($A_w$ = 1.08) | RT, 7 d | white solids, small particles, UM, B | Form I |

Example 8—Polymorph Screen of Marizomib Sample 4 Manual Grinding Attempts

Solids of marizomib Sample 4 were ground by hand at room temperature using a mortar and pestle at five minutes per cycle for two (wet grinding) or four (dry grinding) cycles. In the case of wet grinding, a small amount of select solvent or solvent mixture (10 μL) was added before grinding. The inside of the mortar was scraped between each cycle. The results are given below in Table-14. As set forth below, the ratio of solvent mixtures are given by volume. Times are approximate. Disordered Form I was used as the starting material for the water recrystallization experiment.

TABLE 14

Polymorph Screen of Marizomib Sample 4 Manual Grinding Attempts

| Solvent | Condition | Observations/Comments | XRPD Results |
|---|---|---|---|
| — | 4 × 5 min | white solids, UM, agg. | disordered Form I |
| Formulation System A | 2 × 5 min; 2 × 10 μL | white tacky solids agglomerates, B | Form I |
| Formulation System B | 2 × 5 min; 2 × 10 μL | white solids, fine particles, agg., UM, B | disordered Form 1 |
| acetone/heptane (50/50) | 2 × 5 min; 2 × 10 μL | white solids, fine particles, agg., UM, B | disordered Form I |
| formic acid | 2 × 5 min; 2 × 10 μL | white solids, fine particles, agg., UM, B | disordered Form I |
| acetic acid | 2 × 5 min; 2 × 10 μL | white solids, fine particles, agg., UM, B | disordered Form I |
| water | 2 × 5 min; 2 × 10 μL | white solids, small particles, agg., UM, B | disordered Form I |

Example 9—Polymorph Screen of Marizomib Sample 4 Heat Stress Attempts from Disordered Form I Solids of disordered marizomib Sample 4 were held at designated temperatures for the indicated amount of time. The results are given below in Table-15. Resulting solids were collected for analysis. Temperature and time are approximate.

TABLE 15

Polymorph Screen of Marizomib Sample 4 Heat Stress Attempts from Disordered Form I

| Condition | Observations/Commems | XRPD Results |
|---|---|---|
| 44° C., overnight | white solids, fluffy, agg., UM | Form I w/some disorder |
| 60° C., 5 h | white solids, fluffy, agg., UM | Form I w/some disorder |
| 80° C., 2 h | white solids, fluffy, agg., UM | Form I w/some disorder |

Example 10—Experimental Attempts Targeting Amorphous Marizomib

For lyophilization, a solution of MRZ was prepared in either dioxane or Formulation System B, filtered through 0.2-μm nylon filter, and frozen in a glass flask by rotating it in a cold dry ice/IPA bath. The flask was then purged with $N_2$, submerged in a propylene glycol bath at temperatures below −25° C., and placed under vacuum of 0.028 mm Hg to dry for 2 to 5 days. The resulting solids were collected for analysis.

For fast evaporation (FE), solutions containing MRZ in selected solvents were allowed to evaporate at ambient temperature from open vials. The results are shown in Table-16 below. The ratio of solvent mixtures are by volume. Time and temperature are approximate. The acetone used was anhydrous.

TABLE 16

Experimental Attempts Targeting Amorphous Marizomib

| Solvent | Condition | Observations/ Comments | XRPD Results |
|---|---|---|---|
| acetone | flash evaporation at 110° C. | white solids, some yellowing, agg., UM | Form I + additional peaks |
| acetone | flash evaporation at 90° C. | white solids, needles, agg., B/E | Form I |
| dioxane | lyophilization | static white powder, UM | Form I |
| dioxane | lyophilization | white powder, static, clumps | disordered Form I |
| dioxane | lyophilization | white powder, flakey, fluffy | disordered Form I |
| Formulation System B | lyophilization | clear, gooey, sticky | disordered Form I |

Example 11—Further Analysis on Selected Samples from Polymorph Screen

TABLE 17

Analysis of on Selected Samples from Polymorph Screen

| Condition | Analysis | Result |
|---|---|---|
| flash evaporation from acetone (110° C.) | $^1$H NMR | peaks attributable to MRZ observed + unidentified additional peaks with substantial integral intensities |
| crash cool from MEK/IPA (78 to −78° C.) | $^1$H NMR | spectrum in general consistent with chemical structure of MRZ + small additional unidentified peaks |
| lyophilization | mDSC | 161° C. (endo, onset) |
| FC from [EMIm][Cl] followed by addition of hot H$_2$O | $^1$H NMR | spectrum not consistent with chemical structure of MRZ |

TABLE 17-continued

Analysis of on Selected Samples from Polymorph Screen

| Condition | Analysis | Result |
|---|---|---|
| evaporation from formic acid/CHCl$_3$ | $^1$H NMR | peaks attributable to MRZ observed + unidentified additional peaks, some peaks with substantial integral intensities |

Example 12—Co-Crystal Screen of Marizomib

For crash cooling (CC), a solution of MRZ and coformer was prepared at elevated temperature in a given solvent mixture. The vial was capped and immediately placed in a refrigerator or freezer. For fast cooling (FC), solutions of MRZ and coformer were prepared at elevated temperatures in given solvents or solvent mixtures. The vial was capped and placed on a bench top at room temperature to quickly cool. For slow cooling (SC), a solution of MRZ and coformer was prepared at elevated temperature in a given solvent mixture. The vial was capped and left in a heating block at elevated temperature. The heater then was turned off for the sample to cool down naturally to room temperature. For slow evaporation (SE), solutions of MRZ and coformer were generated at ambient temperature in a given solvent or solvent mixture. The solutions were allowed to evaporate partially or to dryness from a loosely capped vial at ambient conditions. Slurry experiments were carried out by making saturated solutions containing excess solid. The slurries were agitated at ambient or elevated temperatures for a specified amount of time. The solids present were recovered via positive pressure filtration. Solvent assisted grinding experiments were carried out by mixing MRZ and coformer in an agate mortar and pestle. Aliquots of solvent were added and the mixture ground manually for specified amount of time. The solids were scraped from the walls of the mortar and the pestle head. Another aliquot of solvent added and ground for several more minutes. For temperature cycling, solutions or suspensions of MRZ and coformer were made in a given solvent and placed at elevated temperature. The sample was cycled by removing from heat and then reapplying several times. The solids were collected via vacuum filtration upon the last cool from elevated temperature.

As set forth in Table 18 below, "X:Y" refers to marizomib:conformer mole ratio. Temperatures and times are approximate. Solvent ratios are by volume. Approximately 60-90 mg of marizomib was used for each experiment.

TABLE 18

Cocrystal Screen of Marizomib

| Coformer (X:Y) | Conditions | Observations | XRPD Results |
|---|---|---|---|
| Acetic acid (large excess) | Slurry, RT | White solids PLM:agglomerates, B | MRZ |
| Acetic acid (1:2) | 1) Acetone, stir, RT, 5 days 2) Cool, 2-8° C., 3 days 3) SE, RT | 1) Slightly turbid solution 2) Faint hazy solution 3) Translucent solids PLM:agglomerates, prismatics, B | MRZ |
| Adenine (1:1) | EtOH, slurry, RT, 5 days | White solids PLM:Small particles, unknown morphology, B | MRZ |

TABLE 18-continued

Cocrystal Screen of Marizomib

| Coformer (X:Y) | Conditions | Observations | XRPD Results |
|---|---|---|---|
| Adenine (1:3) | 1) Add MeOH io adenine 2) Add MIBK to MRZ 3) Add adenine suspension to MRZ 4) Slurry at 60° C. O/N 5) Slurry, RT, 1 day | 1) White suspension 2) White suspension 3) White suspension 4) White suspension 5) White solids PLM:small particles, unknown morphology | MRZ + minor adenine |
| L-alanine (1:1) | 1) Dissolve L-alanine in H₂O 2) Dissolve MRZ in pyridine 3) Add L-alanine to MRZ 4) Slurry, RT, 2 days 5) Cool to 2-8° C. 6) SE, RT | 1) Clear, colorless solution 2) Clear, colorless solution 3) White gel 4) White suspension insufficient for XRPD 5) White suspension, insufficient for XRPD 6) Clear, tacky gel | — |
| L-alanine (1:1) | 1) Add MeOH to L-alanine 2) Add suspension to MRZ 3) Slurry at 60° C. O/N 4) Slurry, RT, 1 day | 1) Solids remain 2) White suspension 3) White suspension 4) White solids PLM:small particles, unknown morphology | MRZ |
| L-arginine (1:1) | 1) Dissolved L-arginine in HFIPA 2) Dissolved MRZ in dioxane 3) Added L-arginine solution dropwise to MRZ solution 4) Stir, RT, ~25 minutes SE (FIG. 129 filtrate material), RT | 1) Clear, colorless solution 2) Clear, colorless solution 3) Turbid solution 4) White solids PLM:small particles, unknown morphology, B. Yellow gel | MRZ — |
| L-ascorbic acid (2:1) | MIBK, FC, 75° C. to RT | White solids | MRZ + L-ascorbic acid |
| L-ascorbic acid (1:1) | 1) IPA added to MRZ at 50° C. 2) L-ascorbic acid dissolved in MeOH 3) L-ascorbic acid added dropwise to MRZ at 50° C. 4) FC to RT | 1) Scant solids remain 2) Clear, colorless solution 3) Clear, colorless solution 4) White solids PLM:small particles, unknown morphology, B. | MRZ |
| L-ascorbic acid (1:5) | ACN, slurry, RT, 7 days | White solids PLM:small particles, unknown morphology, B | MRZ + L-ascorbic acid |
| Benzoic acid (2:1) | EtOAc, SE, RT | Translucent solids PLM:needles, agglomerates, B/E possible singles | MRZ |
| Benzoic acid (1:1) | 1) Dissolve benzoic acid in EtOH 2) Dissolve MRZ in acetone 3) Add benzoic acid to MRZ 4) Stir, RT, 2 days 5) SE at RT | 1) Clear, colorless solution 2) Clear, colorless solution 3) Clear, colorless solution 4) Clear, colorless solution 5) Translucent solids PLM:agglomerates of needles, B | MRZ + benzoic acid |
| Benzoic acid (1:5) | MEK:MIBK (20:80), slurry, RT, 7 days | White solids PLM:small particles, unknown morphology, B | MRZ |
| Caffeine (1:1) | Dioxane, SC, 50° C. to RT | White solids | MRZ + caffeine |
| Caffeine (1:2) | 1) Add THE to caffeine 2) Add caffeine suspension to MRZ 3) Slurry, 50° C., 2 days | 1) White suspension 2) White suspension 3) White solids PLM:small particles, agglomerates, unknown morphology, B. | Caffeine + minor MRZ |
| Caffeine (1:3) | DMF:anisole (25:75), slurry, RT, 6 days | White solids, PLM:small particles, unknown morphology, B | Caffeine |

TABLE 18-continued

Cocrystal Screen of Marizomib

| Coformer (X:Y) | Conditions | Observations | XRPD Results |
|---|---|---|---|
| Trans-cinnamic acid (1:1) | 1) Dissolve trans-cinnamic acid in ACN<br>2) Dissolve MRZ in MEK<br>3) Add trans-cinnamic acid solution to MRZ dropwise<br>4) Stir, RT, 3 days<br>5) Cool to 2-8° C.<br>6) SE, RT | 1) Clear, colorless solution<br>2) Clear, colorless solution<br>3) Clear, colorless solution<br>4) Clear, colorless solution<br>5) Scant translucent solids PLM:Rods, B/E<br>6) White solids PLM:prisms and plates, B | MRZ + trans-cinnamic acid |
| Citric acid (1:1) | NMP, crash cool, 50° C. to 2-8° C. | Clear, colorless solution | — |
| Citric acid (1:2) | Solvent assisted grinding, IPA, (3 × 5 minutes, 3 × 10 µL) | White solids | MRZ + citric acid |
|  | 1) EtOAc, slurry, 50° C., 5 days<br>2) Slurry, RT, 6 days | 1) Scant white solids<br>2) White solids PLM:small particles, unknown morphology, B | MRZ + citric acid |
| Citric acid (1:3) | MTBK, slurry, RT, 6 days | White solids, PLM:small particles, unknown morphology, B | MRZ + citric acid |
| (2-hydroxypropyl)-β-cyclodextrin (1:1) | 1) Dissolve (2-hydroxypropyl)-β-cyclodextrin in MeOH<br>2) Dissolve MRZ in acetone<br>3) Add coformer solution to MRZ<br>4) Shirty at RT<br>5) After ~20 minutes, place at 50° C.<br>5) Slurry, 50° C., 2 days<br>6) Supernatant solution decanted, SE, RT | 1) Clear, colorless solution<br>2) Clear, colorless solution<br>3) White precipitation<br>4) White suspension (gel)<br>5) Clear solution with white gel at bottom<br>5) Clear solution with clear gel at bottom<br>6) White solids PLM:needles, spherulites, B | MRZ |
| (2-hydroxypropyl)-β-cyclodextrin (2:1) | 1) Dissolve (2-hydroxypropyl)-β-cyclodextrin in H₂O<br>2) Dissolve MRZ in ACTS at 50° C.<br>3) Add H₂O solution to ACN solution at 50° C.<br>4) Slurry, 50° C., 2 days<br>5) Slurry, RT, 6 days<br>6) SE, RT | 1) Clear, colorless solution<br>2) Clear, colorless solution<br>3) White suspension<br>4) Turbid suspension<br>5) Turbid solution<br>6) Translucent solids PLM:needles, BE | MRZ |
| L-cysteine (1:1) | 1) Grind L-cysteine and MRZ ~10 minutes<br>2) Add EtOH/dioxane (50/50)<br>3) Sonicated ~2 minutes<br>4) Temperature cycle between RT and 50° C. (4 cycles × 1 hour each temperature, held at RT overnight) | 1) White solids<br>2) White suspension<br>3) White suspension<br>4) White solids PLM:small particles, unknown morphology, B | MRZ |
| L-cysteine (1:2) | 1) Add H₂O to L-cysteine at 50° C.<br>2) Dissolve MRZ in ACN at 60° C.<br>3) L-cysteine solution added to ACN solution<br>4) Slurry, 50° C., 2 days<br>5) Slurry, RT, 4 days<br>6) SE, RT | 1) Slightly turbid solution<br>2) Clear, colorless solution<br>3) Immediate white precipitation<br>4) Turbid, faintly yellow suspension<br>5) Turbid solution<br>6) Off-white solids PLM:Glassy, no apparent B | Highly disordered crystalline |
| Cytosine (1:1) | 1) Add 0.5 mL H₂O to cytosine, slurry at 50° C.<br>2) Add 0.5 mL ACN to MRZ, slurry at 50° C.<br>3) Sonicate 2 minutes<br>4) Add cytosine suspension to MRZ, slurry at 50° C., 2 days<br>5) Slurry, RT, 6 days | 1) White suspension<br>2) White suspension<br>3) White suspension<br>4) Faintly yellow solution with white solids<br>5) White solids PLM:small particles, unknown morphology, B | MRZ + unique peaks + possible minor cytosine |

TABLE 18-continued

Cocrystal Screen of Marizomib

| Coformer (X:Y) | Conditions | Observations | XRPD Results |
|---|---|---|---|
| Cytosine (1:3) | 1) 1.5 mL H$_2$O added to cytosine<br>2) 1 mL dioxane added MRZ<br>3) Cytosine suspension added to MRZ (dioxane:water 2:3)<br>4) Slurry at 60° C. O/N<br>5) Stir, RT, 1 day | 1) White suspension<br>2) Scant solids remain<br>3) White suspension<br>4) Light yellow, clear solution<br>5) Cream colored solids<br>PLM:small particles, unknown morphology | Unique peaks + MRZ (same as observed in FIG. 233) (XRPD) Primarily cytosine with dioxane and trace MRZ additional peaks also present (NMR) |
| Fumaric acid (1:1) | Anh. acetone, SE, RT | Translucent solids<br>PLM:needles, dendritics, B/E | MRZ + fumaric acid + additional peak |
| Fumaric acid (1:1) | Solvent assisted grinding, ACN (2 × 5 minutes, 2 × 20 μL) | White solids | MRZ + fumaric acid |
| Fumaric acid (1:3) | 1) Added TFE to fumaric acid at 50° C.<br>2) Dissolved MRZ in THF at 50° C.<br>3) Added fumaric acid to MRZ solution<br>4) Temp. cycle (50° C. - RT) three cycles hold 4 hours | 1) White suspension<br>2) Clear, colorless solution<br>3) White suspension<br>4) White solids<br>PLM: small particles, unknown morphology, B | MRZ + fumaric acid |
| Gentisic acid (1:1) | 1) Dissolve gentisic acid in t-BuOH at 50° C.<br>2) Add to MRZ at 50° C.<br>3) Slurry, 50° C., 2 days | 1) Clear, colorless solution<br>2) White suspension<br>3) White solids<br>PLM:fibrous and small particles with unknown morphology, B | MRZ |
| Gentisic acid (2:1) | ACN, FC, 60° C. to RT | White solids<br>PLM:agglomerates, fines, B. | MRZ |
| Gentisic acid (1:5) | MEK:IPA (20:80), shirty, RT, 6 days | White solids,<br>PLM:small particles, unknown morphology, B | MRZ |
| L-glutamine (1:1) | Anh. acetone, grinding (2 × 5 minutes, 2 × 20 μL) | White solids | MRZ + L-glutamine |
| L-glutamine (1:3) | 1) Dissolve L-glutamine in H$_2$O at 50° C.<br>2) Dissolve MRZ in 2-MeTHF at 50° C.<br>3) Add L-glutamine to MRZ dropwise at 50° C.<br>4) FC/FE at RT | 1) Clear, colorless solution<br>2) Clear, colorless solution<br>3) Two clear, colorless layers<br>4) White solids<br>PLM:fibrous, B | MRZ + minor L-glutamine |
| L-glutamine (1:5) | ACN:MTBE (25:75), slurry, RT, 6 days | White solids,<br>PLM:small particles, unknown morphology, B | MRZ + L-glutamine |
| Glutaric acid (1:1) | 1) Dissolve glutaric acid in IPrOAc<br>2) Dissolve MRZ in ACN at 50° C.<br>3) Add glutaric acid solution dropwise<br>4) Stir, 50° C., 2 days<br>5) FC to RT<br>6) Cool to 2-8° C.<br>7) SE, RT | 1) Clear, colorless solution<br>2) Clear, colorless solution<br>3) Clear, colorless solution<br>4) Clear, colorless solution<br>5) Clear, colorless solution<br>6) Clear, colorless solution<br>7) Translucent solids<br>PLM:dendrites, needles, B | MRZ + Glutaric acid |
| Glutaric acid (1:3) | 1) Dissolve glutaric acid in EtOH<br>2) Add to MRZ<br>3) Slurry, RT, 6 days | 1) Clear, colorless solution<br>2) White suspension<br>3) White suspension<br>PLM:small particles, unknown morphology, B | MRZ |

TABLE 18-continued

Cocrystal Screen of Marizomib

| Coformer (X:Y) | Conditions | Observations | XRPD Results |
|---|---|---|---|
| Glycine (2:1) | ACN, grinding (2 × 5 minutes, 2 × 20 µL) | White solids | MRZ + glycine |
| Glycine (1:1) | 1) Dissolve glycine in H₂O<br>2) Dissolve MRZ in acetone<br>3) Add glycine to MRZ dropwise<br>4) Slurry, RT, 2 days | 1) Clear, colorless solution<br>2) Clear, colorless solution<br>3) White precipitate<br>4) White solids<br>PLM:small particles, unknown morphology, B | MRZ + glycine |
| Glycine (1:5) | EtOAc:cyclohexane (50:50), slurry, RT, 5 days | White solids,<br>PLM:small particles, unknown morphology, B | MRZ + glycine |
| Glycolic acid (1:1) | 1) Melt glycolic acid at 85° C.<br>2) Add MRZ<br>3) Dissolve in THF at 85° C.<br>4) Evaporate off solvent at 85° C. | 1) Clear melt<br>2) White solids<br>3) Clear, colorless solution<br>4) White solids<br>PLM:small needles, B. | MRZ + minor glycolic acid |
| Glycolic acid (1:2) | Acetone, SE, RT | White solids<br>PLM:Needles, B. | MRZ |
| Hippuric acid (1:1) | 1) MEK, FC, 65° C. to RT<br>2) Cool to 2-8° C. | 1) Scant solids<br>2) White solids<br>PLM:equants, B. | Hippuric acid + MRZ peak |
| Hippuric acid (1:5) | 1) Add IPA/HFIPA (1:1) to Hippuric acid<br>2) Add suspension to MRZ<br>3) Heat to 50° C.<br>4) Slurry, 50° C., 6 days | 1) White suspension<br>2) White suspension<br>3) White suspension<br>4) White solids<br>PLM:small particles, unknown morphology, B | MRZ + hippuric acid |
| Hydantoin (1:1) | 1) Add dioxane<br>2) Add H₂O (2:1 dioxane:H₂O)<br>3) Slurry, RT | 1) Scant solids remain<br>2) White precipitation<br>3) White solids<br>PLM:small particles, unknown morphology, B. | MRZ |
| Hydantoin (1:3) | 1) H₂O added to hydantoin<br>2) ACN added to MRZ<br>3) Hydantoin suspension added to MRZ<br>4) Slurry, 60° C. overnight<br>5) Stir, RT, 1 day | 1) White suspension<br>2) Clear, colorless solution<br>3) White suspension<br>4) Clear, colorless solution<br>5) White solids<br>PLM:tangled fibers, B. | MRZ |
| 4-hydroxybenzoic acid (1:1) | 1) Dissolve 4-hydroxybenzoic acid in anh. acetone<br>2) Add anh. acetone to MRZ<br>3) Add 4-hydroxybenzoic acid solution to MRZ<br>4) Stir, RT<br>5) SE, RT | 1) Clear, colorless solution<br>2) White suspension<br>3) White suspension<br>4) White suspension, insufficient for analysis<br>5) White solids<br>PLM:needles and dendrites, B | MRZ + 4-hydroxy benzoic acid |
| 4-hydroxybenzoic acid (1:1) | 1) 4-hydroxybenzoic acid dissolved in EtOH<br>2) MRZ disslolved in dioxane<br>3) EtOH solution added to MRZ<br>4) Stir, RT, 1 day<br>5) FE, RT | 1) Clear, colorless solution<br>2) Clear, colorless solution<br>3) Clear, colorless solution<br>4) Clear, colorless solution<br>5) White solids<br>PLM:dendrites, needles, B/E. | MRZ + 4-hydroxy benzoic acid |
| Imidazole (1:1) | Pyridine, SC, 45° C. to RT | Clear, golden yellow solution | — |
| Imidazole (1:2) | 1) Dissolve imidazole in acetone<br>2) Add to MRZ<br>3) SE, RT | 1) Clear, colorless solution<br>2) Clear, colorless solution<br>3) Yellow tacky gel | — |
| Imidazole (1:5) | 1) MeOAc, slurry, RT, 2 days<br>2) SE, RT | 1) Clear, light yellow solution<br>2) Golden oil | — |

TABLE 18-continued

Cocrystal Screen of Marizomib

| Coformer (X:Y) | Conditions | Observations | XRPD Results |
|---|---|---|---|
| L-lysine (1:1) | 1) Dissolve L-lysine in HFIPA<br>2) Dissolve MRZ in THF<br>3) Add L-lysine solution dropwise to MRZ<br>4) Stir, RT, ~35 minutes SE (FIG. 171 material filtrate), RT | 1) Yellow solution<br>2) Clear, colorless solution<br>3) Beige suspension<br>4) White solids<br>PLM:small particles, unknown morphology, B.<br>Orange gel | MRZ<br><br>—  |
| L-lysine (1:3) | 1) L-lysine dissolved in $H_2O$<br>2) ACN added to MRZ<br>3) L-lysine solution added to MRZ<br>4) Slurry, 60° C. O/N<br>5) Stir, RT, 1 day | 1) Clear, colorless solution<br>2) Scant solids remain<br>3) White suspension<br>4) Orange solution<br>5) Orange solution | — |
| Maleic acid (1:1) | Nitromethane, SC, 50° C. to RT | White solids | MRZ |
| Maleic acid (1:3) | 1) Added 1-PrOH to maleic acid<br>2) Added to MRZ<br>3) Slurry. RT. 6 days | 1) Clear, colorless solution<br>2) White suspension<br>3) White solids<br>PLM:small particles, unknown morphology, B | MRZ |
| Maleic acid (1:5) | Acetone:heptane (50:50), slurry, RT, 7 days | White solids<br>PLM:small agglomerates, unknown morphology, B. | MRZ + maleic acid |
| DL-malic acid (1:1) | 1) Add DCM to DL-malic acid<br>2) Dissolve MRZ in THF<br>3) Add MRZ solution to DL-malic acid suspension<br>4) Slurry at RT, 7 days | 1) White suspension<br>2) Clear, colorless solution<br>3) White suspension<br>4) White solids<br>PLM:small particles, unknown morphology, B. | MRZ + DL-malic acid |
| DL-malic acid (1:3) | 1) Dioxane added to DL-malic acid<br>2) Transferred to MRZ<br>3) Slurry, 60° C., O/N<br>4) Stir, RT, 1 day<br>5) FE, RT | 1) Solids remain<br>2) White suspension<br>3) Clear, colorless solution<br>4) Clear, colorless solution<br>5) White wet solids<br>PLM:small needles, B. | MRZ |
| Melamine (1:1) | 1) Add 1 mL DMSO:$H_2O$ (1:1) to MRZ. Add melamine.<br>2) Sonicate ~2 minutes<br>3) Slurry at 50° C., 2 days<br>4) Slurry, RT, 6 days | 1) White suspension<br>2) White suspension<br>3) White suspension<br>4) White solids<br>PLM:white solids, unknown morphology, B. | MRZ + unique peaks (XRPD) MRZ:Melamine 1:1.6, DMSO and $H_2O$ present, numerous additional peaks suggestive of some level of degradation (NMR) Broad endotherm at 97.5° C. (peak max), sharp endotherms at 107.9° C. and 124.1° C. (peak max) (DSC) 10.3% weight loss from 30.2° C. to 104.0° C. 21.1% weight loss from 30.2° C. to 146.0° C. (TGA) |

TABLE 18-continued

Cocrystal Screen of Marizomib

| Coformer (X:Y) | Conditions | Observations | XRPD Results |
|---|---|---|---|
| Melamine (1:3) | 1) Add 1 mL DMSO:H$_2$O (1:1) melamine<br>2) Added melamine suspension to MRZ<br>3) Slurry at 60° C. O/N<br>4) Slurry, RT, 1 day | 1) White suspension<br>2) White suspension<br>3) White suspension<br>4) White solids<br>PLM:small particles, unknown morphology | MRZ + melamine + unique peaks |
| Nicotinamide (1:1) | ACN, FC, 70° C. to RT | White damp solids | MRZ |
| Nicotinamide (1:3) | 1) Add acetone to nicotinamide<br>2) Add nicotinamide suspension to MRZ<br>3) Slurry, RT, 6 days | 1) White suspension<br>2) White suspension<br>3) White solids<br>PLM:agglomerates, B | Nicotinamide + MRZ |
| Nicotinamide (1:5) | MEK:IPA (20:80), slurry, RT, 7 days | White solids<br>PLM:small particles, unknown morphology, B | MRZ + nicotinamide |
| Orotic acid (2:1) | 1) Nitromethane added to orotic acid and 50° C.<br>2) Add to MRZ at 50° C.<br>3) Slurry, 50° C., 6 days | 1) White suspension<br>2) White suspension<br>3) White solids<br>PLM:small particles, unknown morphology, B | MRZ |
| Orotic acid (1:1) | MEK, grinding (2 × 5 minutes manual grinding) | White solids | MRZ + minor orotic acid |
| Orotic acid (1:5) | MeOAc, slurry, RT, 7 days | White solids<br>PLM:small particles, unknown morphology, B. | MRZ + orotic acid |
| Oxalic acid (1:1) | Anh. acetone, FE, RT | Translucent solids<br>PLM:dendritics, needles, B. | MRZ + oxalic acid |
| Oxalic acid (1:2) | 1) Oxalic acid dissolved in EtOH<br>2) MRZ dissolved in MEK<br>3) Add oxalic acid solution to MRZ<br>4) Stir, RT, 7 days | 1) Clear, colorless solution<br>2) Clear, colorless solution<br>3) Clear, colorless solution<br>4) White solids<br>PLM:small particles, unknown morphology, B | MRZ |
| Oxalic acid (1:5) | 1) Dissolved MRZ in anhydrous acetone<br>2) Dissolved oxalic acid in EtOH<br>3) Added oxalic acid solution dropwise to MRZ solution<br>4) Stir, RT, 5 days<br>5) SE at RT | 1) Clear, colorless solution<br>2) Clear, colorless solution<br>3) Clear, colorless solution<br>4) Slightly turbid solution<br>5) Translucent off-white solids<br>PLM:needles, prismatics, B/E | MRZ + oxalic acid |
| L-proline (2:1) | Nitromethane, temperature cycle between 50° C. and RT (3 cycles, 1 hour each) | White solids | MRZ + L-proline |
| L-proline (1:1) | 1) Dissolved MRZ in THF<br>2) Dissolved L-proline in MeOH<br>3) Added L-proline solution dropwise to MRZ<br>4) Stir, RT, 4 days<br>SE of FIG. 190 material filtrate, RT | 1) Clear, colorless solution<br>2) Clear, colorless solution<br>3) Clear colorless solution<br>4) White solids<br>PLM:small particles, unknown morphology, B.<br><br>White solids<br>PLM:fibrous agglomerates, B. | L-proline + minor additional peaks (possibly MRZ)<br><br>MRZ + additional peaks |
| L-proline (1:2) | 1) Added EtOH to L-proline at 50° C.<br>2) Added EtOAc to MRZ at 50° C.<br>3) Added EtOH suspension to MRZ<br>4) Temp cycle (50° C. to RT, five cycles, 1 hour each) | 1) White suspension<br>2) White suspension<br>3) White suspension<br>4) White solids<br>PLM:small particles, unknown morphology. B | L-proline + MRZ |

TABLE 18-continued

Cocrystal Screen of Marizomib

| Coformer (X:Y) | Conditions | Observations | XRPD Results |
|---|---|---|---|
| L-proline (1:3) | Acetone:iso-octane (50:50), slurry, RT, 6 days | White solids, PLM:small particles, unknown morphology, B | MRZ + L-proline + additional peaks (possibly L-proline mono-hydrate) |
| L-proline (sat'd in IPA at 50° C.) | Add sat'd L-proline in IPA to MRZ at 50° C. temp cycle (50° C. - RT) | White solids PLM:needles, B/E | MRZ |
| L-proline sat'd in H₂O/MeOH 50/50 v/v | 1) Add L-proline to H₂O/MeOH at 50° C. overnight 2) Hot filter saturated L-proline solution 3) Add saturated solution to MRZ at 50° C. 4) Slurry, 50° C., 2 days 5) Slurry, RT, 3 days | 1) White suspension 2) Clear, colorless solution 3) White suspension 4) Yellow solution, scant solids 5) Viscous yellow suspension PLM:unknown morphology, B. | L-proline |
| L-pyroglutamic acid (1:1) | 1) Dissolve pyroglutamic acid in EtOH 2) Dissolve MRZ in acetone 3) Add pyroglutamic acid to MRZ 4) Stir, RT, 3 days 5) SE, RT | 1) Clear, colorless solution 2) Clear, colorless solution 3) Clear, colorless solution 4) Clear, colorless solution 5) Translucent solids PLM:dendrites, B/E | MRZ + minor pyro-glutamic acid |
| L-pyroglutamic acid (1:1) | 1) L-pyroglutamic acid dissolved in MeOH 2) EtOAc added to MRZ 3) MeOH solution added to MRZ 4) Stir, RT, 1 day 5) FE, RT | 1) Clear, colorless solution 2) Turbid solution 3) Clear, colorless solution 4) Clear, colorless solution 5) White solids, PLM:dendrites and needles, B | MRZ + L-pyro-glutamic acid |
| L-pyroglutamic acid (1:2) | Slurry, ACN, RT, 6 days | White solids PLM:small particles, unknown morphology, B | MRZ + L-pyro-glutamic acid |
| 2-pyrrolidone (1:1) | 1) Dissolve MRZ in acetone (1 mL) at 50° C. 2) Add 25 µL 2-pyrrolidone at RT to MRZ solution 3) Temperature cycle between 50° C. and RT (4 cycles × 1 hour at each temperature, held at RT overnight) 4) SE, RT | 1) Clear, colorless solution 2) Clear, colorless, solution 3) Hazy solution, insufficient for XRPD 4) White solids PLM:small needles, B. | MRZ + extra peaks at 14.1 and 15.5°2θ (XRPD) MRZ:2-pyrrolidone 1:1.2 + additional minor peaks, no acetone detected (NMR) Sharp endotherm with an onset at 29.4° C. and peak max at 32.8° C. Broad features (endo-thermic) at 91.4° C. and 131.3° C. (peak max.) (DSC) 5.0% weight loss from 27.1° C. to 92.0° C. (TGA) |

TABLE 18-continued

Cocrystal Screen of Marizomib

| Coformer (X:Y) | Conditions | Observations | XRPD Results |
|---|---|---|---|
| 2-pyrrolidone (excess) | Manual grinding (2 × 5 minutes, 2 × 10 µL) | White tacky solids | MRZ + extra peaks at 14.1 and 15.5 °2θ |
| 2-pyrrolidone (large excess) | 1) Dissolve MRZ in 500 µL 2-pyrrolidone at 50° C.<br>2) Cool to RT with stirring<br>3) FE, RT | 1) Clear, slightly yellow sol'n<br>2) Clear, colorless solution<br>3) Clear solution | — |
| Saccharin (1:1) | IPA, FC, 70° C. to RT | White damp solids | MRZ |
| Saccharin (1:2) | 1) Dissolve saccharin in acetone<br>2) Add to MRZ<br>3) Slurry, RT, 6 days | 1) Clear, colorless solution<br>2) White suspension<br>3) White solids<br>PLM:small particles, unknown morphology, B | MRZ + minor saccharin |
| Saccharin (1:5) | ACN, slurry, RT, 7 days | White solids<br>PLM:small agglomerates, unknown morphology, B | MRZ + Saccharin |
| Salicylic acid (1:1) | EtOAc:toluene (50:50), FC, 75° C. to RT | White solids<br>PLM:agglomerates, needles, B/E. possible singles | MRZ |
| Salicylic acid (1:3) | 1) Salicylic acid dissolved in EtOH<br>2) MRZ dissolved in MIBK<br>3) Salicylic acid solution added to MRZ<br>4) Stir, RT | 1) Clear, colorless solution<br>2) Clear, colorless solution<br>3) Clear, colorless solution<br>4) White solids,<br>PLM:Small particles, unknown morphology, B | MRZ |
| | 1) Salicylic acid dissolved in EtOH<br>2) MRZ dissolved in MEK<br>3) Salicylic acid solution added to MRZ<br>4) Stir, RT, 8 days<br>5) SE, RT | 1) Clear, colorless solution<br>2) Clear, colorless solution<br>3) Clear, colorless solution<br>4) Clear, colorless solution<br>5) White solids<br>PLM:dendritics and needles, B | MRZ + salicylic acid |
| Salicylic acid (1:5) | 1) Salicylic acid dissolved in 1-PrOH, MRZ dissolved in ACN, addition of MRZ solution to salicylic acid solution<br>2) Stir, RT, 2 days<br>3) Cool to 2-8° C., 4 days<br>4) FE, RT | 1) Clear, colorless solution<br>2) Clear, colorless solution<br>3) Clear, colorless solution<br>4) White solids<br>PLM:needles, dendrites, B | MRZ + salicylic acid |
| L-Serine (1:1) | 1) Dissolve L-serine in $H_2O$<br>2) Dissolve MRZ in THF<br>3) Add L-serine to MRZ<br>4) Stir, RT, 3 days<br>5) SE, RT | 1) Clear, colorless solution<br>2) Clear, colorless solution<br>3) Clear, colorless solution<br>4) Slightly turbid solution<br>5) White solids<br>PLM:agglomerates, B | MRZ |
| L-Serine (1:3) | 1) $H_2O$ added to L-serine<br>2) MeOAc added to MRZ<br>3) $H_2O$ added to MeOAc<br>4) Slurry, 60° C., O/N<br>5) Stir, RT, 1 day<br>6) FE, RT | 1) Solids remain<br>2) Solids remain<br>3) Two layers formed<br>4) Clear, colorless solution<br>5) Clear, colorless solution<br>6) White solids<br>PLM:dendrites, needles, B/E | MRZ |
| Succinic acid (1:1) | DCM, slurry, RT, 6 days | White solids<br>PLM:small particles, unknown morphology, B | MRZ + succinic acid |
| Succinic acid (1:2) | 1) Dissolve succinic acid in MeOH<br>2) Dissolve MRZ in acetone<br>3) Add succinic acid solution to MRZ<br>4) Stir, RT, 5 days | 1) Clear, colorless solution<br>2) Clear, colorless solution<br>3) Clear, colorless solution<br>4) White solids<br>PLM:small particles, unknown morphology, B | MRZ |

TABLE 18-continued

Cocrystal Screen of Marizomib

| Coformer (X:Y) | Conditions | Observations | XRPD Results |
|---|---|---|---|
| Succinic acid (1:5) | 1) Succinic acid dissolved in EtOH, MRZ dissolved in THF, addition of succinic acid solution to MRZ solution 2) Stir, RT, 2 days 3) SE at RT | 1) Clear, colorless solution 2) Clear, colorless solution 3) Translucent solids PLM:needles, rosettes, B/E | MRZ + succinic acid |
| L-(+)-tartaric acid (2:1) | 1) EtOAc, SC, 50° C. to RT 2) Cool to 2-8° C. | 1) White suspension, insufficient for analysis 2) White solids | MRZ + L-(+)-tartaric acid |
| L-(+)-tartaric acid (1:2) | 1) Dissolve L-(+)-tartaric acid in EtOH at 50° C. 2) Dissolve MRZ in dioxane at 50° C. 3) Add L-(+)-tartaric acid solution to MRZ at 50° C. 4) Stir at RT for cool 5) SE at RT | 1) Clear, colorless solution 2) Clear, colorless solution 3) Clear, colorless solution 4) Clear, colorless solution 5) Translucent solids PLM:Needles, B/E | MRZ + minor L-(+)-tartaric acid |
| L-(+)-tartaric acid (1:5) | THF:nitromethane (20:80), slurry, RT, 7 days | White solids PLM:small particles, unknown morphology, B | MRZ + L-(+)-tartaric acid |
| Thymine (1:1) | 1) Add MeOH to thymine at 50° C. 2) Add EtOAc to MRZ at 50° C. 3) Add thymine suspension 4) Slurry at 50° C., 2 days 5) Slurry at RT, 6 days | 1) White suspension 2) White suspension 3) White suspension 4) White suspension 5) White solids PLM:small particles, unknown morphology, B | Thymine |
| Thymine (1:3) | 1) 1-PrOH added to Thymine 2) Added to MRZ 3) Slurry at 60° C., O/N 4) Stir, RT, 1 day | 1) White suspension 2) White suspension 3) White suspension 4) White solids PLM:small particles, unknown morphology | MRZ + thymine |
| Uracil (1:1) | 1) Add $H_2O$ to uracil at 50° C. 2) Add acetone to MRZ 3) Add uracil suspension to MRZ 4) Slurry, RT | 1) White suspension 2) White suspension 3) White suspension 4) White solids PLM:small particles, unknown morphology, B. | MRZ + Uracil |
| Uracil (1:3) | 1) Uracil dissolved in $H_2O$ 2) MRZ dissolved in THF 3) Uracil solntian added to MRZ solution 4) Slurry, 60° C., O/N 5) Stir, RT, 1 day | 1) Clear, colorless solution 2) Clear, colorless solution 3) White suspension 4) White suspension 5) White solids PLM:small particles, unknown morphology | MRZ + uracil |
| Urea (2:1) | EtOAc, FC, 50° C. to RT | White solids PLM:small particles, unknown morphology, B | MRZ |
| Urea (1:1) | Solvent assisted grinding, t-BuOH (3 × 5 minutes, 3 × 20 μL) | White solids | MRZ + urea |
| Urea (1:5) | Dioxane, stir, RT, 7 days | Translucent solids PLM:needles, dendritics | Urea:dioxane solvate + minor MRZ (XRPD) Urea, dioxane, DMSO, water, trace MRZ (1H NMR) |

Example 13—Salt Screen of Marizomib

For crash cooling (CC), a solution of MRZ and coformer was prepared at elevated temperature in a given solvent mixture. The vial was capped and immediately placed in a refrigerator or freezer. For fast cooling (FC), solution of MRZ and coformer were prepared at elevated temperatures in given solvents or solvent mixtures. The vial was capped and placed on a bench top at room temperature to quickly cool. For slow cooling (SC), a solution of MRZ and coformer was prepared at elevated temperature in a given solvent mixture. The vial was capped and left in a heating block at elevated temperature. The heater then was turned off for the sample to cool down naturally to room temperature. For slow evaporation (SE), solutions of MRZ and coformer were generated at ambient temperature in a given solvent or solvent mixture. The solutions were allowed to evaporate partially or to dryness from a loosely capped vial at ambient conditions. Slurry experiments were carried out by making saturated solutions containing excess solid. The slurries were agitated at ambient or elevated temperatures for a specified amount of time. The solids present were recovered via positive pressure filtration. Solvent assisted grinding experiments were carried out by mixing MRZ and coformer in an agate mortar and pestle. Aliquots of solvent were added and the mixture ground manually for specified amount of time. The solids were scraped from the walls of the mortar and the pestle head. Another aliquot of solvent added and ground for several more minutes. For temperature cycling, solutions or suspensions of MRZ and coformer were made in a given solvent and placed at elevated temperature. The sample was cycled by removing from heat and then reapplying several times. The solids were collected via vacuum filtration upon the last cool from elevated temperature.

As set forth in Table 19 below, "X:Y" refers to marizomib:conformer mole ratio. Temperatures and times are approximate. Solvent ratios are by volume. Approximately 60-90 mg of marizomib was used for each experiment.

TABLE 19

Salt Screen of Marizomib

| Counnterion (X:Y) | Conditions | Observations | XRPD Results |
|---|---|---|---|
| Benzenesulfonic acid (1:1) | Anh. acetone, stir, RT, 2 days | Brown solution | — |
| HCl (1:1) | IPA/anh. acetone (3:1), stir, RT, 7 days | White solids PLM: agglomerates of needles, B/E | MRZ |
| HCl (1:2) | IPrOAc, stir, RT (HCl in IPA), 7 days | White solids PLM: small particles, unknown morph, B. | MRZ |
| Methanesulfonic acid (1:1) | Anh. acetone, stir, RT, 1 day | Dark orange solution, yellow solids, experiment discontinued | — |
| Phosphoric acid (1:1) | Dioxane, stir, RT, 4 days | Clear, colorless solution | — |
| Sulfuric acid (1:1) | 2-MeTHF, stir, RT, 2 days | Clear, light yellow solution | — |
| Sulfuric acid (large excess) | Acetone, stir, RT, 2 days | Black solution | — |
| Sulfuric acid (large excess) | Stir in $H_2SO_4$, RT, 2 days | Dark brown solution | — |
| p-toluenesulfonic acid (1:1) | EtOAc, stir, RT, 2 days | White solids PLM: small particles, unknown morphology, B. | MRZ |
| p-toluenesulfonic acid (1:2) | 1) THF, stir, RT, 2 days 2) SE, RT | 1) Clear, colorless solution 2) Off-white solids PLM: agglomerates, B. | MRZ + p-toluene sulfonic acid + unique peaks (7.9, 12.7 2θ) |

EQUIVALENTS

While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention.

The invention claimed is:

1. A co-crystal of marizomib and 2-pyrrolidone, characterized by an X-ray powder diffraction pattern including peaks at about 14.1 and about 15.5°θ using Cu Kα radiation.

2. The co-crystal of claim 1, further including X-ray powder diffraction peaks at about 7.2, about 14.5, and about 36.7°2θ using Cu Kα radiation.

3. The co-crystal of claim 1, further including X-ray powder diffraction peaks at about 18.1, about 19.6, and about 20.8°2θ using Cu Kα radiation.

4. The co-crystal of claim 1, further including X-ray powder diffraction peaks at about 16.3, about 19.8, and about 20.5°2θ using Cu Kα radiation.

5. The co-crystal of claim 1, further including X-ray powder diffraction peaks at about 15.2, about 21.5, and about 22.3°2θ using Cu Kα radiation.

6. The co-crystal of claim 1, further including X-ray powder diffraction peaks at about 14.7, about 29.2, and about 30.0°2θ using Cu Kα radiation.

7. The co-crystal of claim 1, further including X-ray powder diffraction peaks at about 8.2, about 14.8, and about 27.7°2θ using Cu Kα radiation.

8. The co-crystal of claim 1, further including X-ray powder diffraction peaks at about 7.2, about 14.5, about 16.3, about 18.1, about 19.6, about 19.8, about 20.5, about 20.8, and about 36.7°2θ using Cu Kα radiation.

9. The co-crystal of claim 1, further characterized by a degradation event at about 120° C. measured by thermogravimetric analysis.

10. The co-crystal of claim 1, further characterized by two endotherms with peak maxima at about 91.4 and about 131.3° C. as measured by differential scanning calorimetry.

11. A method of preparing a co-crystal of claim 1, wherein marizomib and 2-pyrrolidone are manually ground together.

12. A co-crystal of marizomib and melamine, characterized by an X-ray powder diffraction pattern including peaks at about 12.3, about 16.0, and about 16.5°θ using Cu Kα radiation.

13. The co-crystal of claim 12, further including X-ray powder diffraction peaks at about 7.2, about 14.5, and about 36.7°2θ using Cu Kα radiation.

14. The co-crystal of claim 12, further including X-ray powder diffraction peaks at about 18.1, about 19.6, and about 20.8°2θ using Cu Kα radiation.

15. The co-crystal of claim 12, further including X-ray powder diffraction peaks at about 16.3, about 19.8, and about 20.5°2θ using Cu Kα radiation.

16. The co-crystal of claim 12, further including X-ray powder diffraction peaks at about 15.2, about 21.5, and about 22.3°2θ using Cu Kα radiation.

17. The co-crystal of claim 12, further including X-ray powder diffraction peaks at about 14.7, about 29.2, and about 30.0°2θ using Cu Kα radiation.

18. The co-crystal of claim 12, further including X-ray powder diffraction peaks at about 8.2, about 14.8, and about 27.7°2θ using Cu Kα radiation.

19. The co-crystal of claim 12, further characterized by an exotherm with a peak maximum at about 166° C. as measured by differential scanning calorimetry.

20. The co-crystal of claim 12, further characterized by an endotherm with a peak maximum at about 175° C. as measured by differential scanning calorimetry.

* * * * *